United States Patent [19]

Bereznak et al.

[11] Patent Number: 6,066,638
[45] Date of Patent: May 23, 2000

[54] FUNGICIDAL PYRIMIDINONES

[75] Inventors: James Francis Bereznak, Aston, Pa.; Zen-Yu Chang, Hockessin; Charlene Gross Sternberg, Wilmington, both of Del.

[73] Assignee: E. I. du Pont de Nemours and Company, Wilmington, Del.

[21] Appl. No.: 08/983,086

[22] PCT Filed: Jun. 24, 1996

[86] PCT No.: PCT/US96/10774

§ 371 Date: Jan. 2, 1997

§ 102(e) Date: Jan. 2, 1997

[87] PCT Pub. No.: WO97/02262

PCT Pub. Date: Jan. 23, 1997

Related U.S. Application Data

[60] Provisional application No. 60/000,801, Jul. 5, 1995, and provisional application No. 60/000,787, Jul. 5, 1995.

[51] Int. Cl.[7] ................. A61K 31/505; C07D 493/04; C07D 495/04
[52] U.S. Cl. .................. 514/258; 514/63; 514/248; 514/249; 514/259; 514/262; 514/267; 544/229; 544/236; 544/237; 544/249; 544/255; 544/256; 544/257; 544/258; 544/265; 544/278; 544/279; 544/280; 544/284; 544/285; 544/287; 544/290
[58] Field of Search ...................... 544/278, 280; 514/258

[56] References Cited

U.S. PATENT DOCUMENTS

| | | | |
|---|---|---|---|
| 3,021,332 | 2/1962 | Hitchings et al. | 260/256.4 |
| 3,749,724 | 7/1973 | Wiedemann et al. | 260/256.5 |
| 3,755,582 | 8/1973 | Bullock | 424/251 |
| 3,794,637 | 2/1974 | Wiedemann et al. | 260/256.4 |
| 3,804,835 | 4/1974 | Wiedemann et al. | 260/256.4 |
| 3,867,384 | 2/1975 | Bullock et al. | 260/256.4 |
| 3,931,183 | 1/1976 | Hardtmann | 260/256.4 |
| 4,925,843 | 5/1990 | Takahashi et al. | 514/248 |
| 5,034,393 | 7/1991 | Hackler et al. | 514/258 |
| 5,753,664 | 5/1998 | Aono et al. | 514/258 |

FOREIGN PATENT DOCUMENTS

| | | | |
|---|---|---|---|
| 0 276 825 | 8/1988 | European Pat. Off. | C07D 239/95 |
| 2 210 503 | 9/1972 | Germany | C07D 63/18 |
| 24 11 273 | 9/1975 | Germany | C07D 495/04 |
| 24 11 274 | 9/1975 | Germany | C07D 495/04 |
| 630225383 | 9/1998 | Japan . | |
| WO 94/26722 | 11/1994 | WIPO | C07D 239/95 |
| WO 97/33890 | 9/1997 | WIPO . | |
| WO 99/40074 | 8/1999 | WIPO . | |

OTHER PUBLICATIONS

Sauter et al. Chemical Abstracts, 136088 q., vol. 81, 1974.
F. Sauter et al., Monatshefte fur Chemie 104, 1593–1598 (1973) by Springer–Verlag, Synthese von 2–Mercapto–thieno[2,3–d]pyrimidin–4(3H)–on–Derivaten.
Sauter et al., Chemical Abstracts, 82868c, vol. 80, 1973.

F. Sauter et al., Moatshefte fur Chemie 105, 863–868 (1974) by Springer–Verlag, Synthese von 2–Methylen–2,3–dihydro–und 2–Methyl–5H–thiazolo[3,2–a]pyrimidinen.
Chemical Abstracts 19850m, vol. 110, 1989.
Sugiyama et al., Condensed Thienopyrimidines. II. Synthesis and Gastric Antisecretory Activity of Thiazole and Polymethylene Condensed Thienopyrimidine Derivatives, Chem., Pharm. Bull. 37(8) 2122, pp. 2122–2131, vol. 37, No. 8, 1989.
Quijano M L et al., Synthesis and anticancer and antimicrobial activities of pyrrolo[2,3–d]pyrimidines, *J. Heterocycl. Chem.*, 27(4), 1079–83, 1990.
Okamoto et al., *Bull. Chem. Soc. Jpn.*, 59 (6), 1915–19, 1986.
Kondo et al., *Chem. Lett.*, 80 (5), 559–62, 1980.
Talukdar et al., *Indian J. Chem. Sect. B*, 22B (3), 243–8, 1983.
Reichman et al., *J. Chem. Soc., Perkin Trans. 1*, 73 (22), 2647–55, 1973.
Seela et al., *J. Med. Chem.*, 27 (8), 981–5, 1984.
*Chemical Abstracts*, 75, No. 5, Abstract 34976 (Ul'Yanova et al.), 1971.
*Chemical Abstracts*, 64, No. 7, Abstract 9725a (Nikolaeva), 1966.
El–Feky et al., *Egypt. J. Pharm. Sci.*, 35 (1–6), 246, 1994.
Shukla et al., *Indian J. For.*, 7 (2), 153, 1984.
Mittra et al., *Acta Cienc. Indica.*, 9 (1–4), 109–12, 1983.
Das et al., *J. Indian Chem. Soc.*, 56 (4), 398–400, 1979.
Dave et al., J. Inst. Chemist (India), vol. 57, Jul. 1985, pp. 156–158.

(List continued on next page.)

*Primary Examiner*—Richard L. Raymond

[57] ABSTRACT

Compounds of Formula I, and their N-oxides and agriculturally suitable salts, are disclosed which are useful as fungicides

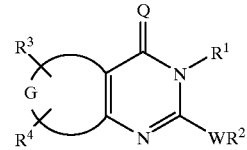

I wherein
  W is O, $S(O)_n$ or $NR^5$;
  n is 0, 1 or 2;
  Q is O or S;
  G is a fused phenyl, naphthalene, thiophene, furan, pyrrole, pyridine, thiazole, oxazole, imidazole, pyrazine, pyridazine or pyrimidine ring; and
  $R^1$–$R^5$ are as defined in the disclosure.

Also disclosed are compositions containing the compounds of Formula I and a method for controlling plant diseases caused by fungal plant pathogens which involves applying an effective amount of a compound of Formula I.

17 Claims, No Drawings

OTHER PUBLICATIONS

Translation of East German Patent No. 240892A, Nov. 19, 1986.

Urleb et al., The Synthesis and Transformations of 3–Ethoxycarbonyl–2–isothiocyanato–pyridine, Pyrido[2,3–d]pyrimidines and Some Azolopyrido[2,3–d]pyrimidines. J. Heterocyclic Chem., vol. 27, pp. 643–646, Mar.–Apr. 1990.

Urleb et al., The Synthesis and Transformations of 2–Ethoxycarbonyl–3–Isothiocyana–topyridine. Pyrido[3,2–d]pyrimidines and some Azolopyrido[3,2–d]pyrimidines. J. Heterocyclic Chem., vol. 27, pp. 407–412, Feb. 1990.

Urleb et al., The Reaction of 2–Ethoxycarbonyl–3–isothiocyanatopyridine with a–Amino Acids. The Synthesis of 3–Substituted 2–Thiooxo–2,3–dihydropyrido[3,2–d]pyrimidin–4(3H)–ones, J. Heterocyclic Chem., pp. 413–415, vol. 27, Feb. 1990.

Prameela B., et al., Synthesis and Antifungal Activity of Isoxazolylquinazolin–4(3H)–ones, Indian Journal of Heterocyclic Chemistry, 2, 115–118, 1992.

Abstract, HU 62757–T, Fungicide—Comprising Quinazoline Derivative, C2 Heterocyclic, eek 9332, 6, 1993.

FUNGICIDAL PYRIMIDINONES

This application is a national filing under 35 USC 371 of International Application No. PCT/US96/10774 filed Jun. 24, 1996, and claims priority, in part, of U.S. Provisional Application No. 60/000,801 filed Jul. 5, 1995, and priority, in part, of U.S. Provisional Application No. 60/000,787 filed Jul. 5, 1995.

BACKGROUND OF THE INVENTION

This invention relates to certain pyrimidinones, their N-oxides, agriculturally suitable salts and compositions, and methods of their use as fungicides.

The control of plant diseases caused by fungal plant pathogens is extremely important in achieving high crop efficiency. Plant disease damage to ornamental, vegetable, field, cereal, and fruit crops can cause significant reduction in productivity and thereby result in increased costs to the consumer. Many products are commercially available for these purposes, but the need continues for new compounds which are more effective, less costly, less toxic, environmentally safer or have different modes of action.

DT 2,210,503, DT 2,411,274, DT 2,411,273, and DD-A-240,892 disclose certain thienopyrimidine compounds. These publications, however, do not disclose the compounds of the present invention nor agricultural fungicide utility. U.S. Pat. No. 3,755,582 and U.S. Pat. No. 3,867,384 disclose certain 4(3H)-quinazolinone fungicides. These publications, however, do not disclose the compounds of the present invention.

SUMMARY OF THE INVENTION

This invention is directed to compounds of Formula I including all geometric and stereoisomers, N-oxides, and agriculturally suitable salts thereof, agricultural compositions containing them and their use as fungicides:

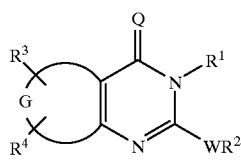

I wherein
W is O, $S(O)_n$ or $NR^5$;
n is 0, 1 or 2;
Q is O or S;
G is a fused phenyl, naphthalene, thiophene, furan, pyrrole, pyridine, thiazole, oxazole, imidazole, pyrazine, pyridazine or pyrimidine ring;
$R^1$ is $C_1$–$C_{10}$ alkyl; $C_3$–$C_6$ cycloalkyl; $C_3$–$C_{10}$ alkenyl; $C_3$–$C_{10}$ alkynyl; $C_1$–$C_{10}$ haloalkyl; $C_3$–$C_{10}$ haloalkenyl; $C_3$–$C_{10}$ haloalkynyl; $C_2$–$C_{10}$ alkoxyalkyl; $C_2$–$C_{10}$ alkylthioalkyl; $C_2$–$C_{10}$ alkylsulfonylalkyl; $C_4$–$C_{10}$ cycloalkylalkyl; $C_4$–$C_{10}$ alkenyloxyalkyl; $C_4$–$C_{10}$ alkynyloxyalkyl; $C_4$–$C_{10}$ alkenylthioalkyl; $C_4$–$C_{10}$ alkynylthioalkyl; $C_2$–$C_{10}$ haloalkoxyalkyl; $C_4$–$C_{10}$ alkoxyalkenyl; $C_4$–$C_{10}$ alkylthioalkenyl; $C_4$–$C_{10}$ trialkylsilylalkyl; $C_1$–$C_{10}$ alkoxy; $NR^6R^7$; $R^{11}$; phenyl, pyridinyl, furanyl, thienyl, naphthalenyl, benzofuranyl, benzo[b]thiophenyl or quinolinyl each optionally substituted with $R^8$, $R^9$ and $R^{10}$; or $C_1$–$C_{10}$ alkyl substituted with $NR^6R^7$, nitro, cyano, $CO_2R^6$, or phenyl optionally substituted with $R^8$, $R^9$ and $R^{10}$;

$R^2$ is $C_1$–$C_{10}$ alkyl; $C_3$–$C_7$ cycloalkyl; $C_3$–$C_{10}$ alkenyl; $C_3$–$C_{10}$ alkynyl; $C_1$–$C_{10}$ haloalkyl; $C_3$–$C_{10}$ haloalkenyl; $C_3$–$C_{10}$ haloalkynyl; $C_2$–$C_{10}$ alkoxyalkyl; $C_2$–$C_{10}$ alkylthioalkyl; $C_2$–$C_{10}$ alkylsulfonylalkyl; $C_4$–$C_{10}$ cycloalkylalkyl; $C_4$–$C_{10}$ alkenyloxyalkyl; $C_4$–$C_{10}$ alkynyloxyalkyl; $C_4$–$C_{10}$ alkenylthioalkyl; $C_4$–$C_{10}$ alkynylthioalkyl; $C_2$–$C_{10}$ haloalkoxyalkyl; $C_4$–$C_{10}$ alkoxyalkenyl; $C_4$–$C_{10}$ alkylthioalkenyl; $C_4$–$C_{10}$ trialkylsilylalkyl; $R^{11}$; phenyl optionally substituted with $R^8$, $R^9$ and $R^{10}$; or $C_1$–$C_{10}$ alkyl substituted with $NR^6R^7$, cyano, nitro, $CO_2R^6$, or phenyl optionally substituted with $R^8$, $R^9$ and $R^{10}$; or
when W is $NR^5$, then $R^2$ can additionally be selected from —$OR^7$; —$N=CR^6R^6$; —$NR^6R^7$; and pyridinyl, furanyl, thienyl and naphthalenyl each optionally substituted with $R^8$, $R^9$ and $R^{10}$; or
when W is O, then $R^2$ can additionally be selected from —$N=CR^6R^6$ and —$NR^6R^7$;
$R^3$ is hydrogen; halogen; $C_1$–$C_8$ alkyl; $C_3$–$C_8$ cycloalkyl; $C_2$–$C_8$ alkenyl; $C_2$–$C_8$ alkynyl; $C_1$–$C_8$ haloalkyl; $C_3$–$C_8$ haloalkenyl; $C_3$–$C_8$ haloalkynyl; $C_1$–$C_8$ alkoxy; $C_1$–$C_8$ haloalkoxy; $C_3$–$C_8$ alkenyloxy; $C_3$–$C_8$ alkynyloxy; $C_1$–$C_8$ alkylthio; $C_1$–$C_8$ alkylsulfonyl; $C_2$–$C_8$ alkoxyalkyl; $C_3$–$C_8$ trialkylsilyl; nitro; $NR^6R^7$; $C_5$–$C_8$ trialkylsilylalkynyl; or phenyl optionally substituted with at least one $R^{13}$;
$R^4$ is hydrogen, halogen, $C_1$–$C_4$ alkyl, $C_1$–$C_4$ haloalkyl, $C_1$–$C_4$ alkoxy or $C_1$–$C_4$ haloalkoxy;
$R^5$ is hydrogen, $C_1$–$C_4$ alkyl or —$C(=O)R^{12}$;
each $R^6$ is independently hydrogen; $C_1$–$C_4$ alkyl; or phenyl optionally substituted with at least one $R^{13}$;
each $R^7$ is independently hydrogen; $C_1$–$C_8$ alkyl; or phenyl optionally substituted with at least one $R^{13}$; or
each pair of $R^6$ and $R^7$, when attached to the same nitrogen atom, can independently be taken together as —$CH_2CH_2CH_2CH_2$—, —$CH_2(CH_2)_3CH_2$—, —$CH_2CH_2OCH_2CH_2$—, —$CH_2CH(Me)CH_2CH(Me)CH_2$— or —$CH_2CH(Me)OCH(Me)CH_2$—;
each $R^8$ is independently $C_1$–$C_6$ alkyl; $C_1$–$C_6$ alkoxy; $C_1$–$C_6$ haloalkyl; halogen; $C_2$–$C_8$ alkynyl; $C_1$–$C_6$ alkylthio; phenyl or phenoxy each optionally substituted with at least one $R^{13}$; cyano; nitro; $C_1$–$C_6$ haloalkoxy; $C_1$–$C_6$ haloalkylthio; $C_2$–$C_6$ alkenyl; $C_2$–$C_6$ haloalkenyl; acetyl; $CO_2Me$; or $N(C_1$–$C_2$ alkyl)$_2$;
each $R^9$ is independently methyl, ethyl, methoxy, methylthio, halogen, $CO_2(C_1$–$C_3$ alkyl), $C(O)NR^6R^7$ or trifluoromethyl;
each $R^{10}$ is independently halogen;
each $R^{11}$ is independently $C_1$–$C_{10}$ alkyl substituted with an 8-, 9- or 10-membered fused carbobicyclic or fused heterobicyclic ring; or $R^{11}$ is $C_1$–$C_{10}$ alkyl substituted with a 3-, 4-, 5- or 6-membered heteromonocyclic ring; wherein said heterobicyclic or heteromonocyclic rings contain 1 to 4 heteroatoms independently selected from the group nitrogen, oxygen and sulfur, provided that each heterobicyclic or heteromonocyclic ring contains no more than 4 nitrogens, no more than 2 oxygens and no more than 2 sulfurs, wherein said heterobicyclic or heteromonocyclic ring is bonded to the alkyl group through a carbon atom of the ring, and wherein said carbobicyclic, heterobicyclic or heteromonocyclic ring is optionally substituted with $R^8$, $R^9$ and $R^{10}$;
$R^{12}$ is hydrogen, $C_1$–$C_4$ alkyl, $C_1$–$C_4$ alkoxy or $NR^6R^7$; and
each $R^{13}$ is independently halogen, $C_1$–$C_4$ alkyl, $C_1$–$C_4$ alkoxy, $C_1$–$C_4$ haloalkyl, nitro or cyano;

provided that
(i) when G is a fused thiophene ring, then $R^3$ is other than hydrogen, $C_1$–$C_8$ alkyl, nitro or phenyl optionally substituted with at least one $R^{13}$;
(ii) when G is a fused pyridine ring, then $R^3$ is other than hydrogen or $C_1$–$C_8$ alkyl;
(iii) when G is a fused imidazole ring, then $R^3$ is other than hydrogen or $C_1$–$C_8$ alkyl; and
(iv) when G is a fused phenyl ring, then at least one of $R^1$ and $R^2$ is $R^{11}$.

DETAILS OF THE INVENTION

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl. "Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkenyloxy" includes straight-chain or branched alkenyloxy moieties. Examples of "alkenyloxy" include $H_2C=CHCH_2O$, $(CH_3)_2C=CHCH_2O$, $(CH_3)CH=CHCH_2O$, $(CH_3)CH=C(CH_3)CH_2O$ and $CH_2=CHCH_2CH_2O$. "Alkynyloxy" includes straight-chain or branched alkynyloxy moieties. Examples of "alkynyloxy" include $HC\equiv CCH_2O$, $CH_3C\equiv CCH_2O$ and $CH_3C\equiv CCH_2CH_2O$. "Alkylthio" includes branched or straight-chain alkylthio moieties such as methylthio, ethylthio, and the different propylthio, butylthio, pentylthio and hexylthio isomers. "Alkylthioalkyl" denotes alkylthio substitution on alkyl. Examples of "alkylthioalkyl" include $CH_3SCH_2$, $CH_3SCH_2CH_2$, $CH_3CH_2SCH_2$, $CH_3CH_2CH_2CH_2SCH_2$ and $CH_3CH_2SCH_2CH_2$. Examples of "alkylsulfonyl" include $CH_3S(O)_2$, $CH_3CH_2S(O)_2$, $CH_3CH_2CH_2S(O)_2$, $(CH_3)_2CHS(O)_2$ and the different butylsulfonyl, pentylsulfonyl and hexylsulfonyl isomers. "Trialkylsilyl" includes $(CH_3)_3Si$, $(CH_3CH_2)_3Si$ and $[(CH_3)_3C](CH_3)_2Si$. "Alkylsulfonylalkyl", "alkenyloxyalkyl", "alkynyloxyalkyl", "alkenylthioalkyl", and the like, are defined analogously to the above examples. "Cycloalkyl" includes, for example, cyclopropyl, cyclobutyl, cyclopentyl, and cyclohexyl. Examples of "cycloalkylalkyl" include cyclopropylmethyl, cyclopentylethyl, and other cycloalkyl moieties bonded to straight-chain or branched alkyl groups. One skilled in the art will appreciate that not all nitrogen containing heterocycles can form N-oxides since the nitrogen requires an available lone pair for oxidation to the oxide; one skilled in the art will recognize those nitrogen containing heterocycles which can form N-oxides. One skilled in the art will also recognize that the N-oxides of compounds of Formula I can be made by oxidizing the corresponding nitrogen compound with a strong oxidizing agent such as meta-chloroperoxybenzoic acid.

The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CCl_2$. The terms "haloalkenyl", "haloalkynyl", "haloalkoxy", and the like, are defined analogously to the term "haloalkyl". Examples of "haloalkenyl" include $(Cl)_2C=CHCH_2$ and $CF_3CH_2CH=CHCH_2$. Examples of "haloalkynyl" include $HC\equiv CCHCl$, $CF_3C\equiv C$, $CCl_3C\equiv C$ and $FCH_2C\equiv CCH_2$. Examples of "haloalkoxy" include $CF_3O$, $CCl_3CH_2O$, $HCF_2CH_2CH_2O$ and $CF_3CH_2O$. Examples of "haloalkylthio" include $CCl_3S$, $CF_3S$, $CCl_3CH_2S$ and $ClCH_2CH_2CH_2S$.

The total number of carbon atoms in a substituent group is indicated by the "$C_i$–$C_j$" prefix where i and j are numbers from 1 to 10. For example, $C_1$–$C_3$ alkylsulfonyl designates methylsulfonyl through propylsulfonyl; $C_2$ alkoxyalkyl designates $CH_3OCH_2$; $C_3$ alkoxyalkyl designates, for example, $CH_3CH(OCH_3)$, $CH_3OCH_2CH_2$ or $CH_3CH_2OCH_2$; and $C_4$ alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$. In the above recitations, when a compound of Formula I is comprised of one or more heterocyclic rings, all substituents are attached to these rings through any available carbon or nitrogen by replacement of a hydrogen on said carbon or nitrogen.

Exemplary values of a 8-, 9- or 10-membered fused carbobicyclic or fused heterobicyclic ring, and a 3-, 4-, 5- or 6-membered heteromonocyclic ring wherein said heterobicyclic or heteromonocyclic rings contain 1 to 4 heteroatoms independently selected from the group nitrogen, oxygen and sulfur, provided that each heterobicyclic or heteromonocyclic ring contains no more than 4 nitrogens, no more than 2 oxygens and no more than 2 sulfurs, include the ring systems illustrated in Exhibit 1. As with the carbon atoms in the ring, the nitrogen atoms which require substitution to fill their valence are substituted with hydrogen or with $R^8$, $R^9$ or $R^{10}$. In the bicyclic ring systems (e.g., Y-66–Y-90), the $R^8$, $R^9$ and $R^{10}$ groups may substitute either ring. Although the $R^8$, $R^9$ and/or $R^{10}$ groups are shown in the structures Y-1 to Y-100, it is noted that they do not need to be present since they are optional substituents.

Exhibit 1

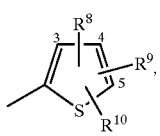

Y-1

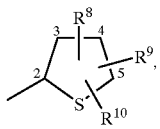

Y-2

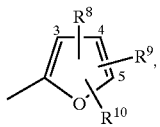

Y-3

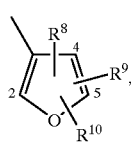
Y-4
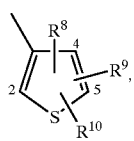
Y-5
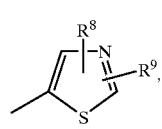
Y-6
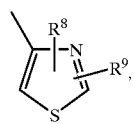
Y-7
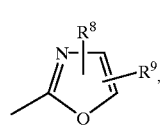
Y-8
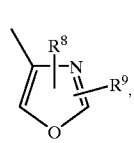
Y-9
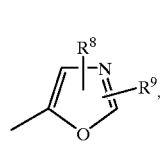
Y-10
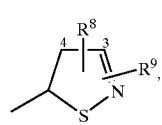
Y-11
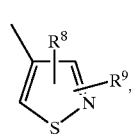
Y-12
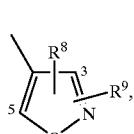
Y-13
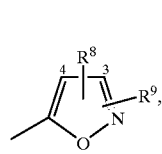
Y-14
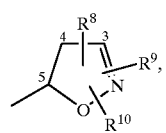
Y-15
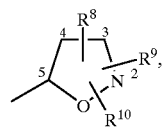
Y-16
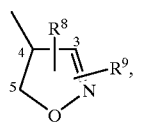
Y-17
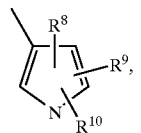
Y-18
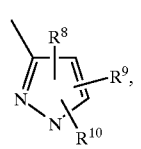
Y-19
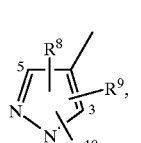
Y-20
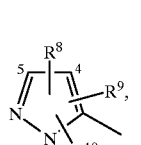
Y-21
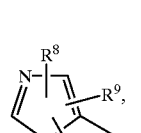
Y-22
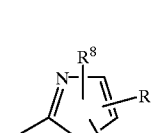
Y-23
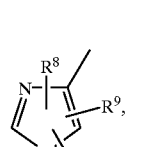
Y-24
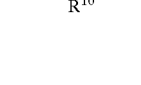

-continued
Y-25 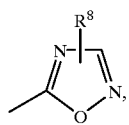
Y-26 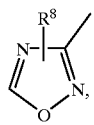
Y-27 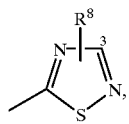
Y-28 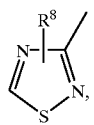
Y-29 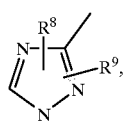
Y-30 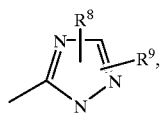
Y-31 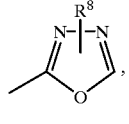
Y-32 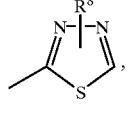
Y-33 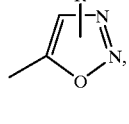
Y-34 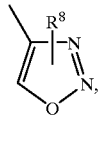
Y-35 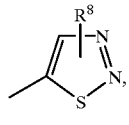
-continued
Y-36 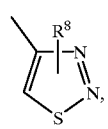
Y-37 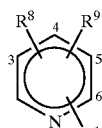
Y-38 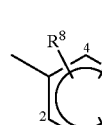
Y-39 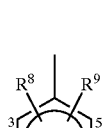
Y-40 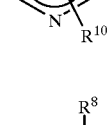
Y-41 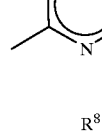
Y-42 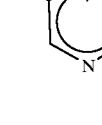
Y-43 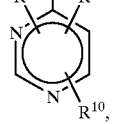
Y-44 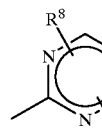
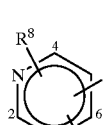

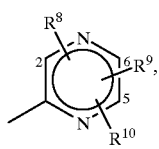 Y-45
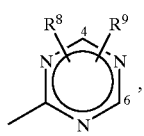 Y-46
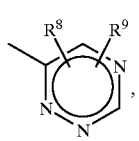 Y-47
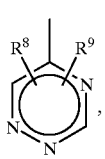 Y-48
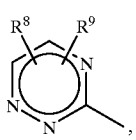 Y-49
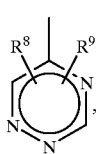 Y-50
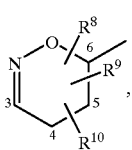 Y-51
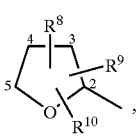 Y-52
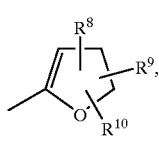 Y-53
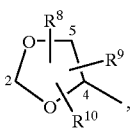 Y-54
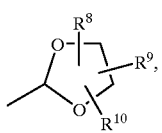 Y-55
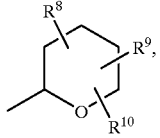 Y-56
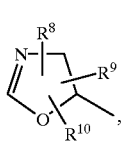 Y-57
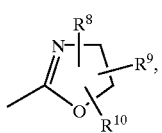 Y-58
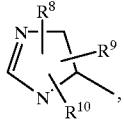 Y-59
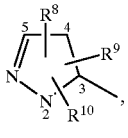 Y-60
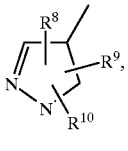 Y-61
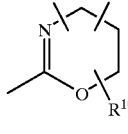 Y-62
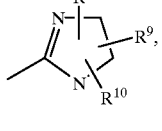 Y-63
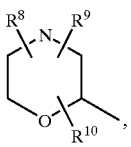 Y-64

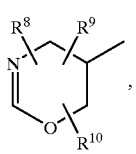, Y-65
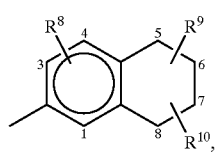, Y-66
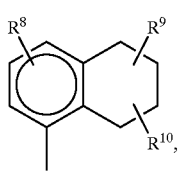, Y-67
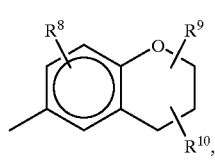, Y-68
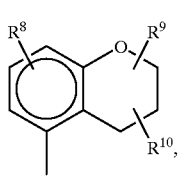, Y-69
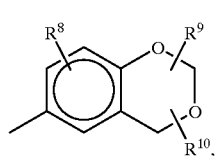, Y-70
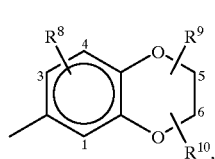, Y-71
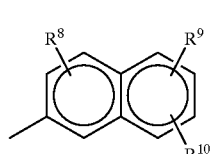, Y-72
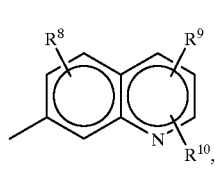, Y-73
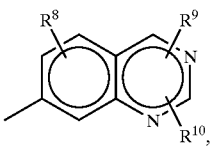, Y-74
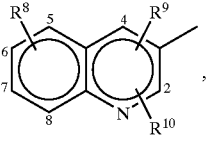, Y-75
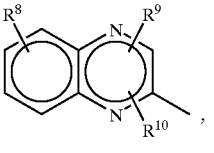, Y-76
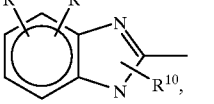, Y-77
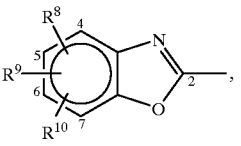, Y-78
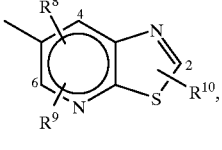, Y-79
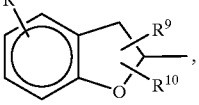, Y-80
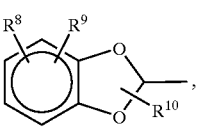, Y-81
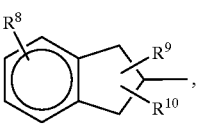, Y-82
Y-83

-continued

Y-84 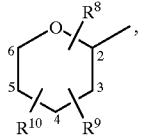

Y-85 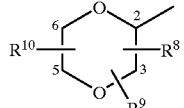

Y-86 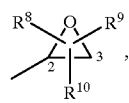

Y-87 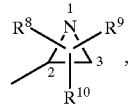

Y-88 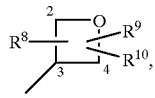

Y-89 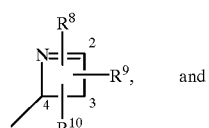

Y-90

Y-91 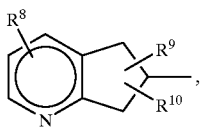

Y-92 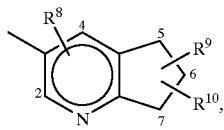

Y-93 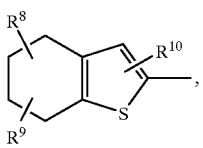

Y-94 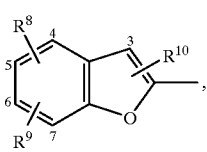

Y-95 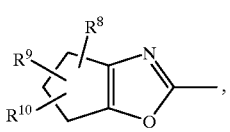

Y-96 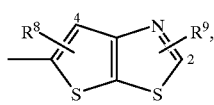

Y-97 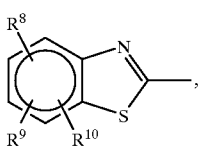

Y-98 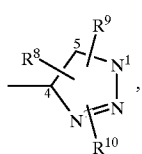

Y-99 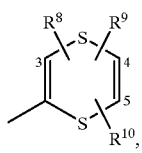

and

Y-100 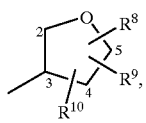

When a group contains a substituent which can be hydrogen, for example $R^3$ or $R^7$, then, when this substituent is taken as hydrogen, it is recognized that this is equivalent to said group being unsubstituted.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. Accordingly, the present invention comprises compounds selected from Formula I, N-oxides and agriculturally suitable salts thereof. The compounds of the invention may be present as a mixture of stereoisomers, individual stereoisomers, or as an optically active form.

The salts of the compounds of the invention include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. The salts of the compounds of the invention also include those formed with organic bases (e.g., pyridine, ammonia, or triethylamine) or inorganic bases (e.g., hydrides, hydroxides, or carbonates of sodium, potassium, lithium, calcium, magnesium or barium) when the compound contains an acidic group.

Preferred compounds for reasons of better activity and/or ease of synthesis are:

Preferred 1. Compounds of Formula I above, and N-oxides and agriculturally suitable salts thereof, wherein:

Q is O;

G is a fused naphthalene, thiophene, pyridine, thiazole, oxazole or pyrimidine ring;

$R^1$ is $C_1$–$C_8$ alkyl; $C_3$–$C_5$ cycloalkyl; $C_3$–$C_8$ alkenyl; $C_3$–$C_8$ alkynyl; $C_1$–$C_8$ haloalkyl; $C_3$–$C_8$ haloalkenyl; $C_2$–$C_8$ alkoxyalkyl; $C_2$–$C_8$ alkylthioalkyl; $C_4$–$C_8$ cycloalkylalkyl; $C_4$–$C_8$ alkenyloxyalkyl; $C_1$–$C_8$ alkoxy; phenyl, pyridinyl, furanyl or thienyl each optionally substituted with $R^8$ and $R^9$; or $C_1$–$C_8$ alkyl substituted with cyano;

$R^2$ is $C_1$–$C_8$ alkyl; $C_3$–$C_8$ alkenyl; $C_3$–$C_8$ alkynyl; $C_1$–$C_8$ haloalkyl; $C_3$–$C_8$ haloalkenyl; $C_2$–$C_8$ alkoxyalkyl; $C_2$–$C_8$ alkylthioalkyl; $C_4$–$C_8$ cycloalkylalkyl; $C_4$–$C_8$ alkenyloxyalkyl; phenyl optionally substituted with $R^8$; or $C_1$–$C_8$ alkyl substituted with cyano; or when W is $NR^5$, then $R^2$ can additionally be selected from —N=$CR^6R^6$ and —$NR^6R^7$;

$R^3$ is hydrogen, halogen, $C_1$–$C_8$ alkyl, $C_3$–$C_8$ cycloalkyl, $C_2$–$C_8$ alkynyl, $C_1$–$C_8$ haloalkyl, $C_1$–$C_8$ alkoxy, $C_1$–$C_8$ haloalkoxy, $C_1$–$C_8$ alkylthio, $C_1$–$C_8$ alkylsulfonyl, $C_2$–$C_8$ alkoxyalkyl or $C_5$–$C_8$ trialkylsilylalkynyl;

each $R^8$ is independently methyl, ethyl, methoxy, ethoxy, $C_1$–$C_2$ haloalkyl, halogen, ethynyl, 2-propynyl, methylthio, ethylthio, cyano, nitro, $C_1$–$C_2$ haloalkoxy, ethenyl, 2-propenyl, acetyl, $CO_2Me$ or $N(C_1$–$C_2$ alkyl)$_2$; and $R^9$ is methyl, ethyl, methoxy, methylthio, halogen or trifluoromethyl.

Preferred 2. Compounds of Preferred 1 wherein:

G is a fused naphthalene, thiophene or pyridine ring;

$R^1$ is $C_3$–$C_8$ alkyl; $C_3$–$C_8$ alkenyl; $C_3$–$C_8$ alkynyl; $C_3$–$C_8$ haloalkyl; $C_3$–$C_8$ haloalkenyl; $C_3$–$C_8$ alkoxyalkyl; or phenyl optionally substituted with $R^8$ and $R^9$;

$R^2$ is $C_3$–$C_8$ alkyl; $C_3$–$C_8$ alkenyl; $C_3$–$C_8$ alkynyl; $C_3$–$C_8$ haloalkyl; $C_3$–$C_8$ haloalkenyl; $C_3$–$C_8$ alkoxyalkyl; or phenyl optionally substituted with $R^8$; or when W is $NR^5$, then $R^2$ can additionally be selected from —N=$CR^6R^6$ and —$NR^6R^7$;

$R^3$ is halogen, $C_1$–$C_4$ alkyl, ethynyl, $C_1$–$C_4$ haloalkyl, $C_1$–$C_4$ alkoxy, $C_1$–$C_4$ haloalkoxy or trimethylsilylethynyl; and each $R^8$ is independently methyl, ethyl, methoxy, trifluoromethyl, halogen, methylthio or $N(C_1$–$C_2$ alkyl)$_2$.

Preferred 3. Compounds of Preferred 2 wherein:

G is a fused thiophene or pyridine ring;

$R^1$ is $C_3$–$C_8$ alkyl, $C_3$–$C_8$ alkenyl, $C_3$–$C_8$ alkynyl, $C_3$–$C_8$ haloalkyl or $C_3$–$C_8$ haloalkenyl;

$R^2$ is $C_3$–$C_8$ alkyl; $C_3$–$C_8$ alkenyl; $C_3$–$C_8$ alkynyl; $C_3$–$C_8$ haloalkyl; $C_3$–$C_8$ haloalkenyl; or phenyl optionally substituted with $R^8$;

$R^3$ is halogen; and $R^4$ is hydrogen or halogen.

Preferred 4. Compounds of Formula I above, and N-oxides and agriculturally suitable salts thereof, wherein:

Q is O;

G is a fused phenyl ring;

$R^1$ is $C_1$–$C_8$ alkyl; $C_3$–$C_6$ cycloalkyl; $C_3$–$C_8$ alkenyl; $C_3$–$C_8$ alkynyl; $C_1$–$C_8$ haloalkyl; $C_3$–$C_8$ haloalkenyl; $C_2$–$C_8$ alkoxyalkyl; $C_2$–$C_8$ alkylthioalkyl; $C_4$–$C_8$ cycloalkylalkyl; $C_4$–$C_8$ alkenyloxyalkyl; $C_1$–$C_8$ alkoxy; $R^{11}$; phenyl, pyridinyl, furanyl or thienyl each optionally substituted with $R^8$ and $R^9$; or $C_1$–$C_8$ alkyl substituted with cyano;

$R^2$ is $C_1$–$C_8$ alkyl; $C_3$–$C_8$ alkenyl; $C_3$–$C_8$ alkynyl; $C_1$–$C_8$ haloalkyl; $C_3$–$C_8$ haloalkenyl; $C_2$–$C_8$ alkoxyalkyl; $C_2$–$C_8$ alkylthioalkyl; $C_4$–$C_8$ cycloalkylalkyl; $C_4$–$C_8$ alkenyloxyalkyl; $R^{11}$; phenyl optionally substituted with $R^8$; or $C_1$–$C_8$ alkyl substituted with cyano; or when W is $NR^5$, then $R^2$ can additionally be selected from —N=$CR^6R^6$ and —$NR^6R^7$;

$R^3$ is hydrogen, halogen, $C_1$–$C_8$ alkyl, $C_2$–$C_8$ alkynyl, $C_1$–$C_8$ haloalkyl, $C_1$–$C_8$ alkoxy, $C_1$–$C_8$ haloalkoxy, $C_1$–$C_8$ alkylthio, $C_1$–$C_8$ alkylsulfonyl, or $C_5$–$C_8$ trialkylsilylalkynyl;

each $R^8$ is independently methyl, ethyl, methoxy, ethoxy, $C_1$–$C_2$ haloalkyl, halogen, ethynyl, 2-propynyl, methylthio, ethylthio, cyano, nitro, $C_1$–$C_2$ haloalkoxy, ethenyl, 2-propenyl, acetyl or $N(C_1$–$C_2$ alkyl)$_2$; and each $R^{11}$ is independently $C_1$–$C_6$ alkyl substituted with a 8-, 9- or 10-membered fused carbobicyclic or fused heterobicyclic ring; or $R^{11}$ is $C_1$–$C_6$ alkyl substituted with a 5- or 6-membered heteromonocyclic ring; wherein said heterobicyclic or heteromonocyclic rings contain 1 to 4 heteroatoms independently selected from the group nitrogen, oxygen and sulfur, provided that each heterobicyclic or heteromonocyclic ring contains no more than 4 nitrogens, no more than 2 oxygens and no more than 2 sulfurs, and wherein said carbobicyclic, heterobicyclic or heteromonocyclic ring is optionally substituted with $R^8$ and $R^9$.

Preferred 5. Compounds of Preferred 4 wherein:

$R^1$ is $C_3$–$C_8$ alkyl; $C_3$–$C_5$ cycloalkyl; $C_3$–$C_8$ alkenyl; $C_3$–$C_8$ alkynyl; $C_3$–$C_8$ haloalkyl; $C_3$–$C_8$ haloalkenyl; $C_3$–$C_8$ alkoxyalkyl; $C_4$–$C_5$ cycloalkylalkyl; $R^{11}$; or phenyl optionally substituted with $R^8$ and $R^9$;

$R^2$ is $C_3$–$C_8$ alkyl; $C_3$–$C_8$ alkenyl; $C_3$–$C_8$ alkynyl; $C_3$–$C_8$ haloalkyl; $C_3$–$C_8$ haloalkenyl; $C_3$–$C_8$ alkoxyalkyl; $R^{11}$; or phenyl optionally substituted with $R^8$; or when W is $NR^5$, then $R^2$ can additionally be selected from —N=$CR^6R^6$ and —$NR^6R^7$;

$R^3$ is halogen, $C_1$–$C_4$ alkyl, ethynyl, $C_1$–$C_4$ haloalkyl, $C_1$–$C_4$ alkoxy, $C_1$–$C_4$ haloalkoxy or trimethylsilylethynyl;

each $R^8$ is independently methyl, ethyl, methoxy, trifluoromethyl, halogen, methylthio or $N(C_1$–$C_2$ alkyl)$_2$; and each $R^{11}$ is independently $C_1$–$C_4$ alkyl substituted with a fused heterobicyclic ring selected from 1,3-benzodioxole, benzo[b]thiophene and benzofuran; or $R^{11}$ is $C_1$–$C_4$ alkyl substituted with a 5- or 6-membered heteromonocyclic ring selected from thiophene, furan, thiazole, oxazole, isothiazole, isoxazole, pyrrole, pyrazole, imidazole, tetrahydrofuran, 1,3-dioxolane, dihydrooxazole, dihydroimidazole, dihydropyrazole, dihydroisoxazole, pyridine, dihydrooxazine, tetrahydropyran and morpholine; wherein said heterobicyclic or heteromonocyclic ring is optionally substituted with $R^8$ and $R^9$.

Preferred 6. Compounds of Preferred 5 wherein:

$R^1$ is $R^{11}$;

$R^2$ is $C_3$–$C_8$ alkyl; $C_3$–$C_8$ alkenyl; $C_3$–$C_8$ alkynyl; $C_3$–$C_8$ haloalkyl; $C_3$–$C_8$ haloalkenyl; or phenyl optionally substituted with $R^8$;

$R^3$ is halogen;

$R^4$ is hydrogen or halogen; and $R^{11}$ is $C_1$–$C_4$ alkyl substituted with a 5- or 6-membered heteromonocyclic ring selected from thiophene, furan, thiazole, oxazole, isothiazole, isoxazole, pyrazole, imnidazole, tetrahydrofuran, 1,3-dioxolane, dihydropyrazole, dihydroisoxazole, pyridine and dihydrooxazine; wherein said heteromonocyclic ring is optionally substituted with $R^8$ and $R^9$.

Most preferred are compounds of Formula I selected from the group:

7-bromo-2-propoxy-3-propylthieno[3,2-d]pyrimidin4(3H)-one;

6-bromo-2-propoxy-3-propylpyrido[2,3-d]pyrimidin-4(3H)-one;

6-bromo-3-propyl-2-(propylthio)pyrido[2,3-d]pyrimidin-4(3H)-one;

6-iodo-2-propyloxy-3-[(tetrahydro-2-furanyl)methyl]-4(3H)-quinazolinone;

6-bromo-2-propyloxy-3-[(tetrahydro-2-furanyl)methyl]-4(3H)-quinazolinone;

6-bromo-3-[(3-bromo-4,5-dihydro-5-isoxazolyl)methyl]-2-propoxy-4(3H)-quinazolinone;

6,7-dibromo-2-propoxy-3-propylthieno[3,2-d]pyrimidin4(3H)-one;

6,8-diiodo-2-(propylthio)-3-[(tetrahydro-2-furanyl)methyl]-4(3H)-quinazolinone; and 3-(cyclopropylmethyl)-6-iodo-2-(propylthio)pyrido[2,3-d]pyrimidin-4(3H)-one.

This invention also relates to fungicidal compositions comprising fungicidally effective amounts of the compounds of the invention and at least one of a surfactant, a solid diluent or a liquid diluent. The preferred compositions of the present invention are those which comprise the above preferred compounds.

This invention also relates to a method for controlling plant diseases caused by fungal plant pathogens comprising applying to the plant or portion thereof, or to the plant seed or seedling, a fungicidally effective amount of the compounds of the invention (e.g., as a composition described herein). The preferred methods of use are those involving the above preferred compounds.

Of note are embodiments where each $R^9$ is independently methyl, ethyl, methoxy, methylthio, halogen or trfuoromethyl when G is other than a fused phenyl ring; embodiments where $R^3$ is hydrogen, halogen, $C_1$–$C_8$ alkyl, $C_2$–$C_8$ alkenyl, $C_2$–$C_8$ alkynyl, $C_1$–$C_8$ haloalkyl, $C_3$–$C_8$ haloalkenyl, $C_3$–$C_8$ haloalkynyl, $C_1$–$C_8$ alkoxy, $C_1$–$C_8$ haloalkoxy, $C_1$–$C_8$ alkylthio, $C_1$–$C_8$ alkylsulfonyl, $C_3$–$C_8$ trialkylsilyl, nitro, $NR^6R^7$ or $C_5$–$C_8$ trialkylsilylalkynyl when G is a fused phenyl ring; and embodiments where each $R^8$ is independently $C_1$–$C_6$ alkyl, $C_1$–$C_6$ alkoxy, $C_1$–$C_6$ haloalkyl, halogen, $C_2$–$C_8$ alkynyl, $C_1$–$C_6$ alkylthio, phenyl or phenoxy each optionally substituted with $R^{13}$, cyano, nitro, $C_1$–$C_6$ haloalkoxy, $C_1$–$C_6$ haloalkylthio, $C_2$–$C_6$ alkenyl, $C_2$–$C_6$ haloalkenyl, acetyl or $N(C_1$–$C_2$ alkyl$)_2$ when G is a fused phenyl ring.

The compounds of Formula I can be prepared by one or more of the following methods and variations as described in Schemes 1–17. The definitions of W, n, Q, G, $R^1$–$R^{13}$ in the compounds of Formulae 1–6 below are as defined above in the Summary of the Invention. Compounds of Formulae Ia–It are various subsets of the compounds of Forrnula I, and all substituents for Formulae Ia–It are as defined above for Formula I.

The synthesis of compounds of Formula I is described below. First, the synthesis of the pyrimidinone ring system is described. In this first section, when $R^1$ and/or $R^2$ are $R^{11}$, the $R^{11}$ substituent is incorporated into the substrates which are used in the syntheses described therein. Alternatively, the pyrimidinone ring system can be prepared using a precursor to the $R^{11}$ group, and then the $R^{11}$ group can be introduced afterwards. Syntheses of various $R^{11}$ groups are described in the second section which describes this alternate strategy.

Synthesis of the Pyrimidinone Ring System

Compounds of Formula Ib, compounds of Formula I wherein W and Q are each O, can be made by the method illustrated in Scheme 1.

A 2-aminoaryl carboxylic acid of Formula 1 is condensed with an isothiocyanate of Formula $R^1$-NCS to form the 2-thiopyrimidinone of Formula 2. The condensation is preferably performed in the presence of a base such as triethylamine. S-Methylation of this compound affords the 2-methylthio-pyrimidinone of Formula Ia.

For the introduction of the $R^2O$ group, the 2-methylthio bicyclic pyrimidinone of Formula Ia is treated with a mixture of a base, for example sodium hydride, in $R^2OH$ solvent. The reaction mixture is stirred at a temperature from about 0° C. to 120° C. for 1 to 120 hours. The desired 2-$R^2O$ bicyclic pyrimidinone can be isolated from the reaction mixture by extraction into a water-immiscible solvent, and purified by chromatography or recrystallization. Synthetic procedures for the preparation of related 4(3H)-quinazolinones are described in U.S. Pat. No. 3,755,582 and incorporated herein by reference.

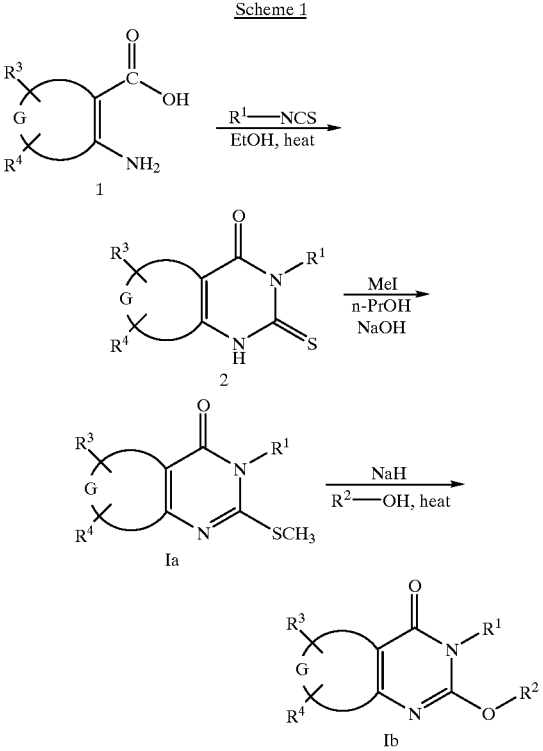

Scheme 1

2-Aminocarboxylic acids of Formula 1 are commercially available or can be prepared by known methods. For example, see *J. Heterocycl. Chem.*, (1966), 3, 252; *J. Org.*

Chem., (1952), 17, 547; *J. Org. Chem.*, (1949), 14, 97; *Synth. Commun.*, (1979), 9, 731. The isothiocyanates of Formula $R^1$-NCS can be prepared from the corresponding amine by treatment with thiophosgene as known in the art. For example, see *J. Heterocycl. Chem.*, (1990), 27, 407.

Alternatively, 2-thiopyrimidinediones of Formula 2 can be prepared by treatment of the ($C_1$–$C_4$ alkyl) carboxylic acid ester of Formula 3 with thiophosgene to form the isothiocyanate ester, followed by treatment with an amine of formula $R^1NH_2$ (Scheme 2).

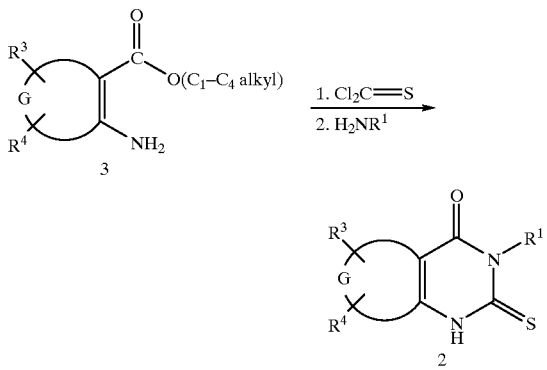

The ester of Formula 3 is treated with thiophosgene at a temperature from about −20 to 100° C. for 1 to 48 hours optionally in an inert solvent. Often this reaction is performed in a biphasic mixture in the presence of a base, such as calcium carbonate, and an acid, such as aqueous hydrochloric acid. The resulting isothiocyanate may be isolated by extraction into a water-immiscible solvent, such as methylene chloride, followed by drying of the organic extracts and evaporation under reduced pressure. Alternatively, the isothiocyanate can be combined in situ with the amine of Formula $H_2NR^1$ and stirred at about −20 to 50° C. for 0.1 to 24 hours. The desired 2-thiopyrimidinedione of Formula 2 can be isolated from the reaction mixture by aqueous extraction, and purified by chromatography or recrystallization. Similar synthetic procedures are described in *J. Heterocycl. Chem.*, (1990), 27, 407.

Pyrimidinones of Formula Ic, compounds of Formula I wherein W is S and Q is O, can be prepared by a modification of the synthesis illustrated in Scheme 1. As illustrated in Scheme 3, the 2-thiopyrimidinedione of Formula 2 is alkylated with $R^2$-X wherein X is a typical leaving group such as Br, I, $CH_3SO_3$ (OMs), or (4—$CH_3$—Ph)$SO_3$ (OTs) to afford the 2-$R^2$S fused pyrimidinone of Formula Ic. One or more equivalents of a base can be used to accelerate the process. Bases such as sodium hydroxide and sodium hydride are suitable.

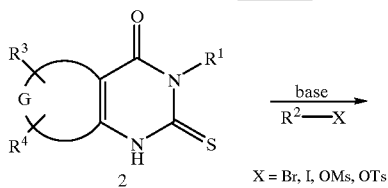

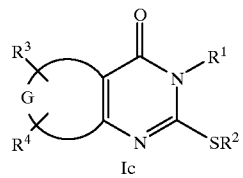

Typically, the 2-thiopyrimidinedione is dissolved or dispersed in an inert solvent such as dimethylformamide and treated with a base at a temperature from about −20 to 60° C. The reaction mixture may then be heated to just above ambient temperature to the reflux temperature of the solvent for 0.1 to 24 hours to effect deprotonation. The reaction mixture is cooled and treated with $R^2$-X and stirred for 0.1–24 hours at a temperature from about 20° C. to the reflux temperature of the solvent. The pyriridinone of Formula Ic can be isolated by extraction into a water-immiscible solvent, and purified by chromatography or recrystallization.

2-Thiopyrimidinediones of Formula 2 are prepared as described above in Schemes 1 and 2.

Fused bicyclic pyrimidinones of Formula Id, compounds of Formula I wherein Q is O and W is S(O) or $S(O)_2$, can be prepared by oxidation of the corresponding —$SR^2$ compound of Formula Ic using well-known procedures for oxidation of sulfur (Scheme 4). For example, see March, J. *Advanced Organic Chemistry*; 3rd ed., John Wiley: New York, (1985), p 1089.

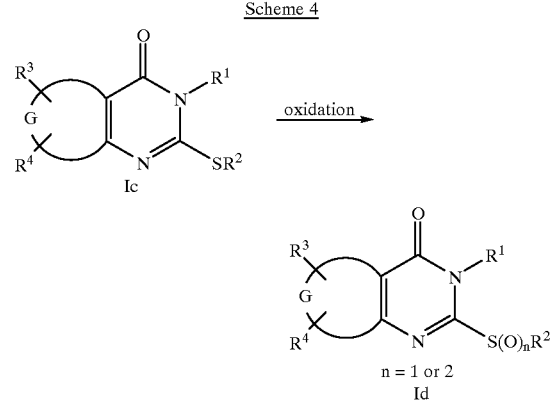

Fused bicyclic pyrimidinones of Formula Ie, compounds of Formula I wherein Q is O and W is $NR^5$, can be prepared by the method illustrated in Scheme 5. This method is described in detail in U.S. Pat. No. 3,867,384 and incorporated herein by reference.

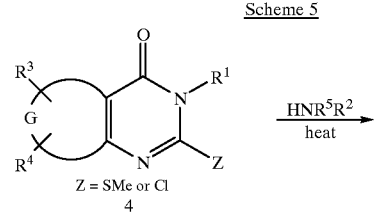

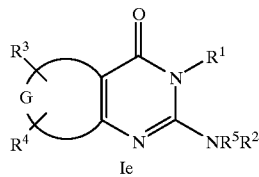

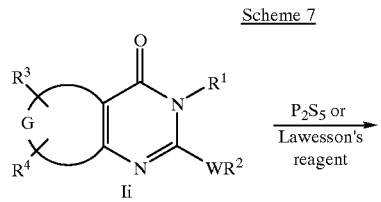

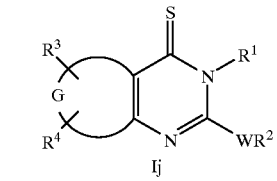

One method of preparation of compounds of Formula Ie is by treatment of a 2-methylthio pyrimidinone of Formula 4 (Z=SMe) with an excess of an amine of Formula $HNR^5R^2$ at about 150 to 175° C. A second method is to contact a 2-chloro-pyrimidinone of Formula 4 (Z=Cl) with one equivalent of $HNR^5R^2$ and one equivalent of an acid scavenger, for example triethylamine, or with two equivalents of $HNR^5R^2$, at a temperature between 60 and 120° C. optionally in the presence of a solvent.

The preparation of compounds of pyrimidinones wherein Z is SMe is described above and in U.S. Pat. No. 3,755,582. The synthesis of pyrimidinones of Formula 4 wherein Z is Cl is described in U.S. Pat. No. 3,867,384. Amines of Formula $HNR^5R^2$ are commercially available or can be prepared by well-known methods (March, J. *Advanced Organic Chemistry*; 3rd ed., John Wiley: New York, (1985), p 1153).

In addition to the methods described above, compounds of Formula Ib and Ic can be prepared by displacement of the 2-chlorine in the appropriate fused pyrimidinone, rather than by displacement of the 2-$SCH_3$ group (Scheme 1) or S-alkylation of the thiocarbonyl (Scheme 3).

In addition to the method described above, pyrimidinones of Formulae Ig and Ih, compounds of Formula I wherein $R^5$=C(=O)$R^{12}$, can be prepared by acylation of the corresponding $R^5$=H compound of Formula If as illustrated in Scheme 6.

Treatment of the fused pyrimidinone of Formula Ii with phosphorous pentasulfide or Lawesson's reagent [2,4-bis(4-methoxyphenyl)-1,3-dithia-2,4-diphosphetane-2,4-disulfide] in an inert solvent such as dioxane at a temperature from 0° C. to the reflux temperature of the solvent for 0.1 to 72 hours affords the pyrimidinethione of Formula Ij. This procedure is described in U.S. Pat. No. 3,755,582 and incorporated herein by reference.

For some compounds of Formula I, the $R^3$ and/or $R^4$ substituent is more conveniently introduced after cyclization to form the fused pyrimidinone. For example, the fused bromo-thiophene compound of Example 1 below was prepared by first synthesizing the fused pyrimidinone ring system, and then introducing the bromine substituent onto the thiophene ring. Other $R^3$ and $R^4$ substituents can be introduced onto the G ring in a similar fashion, or by displacement of a leaving group. For example, displacement of the bromine on the thiophene ring with the appropriate nucleophile can afford the corresponding $R^3$=alkoxy, alkylthio, or $NR^6R^7$ compound.

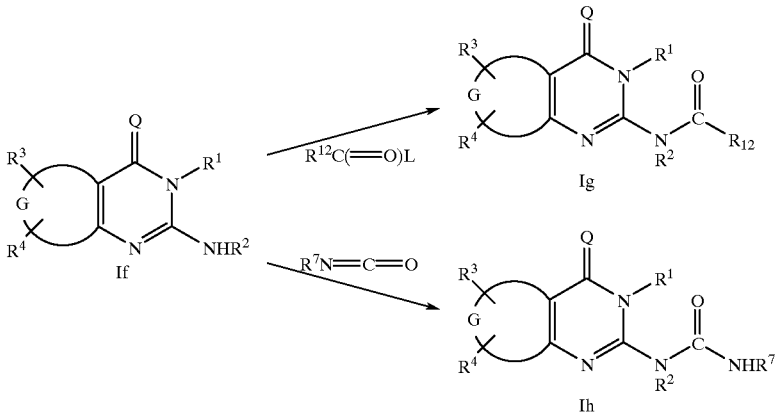

The pyrimidinones of Formula If are treated with an acylating agent of Formula $R^{12}C$(=O)L wherein L is an appropriate leaving group such as chlorine or OC(=O)(H or $C_1$–$C_4$ alkyl). In a similar fashion, compounds of Formula I wherein $R^5$ is —C(=O)$NHR^7$ (Formula Ih) can be prepared by condensing pyrimidinones of Formula If with isocyanates of Formula $R^7N$=C=O using well known procedures.

Compounds of Formula Ij, compounds of Formula I wherein Q is S, can be prepared as illustrated in Scheme 7.

Salts of compounds of Formula I can be formed by treating the free base of the corresponding compound with strong acids such as hydrochloric or sulfuric acid. Salts can also be prepared by alkylation of a tertiary amine group in the molecule to form, for example, the trialkylammonium salt. N-Oxides of compounds of Formula I can be made by oxidizing the corresponding reduced nitrogen compound with a strong oxidizing agent such as meta-chloroperoxybenzoic acid.

Synthesis of $R^{11}$ Groups

As indicated above, compounds of Formula I can be prepared by incorporation of the $R^{11}$ group after the synthesis of the pyrimidinone ring system. A method for preparing the desired $R^{11}$ group is to form the carbocycle or heterocycle from the pyrimidinone wherein $R^1$=alkenyl or alkynyl, or $R^2$=alkenyl or alkynyl. Methods for preparing carbocycles or heterocycles from alkenes and alkynes are well-known in the literature.

The method of incorporating $R^{11}$ into the corresponding alkenyl compound is generically illustrated in Scheme 8. The first reaction illustrates the method for preparing $R^1$=$R^{11}$ compounds from the corresponding $R^1$=alkenyl compound. The second reaction illustrates how the same methodology can be used to prepare the $R^2$=$R^{11}$ compounds.

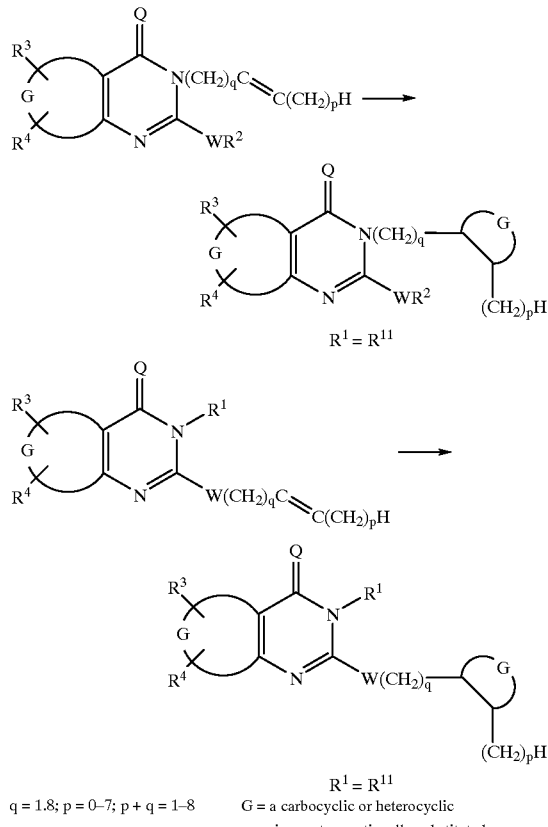

The descriptions below refer to the preparation of the $R^1$=$R^{11}$ compounds, although one skilled in the art recognizes that the same procedures can be used to prepare the $R^2$=$R^{11}$ materials as well. The starting $R^1$ or $R^2$ alkenes are prepared by the methods described above and illustrated in Schemes 1–7.

3-Membered Ring Heterocycles

Compounds of Formula Ik, compounds of Formula I wherein $R^1$ is $R^{11}$ and $R^{11}$ comprises an epoxide, can be prepared as illustrated in Scheme 9.

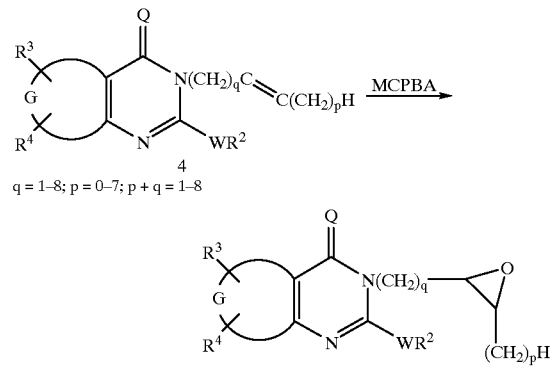

Treatment of the alkene of Formula 4 with an oxidizing agent such as m-chloroperoxybenzoic acid (MCPBA) in an inert solvent such as methylene chloride affords the epoxide of Formula Ik as described by Schwartz, N., in *J. Org. Chem.*, (1964), 29, 1976.

Similarly, the aziridines of Formula Il can be prepared from the alkenes of Formula 4 by condensation with a nitrene as illustrated in Scheme 10 and described in Abramovitch, R. *J. Chem. Soc., Chem. Commun.*, (1972), 1160.

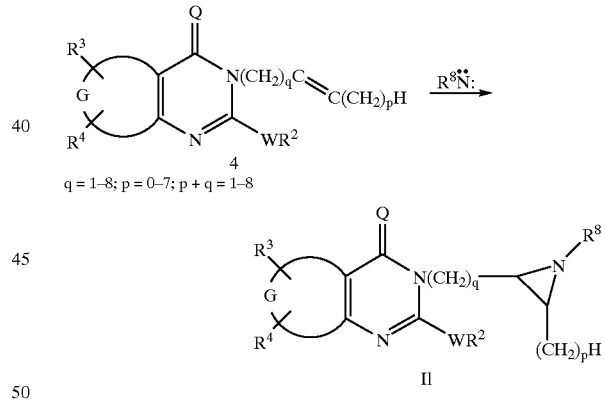

The NH aziridine compound of Formula Im can be prepared from the corresponding epoxide by contact with sodium azide and triphenylphosphine as illustrated below in Scheme 11 and described by Ittah, Y. in *J. Org. Chem.*, (1978), 43, 4271. The episulfide of Formula In can also be prepared from the epoxide using triphenylphosphine sulfide using techniques taught by Chan, T. in *J. Am. Chem. Soc.*, (1972), 94, 2880.

Scheme 11

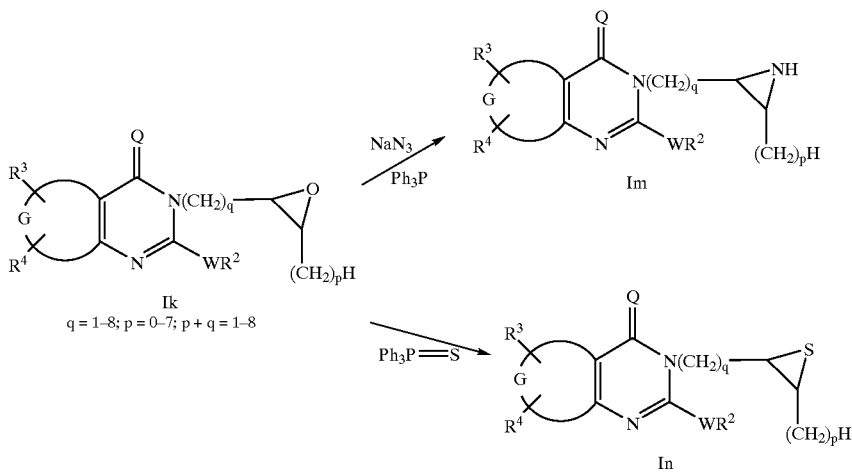

In addition to the methods described above, methods for accessing compounds of Formulae Ik–In are taught in Calo, V., *J. Chem. Soc., Chem. Commun.*, (1975), 621; Fujisawa, T., *Chem. Lett.*, (1972), 935; and March, J. *Advanced Organic Chemistry*; 3rd ed., John Wiley: New York, (1985), p 741.

4-Membered Ring Heterocycles

The synthesis of oxetanes of Formula Io may be achieved by ring expansion of the corresponding epoxide using dimethyloxosulfonium methylide as illustrated in Scheme 12 and described by J. Okuma in *J. Org. Chem.*, (1983), 48, 5133. In some cases, a mixture of regioisomers will be obtained. Additional methods for preparing oxetanes, as well as other 4-membered ring heterocycles, from an alkene precursor are well-known in the art. For example, see: Buchi, G., *J. Am. Chem. Soc.*, (1954), 76, 4327; and Pifferi, G., *J. Heterocyclic Chem.*, (1967), 4, 619.

Scheme 12

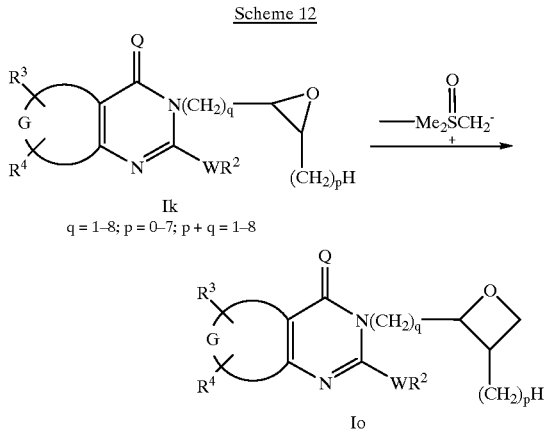

5-Membered Ring Heterocycles

Compounds of Formula I wherein $R^{11}$ comprises a 5-membered ring heterocycle can be obtained in a variety of ways. For example, dioxolane compounds can be prepared from the glycol using known methods. A method exemplifying the preparation of the dimethyl-dioxolane is illustrated in Scheme 13 and described by A. Hampton in *J. Am. Chem. Soc.*, (1961), 83, 3640.

Scheme 13

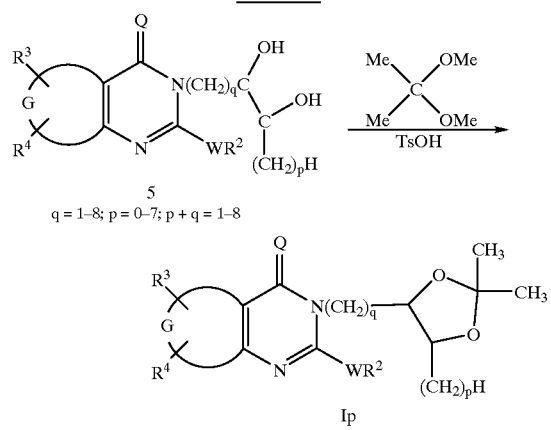

Reaction of the glycol of Formula 5 with p-toluenesulfonic acid (TsOH) and 2,2-dimethoxypropane provides the desired material. The glycol of Formula 5 can be prepared from the alkene of Formula 4 using vicinal bis-hydroxylation reagents such as osmium tetroxide (see Wade, P., *Tetrahedron Lett.*, (1989), 5969).

Some 5-membered ring compounds can be prepared from the alkene of Formula 4 using a 1,3-dipole cyclization. For example, reaction of 4 with bromonitrile oxide produces the dihydroisoxazole of Formula Iq as illustrated in Scheme 14 (see Wade, P., in *J. Org. Chem.*, (1990), 55, 3045).

Scheme 14

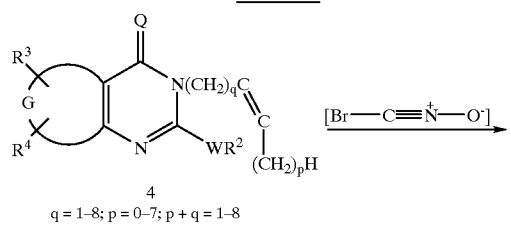

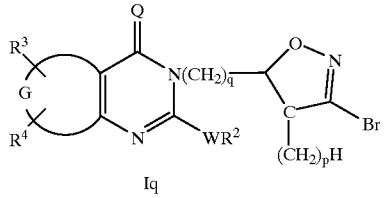

Iq

Cycloaddition of 1,3-dipoles with alkynes are also well-documented in the literature. For example, C. Kashima in *Heterocycles*, (1979), 12, 1343 teaches the condensation of an alkyne with benzene nitrile oxide to form the isoxazole. A similar process to prepare the isoxazole of Formula Ir is illustrated in Scheme 15.

Scheme 15

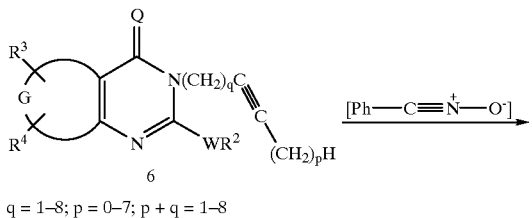

$q = 1-8; p = 0-7; p + q = 1-8$

[Ph—C≡N⁺—O⁻]

Ir

Many 1,3-dipoles are known to react with alkenes and alkynes of Formulae 4 and 6, respectively, in cycloaddition reactions. Dipoles and methods for generating them are described in 1,3-*Dipolar Cycloaddition Reactions*, A. Padwa, Ed., Wiley Interscience, N.Y., 1984, Vols. 1 and 2; and *Comprehensive Heterocyclic Chemistry*, Katritzky, A., Ed., Pergamon, N.Y., 1984, Vol. 5, p 143). Examples of known 1,3 dipoles are nitrile ylides, nitrile imines, nitrile sulfides, diazoalkanes, azides, azomethine ylides and nitrones.

One skilled in the art will recognize that the regiochemical outcome of the 1,3-dipolar addition will depend on the structures of both the 1,3-dipole and the dipolarophile. In many instances, a mixture of regioisomers will be obtained which can be separated by chromatography or recrystallization.

6-Membered Ring Heterocycles

Compounds of Formula I wherein $R^{11}$ comprises a 6-membered ring heterocycle can be prepared from the alkene of Formula 4 by [4+2] cycloaddition with a suitable heterodiene. For example, conditions similar to those described by Krespan, C., in *J. Am. Chem. Soc.*, (1960), 82, 1515, can be employed to form dithianes of Formula Is as illustrated in Scheme 16.

Scheme 16

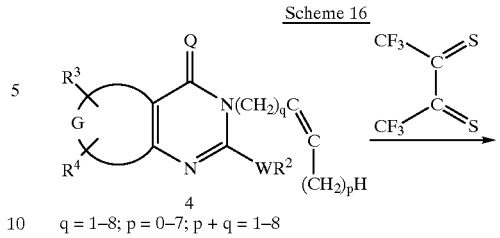

4
$q = 1-8; p = 0-7; p + q = 1-8$

Is

As with the aforementioned 1,3-dipolar cycloadditions, alkynes can also engage in reactions with heterodiene systems to afford unsaturated ring compounds such as those of Formula It.

Scheme 17

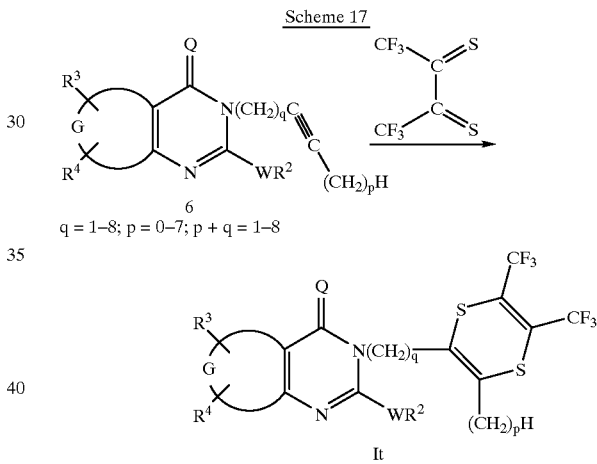

6
$q = 1-8; p = 0-7; p + q = 1-8$

It

Ample literature exists citing various other heterodiene systems which are known to engage alkenes and alkynes of Formulae 4 and 6, respectively, to deliver 6-membered ring heterocyclic adducts. For example, see *Hetero Diels-Alder Methodology in Organic Synthesis*, Boger, D. and Weinreb, S., Eds., Academic, N.Y., (1987), pp 167–357; and *Contemporary Heterocyclic Chemistry*, Newkome, G. and Paudler, W., Wiley Interscience, N.Y., (1982), p 129. Examples of heterodienes known to undergo cycloaddition reactions are thiophene, furan, α,β-unsaturated aldehydes and ketones, α,β-unsaturated thiocarbonyl compounds, α,β-unsaturated imines, vinyl nitroso species, azoalkenes, acyldimides, acyl sulfenes, o-quinones, and thioamide-N-methylium salts.

Again, as in the previously mentioned case of 1,3-dipole cycloadditions, the regiochemical course of the [4+2] condensation depends on the structure of the alkene or alkyne and the heterodiene. Both regioisomers are often obtained in which case the desired regioisomer can be isolated by chromatography or recrystallization.

It is recognized that some reagents and reaction conditions described above for preparing compounds of Formula I may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula I. One skilled in the art will also recognize that it may be necessary to perform a combination of the steps illustrated in the above schemes in an order other than that implied by the particular sequence presented to prepare the compounds of Formula I.

One skilled in the art will also recognize that compounds of Formula I and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; s=singlet, d=doublet, t=triplet, m=multiplet, dd=doublet of doublets, br s=broad singlet.

EXAMPLE 1

Step A: Preparation of 2,3-dihydro-3-propyl-2-thioxothieno[3,2-d]pyrimidin-4(1H)-one To a suspension of 150 mL of ethanol containing 9.5 g of methyl 3-amino-2-thiophenecarboxylate was added dropwise 9.3 mL of n-propyl isothiocyanate with stirring. To this reaction mixture was added 12.64 mL of triethylamine. The reaction mixture was heated at reflux for 3 h, allowed to cool to room temperature and then stirred for approximately 24 h. The mixture was then heated at reflux for an additional 32 h, cooled to approximately 5° C. and filtered to obtain 5.5 g of the title compound of Step A as an off-white solid melting at 246–249° C.

Step B: Preparation of 2-(methylthio)-3-propylthieno[3,2-d]pyrimidin4(3H)-one

To a mixture containing 3.6 g of the title compound of Step A suspended in 70 mL of 10% propanolic sodium hydroxide was added 1.46 mL of iodomethane with stirring. The mixture was stirred at room temperature for 1 h, then cooled to 0° C. and filtered to obtain an off-white solid. The off-white solid was purified by partially dissolving it in methylene chloride, filtering and evaporating the filtrate to obtain 3.13 g of the title compound of Step B as a white solid melting at 136–138° C.

Step C: Preparation of 7-bromo-2-(methylthio)-3-propylthieno[3,2-d]pyrimidin-4(3H)-one To a solution containing 1.01 g of the title compound of Step B dissolved in approximately 50 mL of acetic acid cooled to 0° C. was added 0.24 mL of bromine. The mixture was allowed to warm to room temperature and stirred for 24 h. The reaction mixture was filtered to obtain 0.60 g of a white solid. The white solid was purified by column chromatography on silica gel eluting with hexane and then 8:1 hexane:ethyl acetate. Collection and evaporation of those fractions containing the least polar component (according to thin layer chromatography, 6:1 hexane:ethyl acetate mixture as the development solvent) yielded 0.12 g of the title compound of Step C, a compound of the invention, as a white solid melting at 146–147° C. $^1$H NMR (400 MHz, CDCl$_3$): δ 1.02 (t,3H), 1.81 (m,2H), 2.71 (s,3H), 4.11 (t,2H), 7.69 (s,1H).

EXAMPLE 2

Step A: Preparation of 2-amino-5-bromo-3-pyridinecarboxylic acid hydrobromide

A mixture of 3.6 g 2-amino-nicotinic acid in 450 mL of glacial acetic acid was treated with a solution of 4 mL of bromine in 50 mL of glacial acetic acid over 10–15 min. The resulting mixture was stirred at room temperature for 2 h, diluted with 2 L of diethyl ether, and the ensuing precipitate was filtered and dried to provide 6.1 g of the title compound of Step A as a solid melting at 280° C. (decompose) (lit[1]. m.p. 280° C., decomposed). $^1$H NMR (400 MHz, Me$_2$SO-d$_6$): δ 7.38 (br s,2H), 8.08 (s,1H), 8.25 (s,1H), 13.45 (br s,1H). ([1] U.S. Pat. No. 3,950,160)

Step B: Preparation of 6-bromo-2,3-dihydro-3-propyl-2-thioxopyrido[2,3-d]pyrimidin4(1H)-one A mixture of n-propyl isothiocyanate (1.59 g, 1.62 mL), triethylamine (5.0 g, 13.8 mL), and 5.0 g of the title compound of Step A was heated to 100–110° C. in 22 mL of dimethylformamide for 48 h. The reaction mixture was then allowed to cool to room temperature and treated with 10 mL of ethanol. The resulting precipitate was filtered, washed with ethanol followed by hexanes and dried to deliver 2.48 g of the title compound of Step B. $^1$H NMR (400 MHz, Me$_2$SO-d$_6$): δ 0.90 (t,3H), 1.60–1.78 (m,2H), 4.30 (t,2H), 8.41 (s,1H), 8.82 (s,1H), 13.55 (s,1H).

Step C: Preparation of 6-bromo-2-(methylthio)-3-propylpyrido[2,3-d]pyrimidin-4(3H)-one A mixture of iodomethane (1.33 g, 0.58 mL), 8.7 g potassium carbonate and 1.88 g of the title compound of Step B was stirred at room temperature in 50 mL of dimethylformamide for 3 h. A 1 mL portion of saturated aqueous NaHCO$_3$ was added and the reaction mixture was concentrated to dryness under reduced pressure. The resulting residue was partitioned between 200 mL each of methylene chloride and water, and the organic layer was removed. Further washing of the organic phase with water and saturated aqueous NaCl followed by drying (Na$_2$SO$_4$) and concentration under reduced pressure delivered 1.8 g of the crude product. This material was then subjected to silica gel chromatography using 70:30 hexane:ethyl acetate as eluant to afford 1.48 g of the title compound of Step C, a compound of the invention, as a white solid melting at 124–127° C. $^1$H NMR (400 MHz, CDCl$_3$): δ 1.03 (t,3H), 1.76–1.90 (m,2H), 2.7 (s,3H), 4.1 (t,2H), 8.63 (s,1H), 8.89 (s,1H).

EXAMPLE 3

Preparation of 6-bromo-2-propoxv-3-propylpyrido[2,3-d]pyrimidin4(3H)-one

To 8 mL of n-propanol at 0° C. was added 0.06 g of sodium hydride (60% active in oil). The resulting mixture was then stirred at room temperature for 30 min, at which time 0.5 g of the title compound of Step C in Example 2 was added. The mixture was heated at reflux for 3 h. The reaction mixture was then allowed to cool to room temperature, treated with 1 mL of saturated aqueous sodium bicarbonate, and then concentrated to dryness under reduced pressure. The residue so obtained was partitioned between 100 mL each of methylene chloride and water, and the organic layer was removed. The organic layer was washed with water and saturated aqueous NaCl, dried (Na₂SO₄), and concentrated under reduced pressure until a precipitate formed. The resulting mixture was filtered and the residue was rinsed with a few milliliters of methylene chloride. The collected filtrate was evaporated to dryness, and the residue was purified by flash chromatography on silica gel (8:2 hexane-:ethyl acetate as the eluant) to give 0.175 g of the title compound of Example 3, a compound of the invention, as a solid melting at 100–103° C. $^1$H NMR (400 MHz, CDCl₃): δ 0.99 (t,3H), 1.07 (t,3H), 1.64–1.80 (m,2H), 1.80–1.95 (m,2H), 4.05 (t,2H), 4.56 (t,2H), 8.60 (s,1H), 8.83 (d,1H).

EXAMPLE 4

Step A: Preparation of 2,3-dihydro-3-propyl-2-thioxobenzo[g]quinazolin-4(1H)-one To a suspension of 1.88 g of 3-amnino-2-naphthalic acid in 25 mnL of 2-propanol was added 1.39 mL of triethylamine followed by 1.02 g of n-propyl isothiocyanate with stirring. The mixture was heated at reflux for 2 h, and then allowed to cool to room temperature. The resulting solid was collected by filtration and washed with cold 2-propanol to give 1.97 g of the title compound of Step A as a yellow solid.

Step B: Preparation of 2-(methylthio)-3-propylbenzo[g]quinazolin4(3H)-one

Sodium hydride (60% active in oil, 0.67 g) was washed with petroleum ether twice. To the washed sodium hydride was added 40 mL of 1-propanol followed by 1.5 g of the title compound of Step A and then 0.42 mL of iodomethane. The resulting suspension was stirred at room temperature for 4.5 h. To this suspension was added 100 mL of water and 50 mL of ether. The insoluble solid was filtered-off to give 1.06 g of the title compound of Step B, a compound of the invention, as a yellow solid melting at 143–145° C. The ether layer of the filtrate was separated and the aqueous layer was extracted with ethyl acetate (2 times with 50 mL). The three organic portions were combined, washed with 80 mL of water and 80 mL of saturated aqueous NaCl, dried (MgSO₄) and concentrated under reduced pressure to give an additional 0.47 g of the title compound of Step B as a yellow solid.

EXAMPLE 5

Preparation of 2-propoxy-3-propylbenzo[g]quinazolin-4(3H)-one

To 45 mL of 1-propanol was added 0.15 g of sodium hydride (60% active in oil) at room temperature. After the gas evolution ceased, 0.9 g of the title compound of Step B in Example 4 was added. The resulting yellow suspension was stirred at room temperature overnight. To the reaction mixture was added 0.15 g of sodium hydride and the mixture was heated at 70–80° C. for 4 h and then was stirred at room temperature over the weekend. The reaction mixture was heated for 2 h at 70–80° C. and then cooled to room temperature. The reaction mixture was then mixed with 150 mL of water and the resulting mixture was extracted with ether (2 times with 100 mL). The organic portions were combined, washed with water (2 times with 150 mL), dried (MgSO₄) and concentrated to give 1.01 g of a solid. Purification by column chromatography on silica gel eluting with 5% v/v ethyl acetate in hexane afforded 0.75 g of the title compound of Example 5, a compound of the invention, as a white solid melting at 76–79.5° C. $^1$H NMR (400 MHz, CDCl₃):δ8 8.81 (s,1H), 7.99 (d,1H), 7.92 (s,1H), 7.88 (d,1H), 7.54 (m,1H), 7.44 (m,1H), 4.49 (t,2H), 4.10 (m,2H), 1.88 (m,2H), 1.76 (m,2H), 1.09 (t,3H), 1.00 (t,3H).

EXAMPLE 6

Step A: Preparation of 6-bromo-2.3-dihydro-3-[(tetrahydro-2-furanyl)methyl]-2-thioxo-4(1H)-quinazolinone A mixture of 2-amino-5-bromobenzoic acid (8.0 g, 37.0 mmol), tetrahydrofurfuryl isothiocyanate (5.0 g, 34.9 mmol) and triethylarine (5.0 mL, 3.6 g, 35.6 mmol) in ethanol (48 mL) was heated at reflux for 2 h. The reaction mixture was then allowed to cool to room temperature and filtered. The resulting filter cake was washed with 50 mL of cold ethanol, followed by 50 mL of hexanes to provide 10.8 g of the title compound of Step A as a solid melting at 230–232° C. IH NMR (400 MHz, Me₂SO-d₆): δ 1.63–2.0 (m,4H), 3.58–3.68 (m,1H), 3.74–3.82 (m,1H), 4.32 (dd,1H), 4.39–4.50 (m,1H), 4.58 (dd,1H), 7.37 (d,1H), 7.91 (d,1H), 8.02 (s,1H), 13.1 (br s,1H).

Step B: Preparation of 6-bromo-2-(methylthio)-3-[(tetrahydro-2-furanyl)methyl]-4(3H)-quinazolinone Potassium carbonate (6.0 g, 44 mmol), iodomethane (2.5 g, 1.1 mL, 17.6 mmol), and the title compound of Step A (3.0 g, 8.8 mmol) were combined in dimethylformamide (90 mL) and stirred for 2 h at room temperature. The reaction mixture was then concentrated to dryness under reduced pressure, and the ensuing residue was partitioned between 200 mL each of ethyl acetate and water. The phases were separated and the organic phase was subsequently washed with saturated aqueous NaCl and dried over Na₂SO₄ (anhydrous). Following solvent removal under reduced pressure and trituration of the resulting material with cold hexanes, 2.8 g of the title compound of Step B, a compound of the invention, was obtained as a solid melting at 68–72° C. $^1$H NMR (300 MHz, CDCl₃):δ6 1.64–1.83 (m,1H), 1.80–2.18 (m,3H), 2.62 (s,3H), 3.78 (dd,1H), 3.96 (dd,1H), 4.17 (dd, 1H), 4.21 (dd,1H), 4.38–4.50 (m,1H), 7.41 (d,1H), 7.73 (dd,1H), 8.36 (d,1H).

EXAMPLE 7

Preparation of 6-bromo-2-propoxy-3-[(tetrahydro-2-furanyl)methyl]-4(3H)-quinazolinone A solution of 1-propanol (0.68 g, 11.2 mmol) in dimethylformamide (25 mL) was treated with 0.45 g of sodium hydride (60% active in oil) and stirred for 30 min at room temperature. After brief, gentle heating to ensure complete propoxide formation, the reaction mixture was allowed to cool to room temperature and treated with 2.0 g (5.6 mmol) of the title compound of Step B in Example 6. The resulting mixture was stirred at room temperature for 3 h, and then was quenched with 1 mL of saturated aqueous sodium hydrogen carbonate. Following concentration to dryness under reduced pressure, the reaction residue was partitioned between 200 mL each of ethyl acetate and water. The organic phase was separated, washed with saturated aqueous NaCl, and dried over Na₂SO₄ (anhydrous). Concentration under reduced pressure provided 1.5 g of the crude product. Purification was accomplished by column chromatography on silica gel using 70:30 v/v hexane:ethyl acetate, followed by ethyl acetate, as eluants. Collection and evaporation of those fractions containing only the least polar component (according to thin-layer chromatography employing a 70:30 v/v mixture of hexane:ethyl acetate as eluant) delivered 0.65 g of the title compound of Example 7, a compound of the invention, as a solid melting at 83–85° C. $^1$H NMR (400 MHz, CDCl₃): δ 1.07 (t,3H), 1.64–1.80 (m,1H), 1.80–1.90 (m,2H), 1.86–1.96 (m,1H), 1.97–2.08 (m,2H), 3.78 (dd,1H), 3.9 (dd,1H), 4.07 (dd,1H), 4.21 (dd,1H), 4.3–4.4 (m,1H), 4.42 (t,2H), 7.33 (d,1H), 7.70 (dd,1H), 8.30 (d,1H).

EXAMPLE 8
Preparation of 6-bromo-3-(oxiranylmethyl)-2-propoxy-4 (3H)-quinazolinone A mixture of 1.45 g of 3-chloroperoxybenzoic acid (50–60% by weight, delivers 4.6 mmol) and 0.50 g (1.5 mmol) of 6-bromo-3-(2-propenyl)-2-propoxy-4(3H)-quinazolinone was stirred at room temperature for 24 h. (Note: 6-Bromo-3-(2-propenyl)-2-propoxy-4(3H)-quinazolinone was prepared from 2-amino-5-bromobenzoic acid and allyl isothiocyanate via methods described in Examples 6 and 7, with the exception that 1-propanol was used as the reaction solvent in the method described in Example 7 rather than dimethylformamide.) Following the addition of 3 mL of saturated aqueous sodium hydrogen sulfite, the reaction mixture was partitioned between 100 mL each of methylene chloride and water. The organic phase was removed and successively washed with 100 mL each of 15% aqueous potassium carbonate, water, and saturated aqueous NaCl. Drying over $Na_2SO_4$ (anhydrous) and evaporation under reduced pressure afforded 0.55 g of the crude product as an oil. The crude material was subjected to column chromatography on silica gel using 90:10 v/v hexane:ethyl acetate as eluant. Collection and concentration of those fractions containing only the more polar component of the crude material (according to thin-layer chromatography using 80:20 v/v hexane:ethyl acetate as developing solvent) provided 0.087 g of the title compound of Example 8, a compound of the invention, as a solid melting at 84–87° C. $^1$H NMR (400 MHz, $CDCl_3$):δ1.04 (t,3H), 1.8–1.9 (m,2H), 2.45–2.50 (m,1H), 2.58–2.61 (m,1H), 3.27 (m,1H), 4.25 (dd,1H), 4.36 (dd,1H), 4.45 (t,2H), 7.35 (d,1H), 7.72 (d,1H), 8.30 (s,1H).

EXAMPLE 9
Preparation of ethyl 5-[(6-bromo-3,4-dihdro-4-oxo-2-propoxy-3-quinoxalinylmethyl]-4,5-dihydro-3-isoxazolecarboxylate A mixture of 6-bromo-3-(2-propenyl)-2-propoxy-4(3H)-quinazolinone (3.3 g, 11.0 mmol) and potassium carbonate (42.9 g, 311 mmol) in 183 mL of tetrahydrofuran (THF) at 55° C. was treated dropwise over a 1 h period with a solution of ethyl chlorooximidoacetate (5.0 g, 33.1 mmol) in 73 mL of THF. After stirring at 55° C. for two additional hours, heating was discontinued and the reaction mixture was allowed to stir at room temperature overnight. The reaction mixture was then filtered and the filter cake was washed twice with 100 mL portions of methylene chloride. The resulting filtrate was partitioned between 200 mL each of ethyl acetate and water. Separation of the organic phase followed by drying over $Na_2SO_4$ (anhydrous) and concentration under reduced pressure delivered 4.0 g of the crude product. The crude product was triturated with 90:10 v/v hexane:ethyl acetate and filtered to afford 2.0 g of the title compound of Example 9, a compound of the invention, as a solid melting at 139–141° C. $^1$H NMR (300 MHz, $CDCl_3$): δ 1.04 (t,3H), 1.39 (t,3H), 1.8–1.92 (m,2H), 3.18 (dd,1H), 3.24 (dd,1H), 4.23–4.35 (m,2H), 4.38 (d,2H), 4.44 (t,2H), 5.1–5.25 (m,1H), 7.37 (d,1H), (dd,1H), 8.3(d,1H).

EXAMPLE 10
Preparation of 6-bromo-3-propyl-2-(3-pyridinylmethoxy)4 (3)-quinazolinone A 0.06 g portion of sodium hydride (60% active in oil, delivers 1.6 mmol NaH) was added to 8 mL of 3-pyridinylcarbinol at 0° C. and the resulting mixture was stirred at 0° C. for 15 min. Cooling was ceased and the mixture was then stirred at room temperature for 1 h followed by a brief period of gentle heating to ensure complete alkoxide formation. After cooling back to ambient temperature, 6-bromo-2-(methylthio)-3-propyl-4(3H)-quinazolinone (0.50 g, 1.6 mmol, prepared from n-propyl isothiocyanate via methods described in Example 6 with exception that triethylamine was omitted in Step A) was added all at once and the ensuing mixture was stirred at room temperature for 48 h. Upon partitioning between 150 mL each of ethyl acetate and water, the organic layer was removed. The organic layer was washed once with 100 mL of saturated aqueous NaCl and dried over anhydrous $Na_2SO_4$. Concentration to dryness under reduced pressure gave 3.6 g of an oil. Subjection of this crude residue to column chromatography on silica gel (6:4 v/v hexane:ethyl acetate as eluant) provided three fractions of partially purified materials as oils after solvent removal. Treatment of the intermediate fraction with several milliliters of water with swirling resulted in formation of a precipitate. Filtration of the precipitate followed by washing with several milliliters of hexane and drying afforded 0.266 g of the title compound of Example 10, a compound of the invention, as a solid melting at 120–124° C. $^1$H NMR (400 MHz, $CDCl_3$): δ 0.95 (t,3H), 1.60–1.78 (m,2H), 4.04 (t,2H), 5.58 (s,2H), 7.38 (d,1H), on 7.36 (t,1H), 7.71 (d,1H), 7.8 (d,1H), 8.3 (s,1H), 8.62 (d,1H), 8.78 (s,1H).

EXAMPLE 11
Step A: Preparation of 3-(cyclopropylmethyl)-2.3-dihydro-6-iodo-2-thioxopyrido[2,3-d] pyrimidin4(1H)-one A mixture of 2-amino-nicotinic acid (5 g, 36.2 mmol) in glacial acetic acid at 80° C. was treated dropwise with iodine monochloride (17.5 g, 108 mmol) in 100 mL glacial acetic acid over a ten-minute period. The resulting mixture was heated at 80° C. for 3 h, followed by stirring at ambient temperature overnight. The reaction mixture was added to 2000 mL hexanes/500 mL $Et_2O$ and stirred at ambient temperature overnight. The resulting precipitate was filtered, washed with $Et_2O$ and dried to provide 8.5 g of a solid melting at 251–254° C. A 2.5 g quantity of this material was combined with cyclopropyl methylisothiocyanate (0.88 g, 7.8 mmol) and triethylamine (25 g, 25.0 mmol) in dimethylformamide (20 mL) and heated to 110–120° C. for about 3 days. The reaction mixture was diluted with an equal volume of ethanol and filtered to afford a solid. The filtrate was refiltered to deliver a second crop of solid. The filtered precipitates so obtained were then combined and washed with additional ethanol, followed by hexane washing. After drying, 0.53 g of the title compound of Step A was obtained as a solid melting at <300° C. $^1$H-NMR (300 MHz, $Me_2SO$-$d_6$): δ 0.38–0.50 (m,4H), 1.30–1.47 (m,1H), 4.24–4.40 (d,2H), 8.58 (d,1H), 8.92 (s,1H), 13.50 (br s,1H).

Step B: Preparation of 3-(cyclopropylmethyl)-6-iodo-2-(propylthio)pyrido[2,3-d]pyrimidin-4(3H)-one A mixture of the title compound of Step A (0.5 g, 1.39 mmol), n-propyl iodide (0.36 g, 2.09 mmol) and potassium carbonate (1.9 g, 13.9 mmol) in DMF (14 mL) were stirred at ambient temperature overnight. The reaction mixture was then concentrated to dryness in vacuo and the residue partitioned between 200 mL of ethyl acetate and 100 mL of $H_2O$. The organic phase was separated, washed with saturated aqueous NaCl, dried over $Na_2SO_4$ and concentrated in vacuo to provide 0.5 g of crude product. Purification of this crude product was achieved via column chromatography (silica gel, 70:30 hexanes:ethyl acetate eluent) to deliver 0.19 g of the title compound of Step B, a compound of the invention, as a solid melting at 159–161° C. $^1$H NMR (300 MHz, $CDCl_3$): δ 0.50–0.62 (m,4H), 1.10 (t,3H), 1.31–1.43 (m,1H), 1.79–1.94 (m,2H), 3.41 (t,2H), 4.10 (d,2H), 8.82 (s,1H), 9.02 (d, 1H). Mass Spectrum: m/e 402 (protonated parent molecular ion measured by mass spectrometry using atmospheric pressure chemical ionization in the positive ion mode ($APCI^+$); the ion shown corresponds to the $M+H^+$ ion calculated from the integral values of the atomic weights of the most abundant isotope of each element present).

EXAMPLE 12

Step A: Preparation of 2.3-dihydro-6.8-diiodo-3-[(tetrahydro-2-furanyl)methyl]-2-thioxo-4(1H) quinazolinone A mixture of 2-amino-3,5-diiodobenzoic acid (1.09 g, 2.57 mmol), tetrahydrofurfuryl isothiocyanate (0.35 g, 2.43 mmol) and triethylamine (0.26 g, 2.57 mmol) in 3.5 mL of ethanol was heated to reflux for about 6 h, and then was allowed to cool to room temperature. The ensuing precipitate was filtered and washed with ethanol (1×20 mL), hexanes (1×mL), and then dried to deliver 0.86 g of the title compound of Step A. $^1$H NMR (400 MHz, Me$_2$SO-d$_6$): δ 1.64–1.75 (m,1H), 1.75–1.85 (m,1H), 1.86–2.0 (m,2H), 3.57–3.65 (m,1H), 3.70–3.81 (m,1H), 4.26–4.34 (m,1H), 4.36–4.44 (m,1H), 4.52–4.60 (m,1H), 8.19 (d,1H), 8.56 (d,1H), 10.1 (br s,1H).

Step B: Preparation of 6.8-diiodo-2-(propylthio)-3-[(tetrahydro-2-furanyl)methyl]4(3H)-quinazolinone A mixture of the title compound of Step A (0.86 g, 1.67 mmol), n-propyl iodide (0.85 g, 5.02 mmol) and potassium carbonate (2.3 g, 16.7 mmol) was stirred in dimethylformamide (20 mL) at ambient temperature for approximately 4 h. The reaction mixture was then concentrated to dryness in vacuo and partitioned between 200 mL each of ethyl acetate and water. The organic phase was then separated, washed with saturated aqueous NaCl, and dried over Na$_2$SO$_4$. Concentration in vacuo provided 0.82 g of the title compound of Step B, a compound of the invention, as a solid melting at 108–111° C. $^1$H NMR (300 MHz, CDCl$_3$): δ 1.10 (t,3H), 1.63–1.80 (m,1H), 1.80–2.14 (m,5H), 3.24–3.45 (m,2H), 3.70–3.80 (m,1H), 3.90–4.00 (m,1H), 4.10–4.21 (m,2H), 4.35–4.47 (m,1H), 8.44 (d,1H), 8.48 (d,1H).

By the procedures described herein together with methods known in the art, the following compounds of Tables 1 to 12 can be prepared. The following abbreviations are used in the Tables which follow: t=tertiary, s=secondary, n=normal, i=iso, c=cyclo, Me=methyl, Et=ethyl, Pr=propyl, i-Pr=isopropyl, Bu=butyl, Ph=phenyl, MeO=methoxy, PhO=phenoxy, MeS=methylthio, CN=cyano, NO$_2$=nitro, Me$_3$Si and SiMe$_3$=trimethylsilyl, Me$_2$N=dimethylamino, EtNH=ethylamino, S(O)$_2$Me=methylsulfonyl, and 2-THF=tetrahydro-2-furanyl.

The G groups in the Tables which follow are illustrated. The wavy line indicates that the G ring is fused to the pyrimidinone ring as illustrated below.

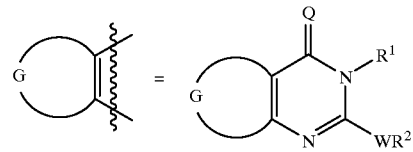

$R^{11}$ is defined in the Summary of the Invention as $C_1$–$C_{10}$ alkyl substituted with a carbobicyclic, heterobicyclic or heteromonocyclic ring optionally substituted with $R^8$, $R^9$ and $R^{10}$. In Tables 1–4 below, $R^{11}$ is represented by an alkylene chain [e.g., $(CH_2)_3$], and the carbobicyclic, heterobicyclic or heteromonocyclic ring substituent is indicated by a Y-number corresponding to the Y groups illustrated in Exhibit 1 above.

Therefore, for example, the Table entry of $R^{11}$=CH$_2$(Y-2), $R^8$=3-OCF$_3$ represents:

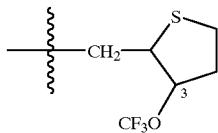

The numbering system for the ring portion of $R^{11}$ is indicated in Exhibit 1. A dash ("-") indicates $R^8$, $R^9$ and/or $R^{10}$ is not present. An unsubstituted ring (i.e., a ring bearing only hydrogens) has a "-" for $R^8$, $R^9$ and $R^{10}$.

TABLE 1

Compounds of Formula I wherein Q is O, $R^1$ = $R^2$ = n-propyl, W is O,

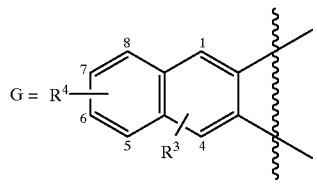

| $R^3$ | $R^4$ | $R^3$ | $R^4$ | $R^3$ | $R^4$ |
|---|---|---|---|---|---|
| 7-Br | H | 8-I | 4-I | 8-I | H |
| 7-Cl | H | 7-C≡CH | H | 7-CH=CH$_2$ | H |
| 7-I | H | 7-C≡CSiMe$_3$ | H | 6-I | H |
| 7-I | 5-I | H | H | 8-Br | H |
| 7-Br | 5-Br | 7-CF$_3$ | H | 7-Br | 4-Br |
| 7-I | 4-I | 4-Br | H | 4-I | H |

TABLE 1-continued

Compounds of Formula I wherein Q is O, $R^1 = R^2$ = n-propyl, W is O,

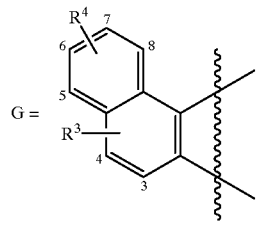

G =

| $R^3$ | $R^4$ | $R^3$ | $R^4$ | $R^3$ | $R^4$ |
|---|---|---|---|---|---|
| 7-Br | H | 7-I | 5-I | 8-I | H |
| 7-Cl | H | 7-C≡CH | H | 7-CH=CH$_2$ | H |
| 7-I | H | 7-C≡CH | 5-Br | 7-Br | 5-Me |
| 7-Cl | 5-Cl | H | H | 5-Br | H |
| 7-Br | 5-Br | 7-CF$_3$ | H | 7-Br | 3-Br |
| 7-I | 4-I | 4-Br | H | 4-I | H |

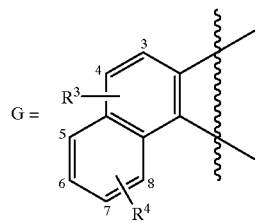

G =

| $R^3$ | $R^4$ | $R^3$ | $R^4$ | $R^3$ | $R^4$ |
|---|---|---|---|---|---|
| 5-Br | H | 4-I | H | 8-I | H |
| 5-Cl | H | 7-C≡CH | H | 4-CH=CH$_2$ | H |
| 5-I | H | 7-C≡CSiMe$_3$ | 5-Br | 4-Br | 5-Me |
| 5-I | 6-I | H | H | 4-Br | 8-I |
| 4-Br | 5-Br | 4-Br | H | 7-Br | 3-Br |
| 4-I | 5-I | 5-Br | 8-Br | | |

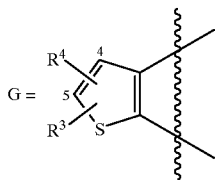

G =

| $R^3$ | $R^4$ | $R^3$ | $R^4$ | $R^3$ | $R^4$ |
|---|---|---|---|---|---|
| 4-Br | H | 5-C≡CSiMe$_3$ | H | 5-C≡CH | H |
| 4-Cl | H | 4-C≡CH | H | 4-CH=CH$_2$ | H |
| 4-I | H | 5-I | H | 5-CH=CH$_2$ | H |
| 4-I | 5-I | 4-CF$_3$ | H | 5-C≡CH | 4-Br |
| 4-Br | 5-Br | 4-c-propyl | H | 5-Br | 4-Me |
| 5-Br | H | | | 4-I | 5-Et |

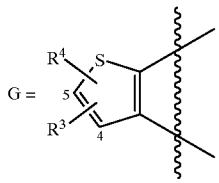

G =

| $R^3$ | $R^4$ | $R^3$ | $R^4$ | $R^3$ | $R^4$ |
|---|---|---|---|---|---|
| 4-Br | H | 5-I | H | 4-CH$_2$Br | H |
| 4-Cl | H | 4-C≡CH | H | 4-CH=CH$_2$ | H |
| 4-I | H | 5-C≡CSiMe$_3$ | H | 5-CH=CH$_2$ | H |
| 4-I | 5-I | 4-c-propyl | H | 5-C≡CH | 4-Br |

TABLE 1-continued

Compounds of Formula I wherein Q is O, R¹ = R² = n-propyl, W is O,

| 4-Br | 5-Br | 4-CF₃  | H | 5-Br | 4-Me |
| 5-Br | H    | 5-C≡CH | H | 5-I  | 4-Et |

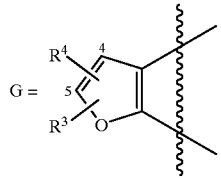

| R³   | R⁴   | R³         | R⁴ | R³       | R⁴   |
|------|------|------------|----|----------|------|
| 4-Br | H    | 5-C≡CSiMe₃ | H  | 5-C≡CH   | H    |
| 4-Cl | H    | 4-C≡CH     | H  | 4-CH=CH₂ | H    |
| 4-I  | H    | 5-I        | H  | 5-CH=CH₂ | H    |
| 4-I  | 5-I  | H          | H  | 5-C≡CH   | 4-Br |
| 4-Br | 5-Br | 4-CF₃      | H  | 5-Br     | 4-Me |
| 5-Br | H    |            |    | 4-I      | 5-Et |

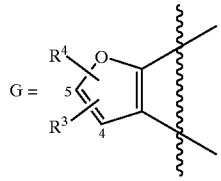

| R³   | R⁴   | R³         | R⁴ | R³       | R⁴   |
|------|------|------------|----|----------|------|
| 4-Br | H    | 5-I        | H  | 4-CH₂Br  | H    |
| 4-Cl | H    | 4-C≡CH     | H  | 4-CH=CH₂ | H    |
| 4-I  | H    | 5-C≡SiMe₃  | H  | 5-CH=CH₂ | H    |
| 4-I  | 5-I  | 4-c-propyl | H  | 5-C≡CH   | 4-Br |
| 4-Br | 5-Br | 4-CF₃      | H  | 5-Br     | 4-Me |
| 5-Br | H    | 5-C≡CH     | H  | 5-I      | 4-Et |

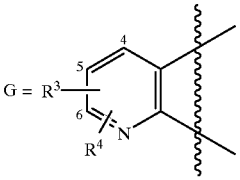

| R³   | R⁴  | R³         | R⁴   | R³       | R⁴   |
|------|-----|------------|------|----------|------|
| 5-Br | H   | 4-Br       | 5-Br | 5-CH₂F   | H    |
| 5-Cl | H   | 5-C≡CH     | H    | 5-CH=CH₂ | H    |
| 5-I  | H   | 5-C≡CSiMe₃ | H    | 5-Br     | 6-Me |
| 5-I  | 4-I | 5-c-propyl | H    | 4-Br     | H    |
| 5-Br | 6-Br| 5-CF₃      | H    | 4-Br     | 6-Br |
| 5-I  | 6-I | 5-I        | 6-Me |          |      |

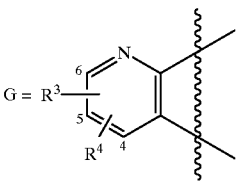

| R³   | R⁴  | R³         | R⁴ | R³       | R⁴   |
|------|-----|------------|----|----------|------|
| 6-Br | H   | 6-Br       | 5-Br | 6-CH₂F  | H    |
| 6-Cl | H   | 6-C≡CH     | H    | 6-CH=CH₂| H    |
| 6-I  | H   | 6-C≡CSiMe₃ | H    | 6-Br    | 4-Me |

TABLE 1-continued

Compounds of Formula I wherein Q is O, R$^1$ = R$^2$ = n-propyl, W is O,

| | | | | | |
|---|---|---|---|---|---|
| 6-Cl | 4-Cl | 6-C-propyl | H | 4-Br | H |
| 6-Br | 4-Br | 6-CF$_3$ | H | 4-I | H |
| 6-I | 4-I | 6-I | 4-Me | | |

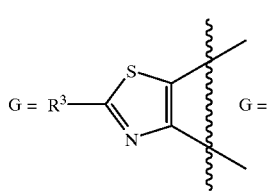

| R$^3$ | R$^3$ | R$^3$ | R$^3$ | R$^3$ | R$^3$ |
|---|---|---|---|---|---|
| Br | H | Br | H | Br | H |
| Cl | CF$_3$ | Cl | CF$_3$ | Cl | CF$_3$ |
| I | CH$_2$Br | I | CH$_2$Br | I | CH$_2$Br |
| Me | CH=CH$_2$ | Me | CH=CH$_2$ | Me | CH=CH$_2$ |
| Et | F | Et | F | Et | F |
| C≡CH | MeO | C≡CH | MeO | C≡CH | MeO |

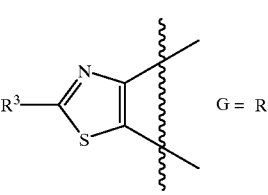

| R$^3$ | R$^3$ | R$^3$ | R$^4$ | R$^3$ | R$^4$ |
|---|---|---|---|---|---|
| Br | CF$_3$ | 6-Br | H | 6-Br | H |
| Cl | CH$_2$Br | 6-C≡CH | H | 6-C≡CH | H |
| I | CH=CH$_2$ | 6-I | H | 6-I | H |
| C≡CH | F | 6-Br | 5-Br | 6-I | 5-I |
| | MeO | 6-I | 5-I | 6-I | 5-Me |
| | | H | H | | |

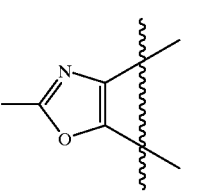

| R$^3$ | R$^4$ | R$^3$ | R$^4$ | R$^3$ | R$^4$ |
|---|---|---|---|---|---|
| 6-Br | H | 2-Br | H | 4-Br | H |
| 6-C≡CH | H | 2-C≡CH | H | 6-C≡CH | H |
| 6-I | H | 2-I | H | 4-I | H |
| 6-Br | 2-Br | 2-Br | 6-Br | 4-Br | 6-Br |
| 6-I | 2-I | 2-I | 6-I | 4-I | 6-I |
| 6-CH=CH$_2$ | H | 2-CH=CH$_2$ | H | H | H |

TABLE 1-continued

Compounds of Formula I wherein Q is O, $R^1 = R^2$ = n-propyl, W is O,

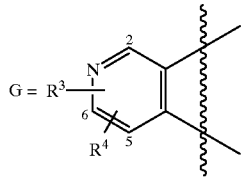

| $R^3$ | $R^4$ |
|---|---|
| 6-Br | H |
| 6-C≡CH | H |
| 6-I | H |
| 6-Br | 2-Br |
| 6-I | 2-I |
| 6-CH=CH$_2$ | H |

TABLE 2

Compounds of Formula I wherein Q = O, $R^2$ = n-Pr,

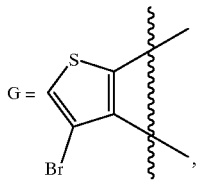

W = O,

| $R^1$ | $R^1$ | $R^1$ | $R^1$ |
|---|---|---|---|
| Me | n-Bu | n-pentyl | n-hexyl |
| Et | i-Pr | i-Bu | s-Bu |
| c-propyl | c-butyl | c-pentyl | 2-propenyl |
| 3-butenyl | 2-propynyl | 3-butynyl | CF$_3$ |
| 2-Cl—Et | 3-Br-n-Pr | CH$_2$CH=CHCl | CH$_2$C≡CCl |
| CH$_2$OCH$_3$ | CH$_2$OCH$_2$CH$_3$ | CH$_2$SCH$_3$ | CH$_2$SCH$_2$CH$_3$ |
| CH$_2$CH$_2$SCH$_3$ | CH$_2$CH$_2$OCH$_2$C≡CH | CH$_2$CH$_2$CH$_2$S(O)$_2$CH$_3$ | (c-pentyl)CH$_2$ |
| CH$_2$CH$_2$OCH$_2$CH=CH$_2$ | CH$_2$CH$_2$SCH$_2$C≡CH | CH$_2$OCF$_3$ | CH$_2$OCH$_2$CH$_2$Cl |
| CH$_2$CH$_2$SCH$_2$CH=CH$_2$ | CH$_2$CH$_2$NO$_2$ | CH$_2$CH=CHCH$_2$OCH$_3$ | CH$_2$CH$_2$N(CH$_3$)$_2$ |
| CH$_2$CH=CHCH$_2$SCH$_3$ | NHCH$_2$CH$_2$CH$_3$ | CH$_2$CH$_2$Si(CH$_3$)$_3$ | CH$_2$CH$_2$CO$_2$CH$_3$ |
| CH$_2$CH$_2$CH$_2$NHCH$_3$ | 2-furanyl | CH$_2$CH$_2$CH$_2$CN | Ph |
| OCH$_2$CH$_2$CH$_3$ | 3-benzo[b]thiophenyl | N(CH$_3$)CH$_2$CH$_3$ | (2-THF)CH$_2$ |
| 2-pyridinyl | 3-MeO—Ph | 2-thienyl | 4-F—Ph |
| 5-benzofuranyl | 4-PhO—Ph | 3-quinolinyl | 3-CF$_3$O—Ph |
| 2-F-4-Me—Ph | c-hexyl | 2-F-4-Cl—Ph | 4-Cl—Ph |
| 4-MeS—Ph | (c-propyl)CH$_2$ | 4-Ph—Ph | 3-NO$_2$—Ph |

W = NH,

| $R^1$ | $R^1$ | $R^1$ | $R^1$ |
|---|---|---|---|
| Me | n-Bu | n-pentyl | n-hexyl |
| Et | i-Pr | i-Bu | s-Bu |
| c-propyl | c-butyl | c-pentyl | 2-propenyl |
| 3-butenyl | 2-propynyl | 3-butynyl | CF$_3$ |
| 2-Cl—Et | 3-Br-n-Pr | CH$_2$CH=CHCl | CH$_2$C≡CCl |
| CH$_2$OCH$_3$ | CH$_2$OCH$_2$CH$_3$ | CH$_2$SCH$_3$ | CH$_2$SCH$_2$CH$_3$ |
| CH$_2$CH$_2$SCH$_3$ | CH$_2$CH$_2$OCH$_2$C≡CH | CH$_2$CH$_2$CH$_2$S(O)$_2$CH$_3$ | (c-pentyl)CH$_2$ |
| CH$_2$CH$_2$OCH$_2$CH=CH$_2$ | CH$_2$CH$_2$SCH$_2$C≡CH | CH$_2$OCF$_3$ | CH$_2$OCH$_2$CH$_2$Cl |
| CH$_2$CH$_2$SCH$_2$CH=CH$_2$ | CH$_2$CH$_2$NO$_2$ | CH$_2$CH=CHCH$_2$OCH$_3$ | CH$_2$CH$_2$N(CH$_3$)$_2$ |
| CH$_2$CH=CHCH$_2$SCH$_3$ | NHCH$_2$CH$_2$CH$_3$ | CH$_2$CH$_2$Si(CH$_3$)$_3$ | CH$_2$CH$_2$CO$_2$CH$_3$ |
| CH$_2$CH$_2$CH$_2$NHCH$_3$ | 2-furanyl | CH$_2$CH$_2$CH$_2$CN | Ph |
| OCH$_2$CH$_2$CH$_3$ | 3-benzo[b]thiophenyl | N(CH$_3$)CH$_2$CH$_3$ | (2-THF)CH$_2$ |
| 2-pyridinyl | 3-MeO—Ph | 2-thienyl | 4-F—Ph |
| 5-benzofuranyl | 4-PhO—Ph | 3-quinolinyl | 3-CF$_3$O—Ph |
| 2-F-4-Me—Ph | c-hexyl | 2-F-4-Cl—Ph | 4-Cl—Ph |

TABLE 2-continued

Compounds of Formula I wherein Q = O, R² = n-Pr,

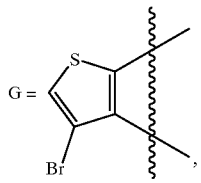

| 4-MeS—Ph | (c-propyl)CH₂ | 4-Ph—Ph | 3-NO₂—Ph |

W = S,

| R¹ | R¹ | R¹ | R¹ |
| --- | --- | --- | --- |
| Me | n-Bu | n-pentyl | n-hexyl |
| Et | i-Pr | i-Bu | s-Bu |
| c-propyl | c-butyl | c-pentyl | 2-propenyl |
| 3-butenyl | 2-propynyl | 3-butynyl | CF₃ |
| 2-Cl—Et | 3-Br-n-Pr | CH₂CH=CHCl | CH₂C≡CCl |
| CH₂OCH₃ | CH₂OCH₂CH₃ | CH₂SCH₃ | CH₃SCH₂CH₃ |
| CH₂CH₂SCH₃ | CH₂CH₂OCH₂C≡CH | CH₂CH₂CH₂S(O)₂CH₃ | (c-pentyl)CH₂ |
| CH₂CH₂OCH₂CH=CH₂ | CH₂CH₂SCH₂C≡CH | CH₂OCF₃ | CH₂OCH₂CH₂Cl |
| CH₂CH₂SCH₂CH=CH₂ | CH₂CH₂NO₂ | CH₂CH=CHCH₂OCH₃ | CH₂CH₂N(CH₃)₂ |
| CH₂CH=CHCH₂SCH₃ | NHCH₂CH₂CH₃ | CH₂CH₂Si(CH₃)₃ | CH₂CH₂CO₂CH₃ |
| CH₂CH₂CH₂NHCH₃ | 2-furanyl | CH₂CH₂CH₂CN | Ph |
| OCH₂CH₂CH₃ | 3-benzo[b]thiophenyl | N(CH₃)CH₂CH₃ | (2-THF)CH₂ |
| 2-pyridinyl | 3-MeO—Ph | 2-thienyl | 4-F—Ph |
| 5-benzofuranyl | 4-PhO—Ph | 3-quinolinyl | 3-CF₃O—Ph |
| 2-F-4-Me—Ph | c-hexyl | 2-F-4-Cl—Ph | 4-Cl—Ph |
| 4-MeS—Ph | (c-propyl)CH₂ | 4-Ph—Ph | 3-NO₂—Ph |

TABLE 3

Compounds of Formula I wherein: Q = O, R¹ = n-Pr,

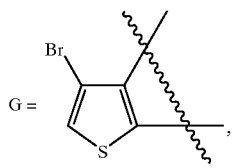

W = O

| R² | R² | R² | R² |
| --- | --- | --- | --- |
| Et | n-Pr | i-Pr | n-Bu |
| i-Bu | s-Bu | n-pentyl | n-hexyl |
| n-decyl | c-hexyl | 2-propenyl | 2-butenyl |
| 3-butenyl | 5-decenyl | 2-propynyl | 2-butynyl |
| 3-butynyl | CF₃ | CH₂CF₃ | CH₂CH=CHCl |
| CH₂C≡CBr | CH₂OCH₃ | CH₂OCH₂CH₃ | CH₂CH₂OCH₃ |
| CH₂SCH₃ | CH₂CH₂SCH₃ | CH₂CH₂CH₂S(O)₂CH₃ | (c-pentyl)CH₂ |
| 2-Cl—Et | CH₂CH₂OCH₂C≡CH | CH₂CH₂SCH₂CH=CH₂ | CH₂CH₂CH₂CN |
| CH₂CH₂Si(CH₃)₃ | CH₂CH₂OCF₃ | CH₂CH₂SCH₂C≡CH | CH₂OCH₂CH₂Cl |
| Ph | CH₂CH₂CO₂Et | CH₂CH₂CH₂N(CH₃)₂ | CH₂CH₂(4-F—Ph) |
| 4-MeO—Ph | CH₂Ph | CH₂CH₂OCH₂CH=CH₂ | N(CH₃)₂ |
| CH₂CH₂CH₂NHCH₃ | CH₂CH₂NO₂ | NHCH₂CH₂CH₃ | 2-CN—Ph |
| 2,4-diCl—Ph | 2,4,6-triF—Ph | 4-CF₃—Ph | CH₂CH₂CH₂Ph |
| (2-THF)CH₂ | (c-propyl)CH₂ | CH₂CN | 4-Cl—Ph |

W = NH,

| R² | R² | R² | R² |
| --- | --- | --- | --- |
| Et | n-Pr | i-Pr | n-Bu |
| i-Bu | s-Bu | n-pentyl | n-hexyl |

TABLE 3-continued

Compounds of Formula I wherein: Q = O, R$^1$ = n-Pr,

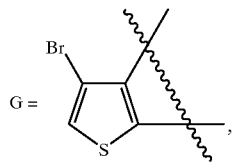

| | | | |
|---|---|---|---|
| n-decyl | c-hexyl | 2-propenyl | 2-butenyl |
| 3-butenyl | 5-decenyl | 2-propynyl | 2-butynyl |
| 3-butynyl | CF$_3$ | CH$_2$CF$_3$ | CH$_2$CH=CHCl |
| CH$_2$C≡CBr | CH$_2$OCH$_3$ | CH$_2$OCH$_2$CH$_3$ | CH$_2$CH$_2$OCH$_3$ |
| CH$_2$SCH$_3$ | CH$_2$CH$_2$SCH$_3$ | CH$_2$CH$_2$CH$_2$S(O)$_2$CH$_3$ | (c-pentyl)CH$_2$ |
| 2-Cl—Et | CH$_2$CH$_2$OCH$_2$C≡CH | CH$_2$CH$_2$SCH$_2$CH=CH$_2$ | CH$_2$CH$_2$CH$_2$CN |
| CH$_2$CH$_2$Si(CH$_3$)$_3$ | CH$_2$CH$_2$OCF$_3$ | CH$_2$CH$_2$SCH$_2$C≡CH | CH$_2$OCH$_2$CH$_2$Cl |
| Ph | CH$_2$CH$_2$CO$_2$Et | CH$_2$CH$_2$CH$_2$N(CH$_3$)$_2$ | CH$_2$CH$_2$(4-F—Ph) |
| 4-MeO—Ph | CH$_2$Ph | CH$_2$CH$_2$OCH$_2$CH=CH$_2$ | N(CH$_3$)$_2$ |
| CH$_2$CH$_2$CH$_2$NHCH$_3$ | CH$_2$CH$_2$NO$_2$ | NHCH$_2$CH$_2$CH$_3$ | 2-CN—Ph |
| 2,4-diCl—Ph | 2,4,6-triF—Ph | 4-CF$_3$—Ph | CH$_2$CH$_2$CH$_2$Ph |
| (2-THF)CH$_2$ | (c-propyl)CH$_2$ | CH$_2$CN | 4-Cl—Ph |

TABLE 4

Compounds of Formula I wherein Q = O, R$^2$ = n-Pr,

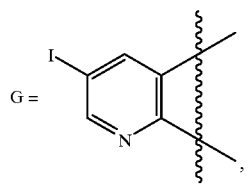

W = O,

| R$^1$ | R$^1$ | R$^1$ | R$^1$ |
|---|---|---|---|
| Me | n-Bu | n-pentyl | n-hexyl |
| Et | i-Pr | i-Bu | s-Bu |
| c-propyl | c-butyl | c-pentyl | 2-propenyl |
| 3-butenyl | 2-propynyl | 3-butynyl | CF$_3$ |
| 2-Cl—Et | 3-Br-n-Pr | CH$_2$CH=CHCl | CH$_2$C≡CCl |
| CH$_2$OCH$_3$ | CH$_2$OCH$_2$CH$_3$ | CH$_2$SCH$_3$ | CH$_2$SCH$_2$CH$_3$ |
| CH$_2$CH$_2$SCH$_3$ | CH$_2$CH$_2$OCH$_2$C≡CH | CH$_2$CH$_2$CH$_2$S(O)$_2$CH$_3$ | (c-pentyl)CH$_2$ |
| CH$_2$CH$_2$OCH$_2$CH=CH$_2$ | CH$_2$CH$_2$SCH$_2$C≡CH | CH$_2$OCF$_3$ | CH$_2$OCH$_2$CH$_2$Cl |
| CH$_2$CH$_2$SCH$_2$CH=CH$_2$ | CH$_2$CH$_2$NO$_2$ | CH$_2$CH=CHCH$_2$OCH$_3$ | CH$_2$CH$_2$N(CH$_3$)$_2$ |
| CH$_2$CH=CHCH$_2$SCH$_3$ | NHCH$_2$CH$_2$CH$_3$ | CH$_2$CH$_2$Si(CH$_3$)$_3$ | CH$_2$CH$_2$CO$_2$CH$_3$ |
| CH$_2$CH$_2$CH$_2$NHCH$_3$ | 2-furanyl | CH$_2$CH$_2$CN | Ph |
| OCH$_2$CH$_2$CH$_3$ | 3-benzo[b]thiophenyl | N(CH$_3$)CH$_2$CH$_3$ | (2-THF)CH$_2$ |
| 2-pyridinyl | 3-MeO—Ph | 2-thienyl | 4-F—Ph |
| 5-benzofuranyl | 4-PhO—Ph | 3-quinolinyl | 3-CF$_3$O—Ph |
| 2-F-4-Me—Ph | c-hexyl | 2-F-4-Cl—Ph | 4-Cl—Ph |
| 4-MeS—Ph | (c-propyl)CH$_2$ | 4-Ph—Ph | 3-NO$_2$—Ph |

W = S,

| R$^1$ | R$^1$ | R$^1$ | R$^1$ |
|---|---|---|---|
| Me | n-Bu | n-pentyl | n-hexyl |
| Et | i-Pr | i-Bu | s-Bu |
| c-propyl | c-butyl | c-pentyl | 2-propenyl |
| 3-butenyl | 2-propynyl | 3-butynyl | CF$_3$ |
| 2-Cl—Et | 3-Br-n-Pr | CH$_2$CH=CHCl | CH$_2$C≡CCl |
| CH$_2$OCH$_3$ | CH$_2$OCH$_2$CH$_3$ | CH$_2$SCH$_3$ | CH$_2$SCH$_2$CH$_3$ |
| CH$_2$CH$_2$SCH$_3$ | CH$_2$CH$_2$OCH$_2$C≡CH | CH$_2$CH$_2$CH$_2$S(O)$_2$CH$_3$ | (c-pentyl)CH$_2$ |
| CH$_2$CH$_2$OCH$_2$CH=CH$_2$ | CH$_2$CH$_2$SCH$_2$C≡CH | CH$_2$OCF$_3$ | CH$_2$OCH$_2$CH$_2$Cl |
| CH$_2$CH$_2$SCH$_2$CH=CH$_2$ | CH$_2$CH$_2$NO$_2$ | CH$_2$CH=CHCH$_2$OCH$_3$ | CH$_2$CH$_2$N(CH$_3$)$_2$ |
| CH$_2$CH=CHCH$_2$SCH$_3$ | NHCH$_2$CH$_2$CH$_3$ | CH$_2$CH$_2$Si(CH$_3$)$_3$ | CH$_2$CH$_2$CO$_2$CH$_3$ |

TABLE 4-continued

Compounds of Formula I wherein Q = O, $R^2$ = n-Pr,

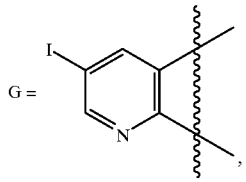

| | | | |
|---|---|---|---|
| CH$_2$CH$_2$CH$_2$NHCH$_3$ | 2-furanyl | CH$_2$CH$_2$CH$_2$CN | Ph |
| OCH$_2$CH$_2$CH$_3$ | 3-benzo[b]thiophenyl | N(CH$_3$)CH$_2$CH$_3$ | (2-THF)CH$_2$ |
| 2-pyridinyl | 3-MeO—Ph | 2-thienyl | 4-F—Ph |
| 5-benzofuranyl | 4-PhO—Ph | 3-quinolinyl | 3-CF$_3$O—Ph |
| 2-F-4-Me—Ph | c-hexyl | 2-F-4-Cl—Ph | 4-Cl—Ph |
| 4-MeS—Ph | (c-propyl)CH$_2$ | 4-Ph—Ph | 3-NO$_2$—Ph |

TABLE 5

Compounds of Formula I wherein: Q = O, $R^1$ = n-Pr,

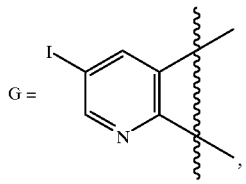

W = O

| $R^2$ | $R^2$ | $R^2$ | $R^2$ |
|---|---|---|---|
| Et | n-Pr | i-Pr | n-Bu |
| i-Bu | s-Bu | n-pentyl | n-hexyl |
| n-decyl | c-hexyl | 2-propenyl | 2-butenyl |
| 3-butenyl | 5-decenyl | 2-propynyl | 2-butynyl |
| 3-butynyl | CF$_3$ | CH$_2$CF$_3$ | CH$_2$CH=CHCl |
| CH$_2$C≡CBr | CH$_2$OCH$_3$ | CH$_2$OCH$_2$CH$_3$ | CH$_2$CH$_2$OCH$_3$ |
| CH$_2$SCH$_3$ | CH$_2$CH$_2$SCH$_3$ | CH$_2$CH$_2$S(O)$_2$CH$_3$ | (c-pentyl)CH$_2$ |
| 2-Cl—Et | CH$_2$CH$_2$OCH$_2$C≡CH | CH$_2$CH$_2$SCH$_2$CH=CH$_2$ | CH$_2$CH$_2$CH$_2$CN |
| CH$_2$CH$_2$Si(CH$_3$)$_3$ | CH$_2$CH$_2$OCF$_3$ | CH$_2$CH$_2$SCH$_2$C≡CH | CH$_2$OCH$_2$CH$_2$Cl |
| Ph | CH$_2$CH$_2$CO$_2$Et | CH$_2$CH$_2$CH$_2$N(CH$_3$)$_2$ | CH$_2$CH$_2$(4-F—Ph) |
| 4-MeO—Ph | CH$_2$Ph | CH$_2$CH$_2$OCH$_2$CH=CH$_2$ | N(CH$_3$)$_2$ |
| CH$_2$CH$_2$CH$_2$NHCH$_3$ | CH$_2$CH$_2$NO$_2$ | NHCH$_2$CH$_3$ | 2-CN—Ph |
| 2,4-diCl—Ph | 2,4,6-triF—Ph | 4-CF$_3$—Ph | CH$_2$CH$_2$CH$_2$Ph |
| (2-THF)CH$_2$ | (c-propyl)CH$_2$ | CH$_2$CN | 4-Cl-Ph |

TABLE 6

Compounds of Formula I wherein: Q = O, $R^1$ = n-Pr,

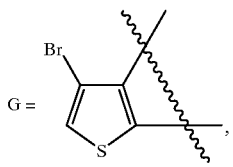

| WR$^2$ | WR$^2$ | WR$^2$ | WR$^2$ |
|---|---|---|---|
| —ON=CHCH$_2$CH$_2$CH$_3$ | —NHN=CHCH$_2$CH$_2$CH$_3$ | —ON=C(CH$_3$)$_2$ | —NHN=C(CH$_3$)$_2$ |

TABLE 6-continued

Compounds of Formula I wherein: Q = O, $R^1$ = n-Pr,

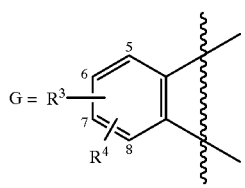

| $WR^2$ | $WR^2$ | $WR^2$ | $WR^2$ |
|---|---|---|---|
| —ON═CHCH$_2$CH$_2$CH$_3$ | —NHN═CHCH$_2$CH$_2$CH$_3$ | —ON═C(CH$_3$)$_2$ | —NHN═C(CH$_3$)$_2$ |

TABLE 7

Compounds of Formula I wherein: W = Q = O, $R^2$ = n-Pr, $R^3$ = 6-I, $R^4$ = H, $R^1$ = $R^{11}$, G = (pyridine ring with $R^3$, $R^4$ at positions 6, 8 and positions 5, 7 shown)

| $R^{11}$ | $R^8$ | $R^9$ | $R^{10}$ |
|---|---|---|---|
| CH$_2$(Y-96) | — | — | — |
| (CH$_2$)$_2$CH(CH$_3$)(CH$_2$)$_2$(Y-96) | 2-CH$_3$ | 3-CH$_3$ | — |
| (CH$_2$)$_{10}$(Y-96) | 3-(CH$_2$)$_5$CH$_3$ | 3-CH$_3$ | — |
| CH$_2$(Y-97) | 1-C$_6$F$_5$ | 3-CH$_2$CH$_3$ | — |
| CH$_2$(Y-98) | — | — | — |
| CH$_2$(Y-99) | 3-(4-Me—Ph) | 2-OCH$_3$ | — |
| CH$_2$(Y-100) | 2-OCH$_3$ | — | — |
| CH$_2$(Y-52) | — | — | — |
| (CH$_2$)$_5$(Y-52) | 3-O(CH$_2$)$_5$CH$_3$ | — | — |
| (CH$_2$)$_2$CH(CH$_3$)(CH$_2$)$_2$(Y-52) | 4-CN | — | — |
| (CH$_2$)$_{10}$(Y-93) | 3-CF$_3$ | — | — |
| CH$_2$(Y-52) | 4-(CF$_2$)$_5$CF$_3$ | 5-F | 5-F |
| CH$_2$(Y-52) | 3-Cl | 4-CF$_3$ | — |
| CH$_2$(Y-93) | 2-C≡CH | 4-SCH$_3$ | — |
| CH$_2$(Y-3) | — | — | — |
| CH$_2$(Y-3) | 4-C≡C(CH$_2$)$_5$CH$_3$ | 5-I | — |
| (CH$_2$)$_{10}$(Y-4) | 4-SCH$_3$ | 5-Cl | — |
| CH$_2$(Y-2) | — | — | — |
| CH$_2$(Y-2) | 3-OCF$_3$ | — | — |
| CH$_2$(Y-2) | 3-O(CF$_2$)$_5$CF$_3$ | 4-CH$_3$ | — |
| CH$_2$(Y-1) | — | — | — |
| CH$_2$(Y-1) | — | — | 5-Cl |
| (CH$_2$)$_5$(Y-5) | 2-Br | 4-Br | 5-Br |
| CH$_2$(Y-16) | 2-CH$_3$ | 3-CH$_2$CH$_3$ | — |
| CH$_2$(Y-15) | 3-Br | — | — |
| CH$_2$(Y-15) | — | 3-CO$_2$CH$_2$CH$_3$ | — |
| CH$_2$(Y-15) | — | 3-C(O)N(CH$_3$)$_2$ | — |
| CH$_2$(Y-15) | — | 3-C(O)N(CH$_2$CH$_3$)$_2$ | — |
| CH$_2$(Y-15) | 3-SCH$_2$CH$_3$ | — | — |
| (CH$_2$)$_{10}$(Y-15) | 3-N(CH$_3$)$_2$ | — | — |
| (CH$_2$)$_5$(Y-17) | 3-N(CH$_2$CH$_3$)$_2$ | 5-CH$_3$ | — |
| CH$_2$(Y-14) | 3-Br | — | — |
| CH$_2$(Y-14) | — | 3-CO$_2$CH$_2$CH$_3$ | — |
| CH$_2$(Y-14) | — | 3-C(O)N(CH$_3$)$_2$ | — |
| CH$_2$(Y-14) | — | 3-C(O)N(CH$_2$CH$_3$)$_2$ | — |
| CH$_2$(Y-13) | 3-OCH$_2$CH$_3$ | 5-CH$_2$CH$_3$ | — |
| CH$_2$(Y-14) | 3-OCH$_2$CH$_3$ | 4-CH$_2$CH$_3$ | — |
| CH$_2$(Y-60) | 2-(4-Cl—Ph) | 5-CO$_2$CH$_3$ | — |
| CH$_2$(Y-60) | 2-(2,4-diBr—Ph) | 5-CO$_2$CH$_3$ | — |
| (CH$_2$)$_8$(Y-21) | 2-(3-NO$_2$—Ph) | 5-CO$_2$CH$_3$ | — |
| CH$_2$(Y-11) | 3-(2-CN—PhO) | — | — |
| CH$_2$(Y-91) | 1-(4-CF$_3$—Ph) | — | — |
| (CH$_2$)$_4$(Y-27) | 3-CF$_2$CF$_2$CF$_3$ | — | — |
| CH$_2$(Y-37) | — | — | — |

TABLE 7-continued

Compounds of Formula I wherein: W = Q = O, $R^2$ = n-Pr, $R^3$ = 6-I, $R^4$ = H, $R^1$ = $R^{11}$,

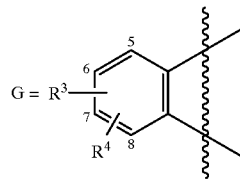

G =

| $R^{11}$ | $R^8$ | $R^9$ | $R^{10}$ |
|---|---|---|---|
| $CH_2$(Y-38) | — | — | — |
| $(CH_2)_7$(Y-38) | 6-$SCCl_3$ | 5-Cl | 2-Cl |
| $CH_2$(Y-39) | 2-$S(CF_2)_5CF_3$ | 6-$CF_3$ | — |
| $CH_2$(Y-44) | — | — | — |
| $(CH_2)_9$(Y-45) | 2-F | 5-F | 6-F |
| $CH_2$(Y-46) | 4-(C(O)$CH_3$) | 6-I | — |
| $CH_2$(Y-51) | 3-C($CH_3$)$_3$ | — | — |
| $CH_2$(Y-51) | 3-Ph | — | — |
| $CH_2$(Y-51) | 3-[4-$CF_3$($CF_2$)$_3$-Ph] | — | — |
| $CH_2$(Y-92) | 5-$CF_3$ | 6-$CF_3$ | — |
| $(CH_2)CH(CH_3)CH_2$(Y-66) | 4-CH=$CH_2$ | 3-$OCH_3$ | — |
| $CH_2$(Y-71) | 1-I | 3-Br | 4-Cl |
| $CH_2$(Y-75) | — | — | — |
| $CH_2$(Y-75) | 7-[4-$CH_3$O—Ph] | — | — |
| $(CH_2)_2$(Y-75) | 4-$(CH_2)_4CH$=$CH_2$ | 2-$SCH_3$ | — |
| $CH_2$(Y-85) | 6-$(CH_2)CH$=$CH(CF_3)$ | 2-I | 4-I |
| $CH_2$(Y-85) | — | — | — |
| $CH_2$(Y-85) | 6-[4-$CH_3(CH_2)_3O$—Ph] | — | — |
| $CH_2$(Y-78) | 5-CCl=$CCl_2$ | — | — |
| $CH_2$(Y-78) | 6-CF=CF($CF_2$)$_3CH_3$ | — | — |
| $CH_2$(Y-79) | 2-$CF_2CF$=$CFCF_3$ | — | — |
| $CH_2$(Y-87) | — | — | — |
| $CH_2$(Y-87) | 7-Cl | 5-Cl | 3-Cl |
| $CH_2$(Y-89) | 4-[4-$(CH_3)_3C$—Ph] | 2-$CH_3$ | — |
| $CH_2$(Y-54) | 2-$CH_3$ | 2-$CH_3$ | — |
| $CH_2$(Y-54) | 2-Ph | — | — |
| $CH_2$(Y-95) | — | — | — |
| $CH_2$(Y-94) | — | — | — |

TABLE 8

Compounds of Formula I wherein: W = NH, Q = O, $R^2$ = n-Pr, $R^3$ = 6-I, $R^4$ = H, $R^1$ = $R^{11}$,

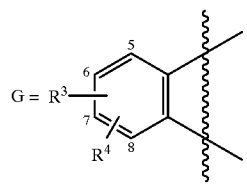

G =

| $R^{11}$ | $R^8$ | $R^9$ | $R^{10}$ |
|---|---|---|---|
| $CH_2$(Y-96) | — | — | — |
| $(CH_2)_2CH(CH_3)(CH_2)_2$(Y-96) | 2-$CH_3$ | 3-$CH_3$ | — |
| $(CH_2)_{10}$(Y-96) | 3-$(CH_2)_5CH_3$ | 3-$CH_3$ | — |
| $CH_2$(Y-97) | 1-$C_6F_5$ | 3-$CH_2CH_3$ | — |
| $CH_2$(Y-98) | — | — | — |
| $CH_2$(Y-99) | 3-(4-Me—Ph) | 2-$OCH_3$ | — |
| $CH_2$(Y-100) | 2-$OCH_3$ | — | — |
| $CH_2$(Y-52) | — | — | — |
| $(CH_2)_5$(Y-52) | 3-O$(CH_2)_5CH_3$ | — | — |
| $(CH_2)_2CH(CH_3)(CH_2)_2$(Y-52) | 4-CN | — | — |
| $(CH_2)_{10}$(Y-93) | 3-$CF_3$ | — | — |
| $CH_2$(Y-52) | 4-$(CF_2)_5CF_3$ | 5-F | 5-F |
| $CH_2$(Y-52) | 3-Cl | 4-$CF_3$ | — |
| $CH_2$(Y-93) | 2-C≡CH | 4-$SCH_3$ | — |
| $CH_2$(Y-3) | — | — | — |
| $CH_2$(Y-3) | 4-C≡C$(CH_2)_5CH_3$ | 5-I | — |
| $(CH_2)_{10}$(Y-4) | 4-$SCH_3$ | 5-Cl | — |

TABLE 8-continued

Compounds of Formula I wherein: W = NH, Q = O, $R^2$ = n-Pr, $R^3$ = 6-I, $R^4$ = H, $R^1$ = $R^{11}$,

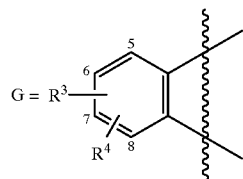

| $R^{11}$ | $R^8$ | $R^9$ | $R^{10}$ |
|---|---|---|---|
| CH$_2$(Y-2) | — | — | — |
| CH$_2$(Y-2) | 3-OCF$_3$ | — | — |
| CH$_2$(Y-2) | 3-O(CF$_2$)$_5$CF$_3$ | 4-CH$_3$ | — |
| CH$_2$(Y-1) | — | — | — |
| CH$_2$(Y-1) | — | — | 5-Cl |
| (CH$_2$)$_5$(Y-5) | 2-Br | 4-Br | 5-Br |
| CH$_2$(Y-16) | 2-CH$_3$ | 3-CH$_2$CH$_3$ | — |
| CH$_2$(Y-15) | 3-Br | — | — |
| CH$_2$(Y-15) | — | 3-CO$_2$CH$_2$CH$_3$ | — |
| CH$_2$(Y-15) | — | 3-C(O)N(CH$_3$)$_2$ | — |
| CH$_2$(Y-15) | — | 3-C(O)N(CH$_2$CH$_3$)$_2$ | — |
| CH$_2$(Y-15) | 3-SCH$_2$CH$_2$CH$_3$ | — | — |
| (CH$_2$)$_{10}$(Y-15) | 3-N(CH$_3$)$_2$ | — | — |
| (CH$_2$)$_5$(Y-17) | 3-N(CH$_2$CH$_3$)$_2$ | 5-CH$_3$ | — |
| CH$_2$(Y-14) | 3-Br | — | — |
| CH$_2$(Y-14) | — | 3-CO$_2$CH$_2$CH$_3$ | — |
| CH$_2$(Y-14) | — | 3-C(O)N(CH$_3$)$_2$ | — |
| CH$_2$(Y-14) | — | 3-C(O)N(CH$_2$CH$_3$)$_2$ | — |
| CH$_2$(Y-13) | 3-OCH$_2$CH$_2$CH$_3$ | 5-CH$_2$CH$_3$ | — |
| CH$_2$(Y-14) | 3-OCH$_2$CH$_2$CH$_3$ | 4-CH$_2$CH$_3$ | — |
| CH$_2$(Y-60) | 2-(4-Cl—Ph) | 5-CO$_2$CH$_3$ | — |
| CH$_2$(Y-60) | 2-(2,4-diBr—Ph) | 5-CO$_2$CH$_3$ | — |
| (CH$_2$)$_8$(Y-21) | 2-(3-NO$_2$—Ph) | 5-CO$_2$CH$_3$ | — |
| CH$_2$(Y-11) | 3-(2-CN—PhO) | — | — |
| CH$_2$(Y-91) | 1-(4-CF$_3$—Ph) | — | — |
| (CH$_2$)$_4$(Y-27) | 3-CF$_2$CF$_2$CF$_3$ | — | — |
| CH$_2$(Y-37) | — | — | — |
| CH$_2$(Y-38) | — | — | — |
| (CH$_2$)$_7$(Y-38) | 6-SCCl$_3$ | 5-Cl | 2-Cl |
| CH$_2$(Y-39) | 2-S(CF$_2$)$_5$CF$_3$ | 6-CF$_3$ | — |
| CH$_2$(Y-44) | — | — | — |
| (CH$_2$)$_9$(Y-45) | 2-F | 5-F | 6-F |
| CH$_2$(Y-46) | 4-(C(O)CH$_3$) | 6-I | — |
| CH$_2$(Y-51) | 3-C(CH$_3$)$_3$ | — | — |
| CH$_2$(Y-51) | 3-Ph | — | — |
| CH$_2$(Y-51) | 3-[4-CF$_3$(CF$_2$)$_3$-Ph] | — | — |
| CH$_2$(Y-92) | 5-CF$_3$ | 6-CF$_3$ | — |
| (CH$_2$)CH(CH$_3$)CH$_2$(Y-66) | 4-CH=CH$_2$ | 3-OCH$_3$ | — |
| CH$_2$(Y-71) | 1-I | 3-Br | 4-Cl |
| CH$_2$(Y-75) | — | — | — |
| CH$_2$(Y-75) | 7-[4-CH$_3$O—Ph] | — | — |
| (CH$_2$)$_2$(Y-75) | 4-(CH$_2$)$_4$CH=CH$_2$ | 2-SCH$_3$ | — |
| CH$_2$(Y-85) | 6-(CH$_2$)CH=CH(CF$_3$) | 2-I | 4-I |
| CH$_2$(Y-85) | — | — | — |
| CH$_2$(Y-85) | 6-[4-CH$_3$(CH$_2$)$_3$O—Ph] | — | — |
| CH$_2$(Y-78) | 5-CCl=CCl$_2$ | — | — |
| CH$_2$(Y-78) | 6-CF=CF(CF$_2$)$_3$CH$_3$ | — | — |
| CH$_2$(Y-79) | 2-CF$_2$CF=CFCF$_3$ | — | — |
| CH$_2$(Y-87) | — | — | — |
| CH$_2$(Y-87) | 7-Cl | 5-Cl | 3-Cl |
| CH$_2$(Y-89) | 4-[4-(CH$_3$)$_3$C—Ph] | 2-CH$_3$ | — |
| CH$_2$(Y-54) | 2-CH$_3$ | 2-CH$_3$ | — |
| CH$_2$(Y-54) | 2-Ph | — | — |
| CH$_2$(Y-95) | — | — | — |
| CH$_2$(Y-94) | — | — | — |

TABLE 9

Compounds of Formula I wherein: W = S, Q = O, $R^2$ = n-Pr, $R^3$ = 6-I, $R^4$ = H, $R^1$ = $R^{11}$,

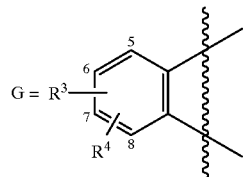

| $R^{11}$ | $R^8$ | $R^9$ | $R^{10}$ |
|---|---|---|---|
| CH$_2$(Y-96) | — | — | — |
| (CH$_2$)$_2$CH(CH$_3$)(CH$_2$)$_2$(Y-96) | 2-CH$_3$ | 3-CH$_3$ | — |
| (CH$_2$)$_{10}$(Y-96) | 3-(CH$_2$)$_5$CH$_3$ | 3-CH$_3$ | — |
| CH$_2$(Y-97) | 1-C$_6$F$_5$ | 3-CH$_2$CH$_3$ | — |
| CH$_2$(Y-98) | — | — | — |
| CH$_2$(Y-99) | 3-(4-Me-Ph) | 2-OCH$_3$ | — |
| CH$_2$(Y-100) | 2-OCH$_3$ | — | — |
| CH$_2$(Y-52) | — | — | — |
| (CH$_2$)$_5$(Y-52) | 3-O(CH$_2$)$_5$CH$_3$ | — | — |
| (CH$_2$)$_2$CH(CH$_3$)(CH$_2$)$_2$(Y-52) | 4-CN | — | — |
| (CH$_2$)$_{10}$(Y-93) | 3-CF$_3$ | — | — |
| CH$_2$(Y-52) | 4-(CF$_2$)$_5$CF$_3$ | 5-F | 5-F |
| CH$_2$(Y-52) | 3-Cl | 4-CF$_3$ | — |
| CH$_2$(Y-93) | 2-C≡CH | 4-SCH$_3$ | — |
| CH$_2$(Y-3) | — | — | — |
| CH$_2$(Y-3) | 4-C≡C(CH$_2$)$_5$CH$_3$ | 5-I | — |
| (CH$_2$)$_{10}$(Y-4) | 4-SCH$_3$ | 5-Cl | — |
| CH$_2$(Y-2) | — | — | — |
| CH$_2$(Y-2) | 3-OCF$_3$ | — | — |
| CH$_2$(Y-2) | 3-O(CF$_2$)$_5$CF$_3$ | 4-CH$_3$ | — |
| CH$_2$(Y-1) | — | — | — |
| CH$_2$(Y-1) | — | — | 5-Cl |
| (CH$_2$)$_5$(Y-5) | 2-Br | 4-Br | 5-Br |
| CH$_2$(Y-16) | 2-CH$_3$ | 3-CH$_2$CH$_3$ | — |
| CH$_2$(Y-15) | 3-Br | — | — |
| CH$_2$(Y-15) | — | 3-CO$_2$CH$_2$CH$_3$ | — |
| CH$_2$(Y-15) | — | 3-C(O)N(CH$_3$)$_2$ | — |
| CH$_2$(Y-15) | — | 3-C(O)N(CH$_2$CH$_3$)$_2$ | — |
| CH$_2$(Y-15) | 3-SCH$_2$CH$_3$ | — | — |
| (CH$_2$)$_{10}$(Y-15) | 3-N(CH$_3$)$_2$ | — | — |
| (CH$_2$)$_5$(Y-17) | 3-N(CH$_2$CH$_3$)$_2$ | 5-CH$_3$ | — |
| CH$_2$(Y-14) | 3-Br | — | — |
| CH$_2$(Y-14) | — | 3-CO$_2$CH$_2$CH$_3$ | — |
| CH$_2$(Y-14) | — | 3-C(O)N(CH$_3$)$_2$ | — |
| CH$_2$(Y-14) | — | 3-C(O)N(CH$_2$CH$_3$)$_2$ | — |
| CH$_2$(Y-13) | 3-OCH$_2$CH$_2$CH$_3$ | 5-CH$_2$CH$_3$ | — |
| CH$_2$(Y-14) | 3-OCH$_2$CH$_2$CH$_3$ | 4-CH$_2$CH$_3$ | — |
| CH$_2$(Y-60) | 2-(4-Cl-Ph) | 5-CO$_2$CH$_3$ | — |
| CH$_2$(Y-60) | 2-(2,4-diBr-Ph) | 5-CO$_2$CH$_3$ | — |
| (CH$_2$)$_8$(Y-21) | 2-(3-NO$_2$-Ph) | 5-CO$_2$CH$_3$ | — |
| CH$_2$(Y-11) | 3-(2-CN-PhO) | — | — |
| CH$_2$(Y-91) | 1-(4-CF$_3$-Ph) | — | — |
| (CH$_2$)$_4$(Y-27) | 3-CF$_2$CF$_2$CF$_3$ | — | — |
| CH$_2$(Y-37) | — | — | — |
| CH$_2$(Y-38) | — | — | — |
| (CH$_2$)$_7$(Y-38) | 6-SCCl$_3$ | 5-Cl | 2-Cl |
| CH$_2$(Y-39) | 2-S(CF$_2$)$_5$CF$_3$ | 6-CF$_3$ | — |
| CH$_2$(Y-44) | — | — | — |
| (CH$_2$)$_9$(Y-45) | 2-F | 5-F | 6-F |
| CH$_2$(Y-46) | 4-(C(O)CH$_3$) | 6-I | — |
| CH$_2$(Y-51) | 3-C(CH$_3$)3 | — | — |
| CH$_2$(Y-51) | 3-Ph | — | — |
| CH$_2$(Y-51) | 3-[4-CF$_3$(CF$_2$)$_3$-Ph] | — | — |
| CH$_2$(Y-92) | 5-CF$_3$ | 6-CF$_3$ | — |
| (CH$_2$)CH(CH$_3$)CH$_2$(Y-66) | 4-CH═CH$_2$ | 3-OCH$_3$ | — |
| CH$_2$(Y-71) | 1-I | 3-Br | 4-Cl |
| CH$_2$(Y-75) | — | — | — |
| CH$_2$(Y-75) | 7-[4-CH$_3$O-Ph] | — | — |
| (CH$_2$)$_2$(Y-75) | 4-(CH$_2$)$_4$CH═CH$_2$ | 2-SCH$_3$ | — |
| CH$_2$(Y-85) | 6-(CH$_2$)CH═CH(CF$_3$) | 2-I | 4-I |
| CH$_2$(Y-85) | — | — | — |
| CH$_2$(Y-85) | 6-[4-CH$_3$(CH$_2$)$_3$O-Ph] | — | — |
| CH$_2$(Y-78) | 5-CCl═CCl$_2$ | — | — |
| CH$_2$(Y-78) | 6-CF═CF(CF$_2$)$_3$CH$_3$ | — | — |

TABLE 9-continued

Compounds of Formula I wherein: W = S, Q = O, $R^2$ = n-Pr, $R^3$ = 6-I, $R^4$ = H, $R^1$ = $R^{11}$,

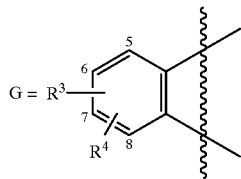

| $R^{11}$ | $R^8$ | $R^9$ | $R^{10}$ |
|---|---|---|---|
| CH$_2$(Y-79) | 2-CF$_2$CF=CFCF$_3$ | — | — |
| CH$_2$(Y-87) | — | — | — |
| CH$_2$(Y-87) | 7-Cl | 5-Cl | 3-Cl |
| CH$_2$(Y-89) | 4-[4-(CH$_3$)$_3$C-Ph] | 2-CH$_3$ | — |
| CH$_2$(Y-54) | 2-CH$_3$ | 2-CH$_3$ | — |
| CH$_2$(Y-54) | 2-Ph | — | — |
| CH$_2$(Y-95) | — | — | — |
| CH$_2$(Y-94) | — | — | — |

TABLE 10

Compounds of Formula I wherein: W = Q = O, $R^1$ = n-Pr, $R^3$ = 6-I, $R^4$ = H, $R^2$ = $R^{11}$,

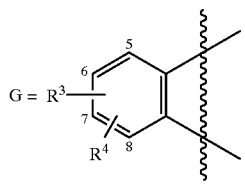

| $R^{11}$ | $R^8$ | $R^9$ | $R^{10}$ |
|---|---|---|---|
| CH$_2$(Y-96) | — | — | — |
| (CH$_2$)$_2$CH(CH$_3$)(CH$_2$)$_2$(Y-96) | 2-CH$_3$ | 3-CH$_3$ | — |
| (CH$_2$)$_{10}$(Y-96) | 3-(CH$_2$)$_5$CH$_3$ | 3-CH$_3$ | — |
| CH$_2$(Y-97) | 1-C$_6$F$_5$ | 3-CH$_2$CH$_3$ | — |
| CH$_2$(Y-98) | — | — | — |
| CH$_2$(Y-99) | 3-(4-Me-Ph) | 2-OCH$_3$ | — |
| CH$_2$(Y-100) | 2-OCH$_3$ | — | — |
| CH$_2$(Y-52) | — | — | — |
| (CH$_2$)$_5$(Y-52) | 3-O(CH$_2$)$_5$CH$_3$ | — | — |
| (CH$_2$)$_2$CH(CH$_3$)(CH$_2$)$_2$(Y-52) | 4-CN | — | — |
| (CH$_2$)$_{10}$(Y-93) | 3-CF$_3$ | — | — |
| CH$_2$(Y-52) | 4-(CF$_2$)$_5$CF$_3$ | 5-F | 5-F |
| CH$_2$(Y-52) | 3-Cl | 4-CF$_3$ | — |
| CH$_2$(Y-93) | 2-C≡CH | 4-SCH$_3$ | — |
| CH$_2$(Y-3) | — | — | — |
| CH$_2$(Y-3) | 4-C≡C(CH$_2$)$_5$CH$_3$ | 5-I | — |
| (CH$_2$)$_{10}$(Y-4) | 4-SCH$_3$ | 5-Cl | — |
| CH$_2$(Y-2) | — | — | — |
| CH$_2$(Y-2) | 3-OCF$_3$ | — | — |
| CH$_2$(Y-2) | 3-O(CF$_2$)$_5$CF$_3$ | 4-CH$_3$ | — |
| CH$_2$(Y-1) | — | — | — |
| CH$_2$(Y-1) | — | — | 5-Cl |
| (CH$_2$)$_5$(Y-5) | 2-Br | 4-Br | 5-Br |
| CH$_2$(Y-16) | 2-CH$_3$ | 3-CH$_2$CH$_3$ | — |
| CH$_2$(Y-15) | 3-Br | — | — |
| CH$_2$(Y-15) | — | 3-CO$_2$CH$_2$CH$_3$ | — |
| CH$_2$(Y-15) | — | 3-C(O)N(CH$_3$)$_2$ | — |
| CH$_2$(Y-15) | — | 3-C(O)N(CH$_2$CH$_3$)$_2$ | — |
| CH$_2$(Y-15) | 3-SCH$_2$CH$_2$CH$_3$ | — | — |
| (CH$_2$)$_{10}$(Y-15) | 3-N(CH$_3$)$_2$ | — | — |
| (CH$_2$)$_5$(Y-17) | 3-N(CH$_2$CH$_3$)$_2$ | 5-CH$_3$ | — |
| CH$_2$(Y-14) | 3-Br | — | — |
| CH$_2$(Y-14) | — | 3-CO$_2$CH$_2$CH$_3$ | — |
| CH$_2$(Y-14) | — | 3-C(O)N(CH$_3$)$_2$ | — |
| CH$_2$(Y-14) | — | 3-C(O)N(CH$_2$CH$_3$)$_2$ | — |
| CH$_2$(Y-13) | 3-OCH$_2$CH$_2$CH$_3$ | 5-CH$_2$CH$_3$ | — |
| CH$_2$(Y-14) | 3-OCH$_2$CH$_2$CH$_3$ | 4-CH$_2$CH$_3$ | — |

TABLE 10-continued

Compounds of Formula I wherein: W = Q = O, $R^1$ = n-Pr, $R^3$ = 6-I, $R^4$ = H, $R^2$ = $R^{11}$,

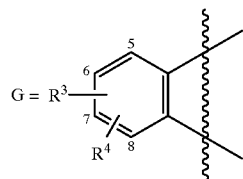

| $R^{11}$ | $R^8$ | $R^9$ | $R^{10}$ |
|---|---|---|---|
| $CH_2$(Y-60) | 2-(4-Cl-Ph) | 5-$CO_2CH_3$ | — |
| $CH_2$(Y-60) | 2-(2,4-diBr-Ph) | 5-$CO_2CH_3$ | — |
| $(CH_2)_8$(Y-21) | 2-(3-$NO_2$-Ph) | 5-$CO_2CH_3$ | — |
| $CH_2$(Y-11) | 3-(2-CN-PhO) | — | — |
| $CH_2$(Y-91) | 1-(4-$CF_3$-Ph) | — | — |
| $(CH_2)_4$(Y-27) | 3-$CF_2CF_2CF_3$ | — | — |
| $CH_2$(Y-37) | — | — | — |
| $CH_2$(Y-38) | — | — | — |
| $(CH_2)_7$(Y-38) | 6-$SCCl_3$ | 5-Cl | 2-Cl |
| $CH_2$(Y-39) | 2-$S(CF_2)_5CF_3$ | 6-$CF_3$ | — |
| $CH_2$(Y-44) | — | — | — |
| $(CH_2)_9$(Y-45) | 2-F | 5-F | 6-F |
| $CH_2$(Y-46) | 4-(C(O)$CH_3$) | 6-I | — |
| $CH_2$(Y-51) | 3-C($CH_3$)3 | — | — |
| $CH_2$(Y-51) | 3-Ph | — | — |
| $CH_2$(Y-51) | 3-[4-$CF_3$($CF_2$)$_3$-Ph] | — | — |
| $CH_2$(Y-92) | 5-$CF_3$ | 6-$CF_3$ | — |
| $(CH_2)CH(CH_3)CH_2$(Y-66) | 4-CH=$CH_2$ | 3-$OCH_3$ | — |
| $CH_2$(Y-71) | 1-I | 3-Br | 4-Cl |
| $CH_2$(Y-75) | — | — | — |
| $CH_2$(Y-75) | 7-[4-$CH_3O$-Ph] | — | — |
| $(CH_2)_2$(Y-75) | 4-($CH_2)_4$CH=$CH_2$ | 2-$SCH_3$ | — |
| $CH_2$(Y-85) | 6-($CH_2$)CH=CH($CF_3$) | 2-I | 4-I |
| $CH_2$(Y-85) | — | — | — |
| $CH_2$(Y-85) | 6-[4-$CH_3(CH_2)_3$O-Ph] | — | — |
| $CH_2$(Y-78) | 5-CCl=$CCl_2$ | — | — |
| $CH_2$(Y-78) | 6-CF=CF($CF_2)_3CH_3$ | — | — |
| $CH_2$(Y-79) | 2-$CF_2$CF=$CFCF_3$ | — | — |
| $CH_2$(Y-87) | — | — | — |
| $CH_2$(Y-87) | 7-Cl | 5-Cl | 3-Cl |
| $CH_2$(Y-89) | 4-[4-($CH_3)_3$C-Ph] | 2-$CH_3$ | — |
| $CH_2$(Y-54) | 2-$CH_3$ | 2-$CH_3$ | — |
| $CH_2$(Y-54) | 2-Ph | — | — |
| $CH_2$(Y-95) | — | — | — |
| $CH_2$(Y-94) | — | — | — |

TABLE 11

Compounds of Formula I wherein: Q = O, $R^1$ = $CH_2$(tetrahydro-2-furanyl),

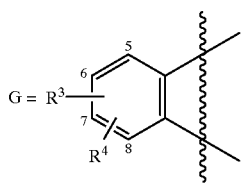

W = O, $R^3$ = 6-I, $R^4$ = H,

| $R^2$ | $R^2$ | $R^2$ | $R^2$ |
|---|---|---|---|
| $CH_2CH_2CH_2F$ | t-Bu | i-Pr | n-Bu |
| i-Bu | s-Bu | n-pentyl | n-hexyl |
| n-decyl | c-hexyl | 2-propenyl | 2-butenyl |
| 3-butenyl | 5-decenyl | 2-propynyl | 2-butynyl |
| 3-butynyl | $CF_3$ | $CH_2CF_3$ | $CH_2$CH=CHCl |
| $CH_2$C≡CBr | $CH_2OCH_3$ | $CH_2OCH_2CH_3$ | $CH_2CH_2OCH_3$ |
| $CH_2SCH_3$ | $CH_2CH_2SCH_3$ | $CH_2CH_2CH_2S(O)_2CH_3$ | (c-pentyl)$CH_2$ |
| 2-Cl—Et | $CH_2CH_2OCH_2$C≡CH | $CH_2CH_2SCH_2$CH=$CH_2$ | (c-propyl)$CH_2$ |

TABLE 11-continued

Compounds of Formula I wherein: Q = O, $R^1$ = $CH_2$(tetrahydro-2-furanyl),

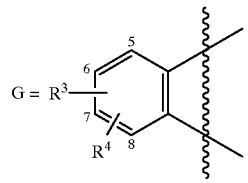

G = (structure with $R^3$ at position 6, $R^4$ at position 7/8, on a fused ring)

| | | | |
|---|---|---|---|
| (c-hexyl)$CH_2$ | $CH_2CH_2OCF_3$ | $CH_2SCH_2C\equiv CH$ | $CH_2CH_2CH_2CN$ |
| $CH_2CH_2Si(CH_3)_3$ | $CH_2CH_2CO_2Et$ | $CH_2OCH_2CH=CH_2$ | $CH_2OCH_2CH_2Cl$ |
| Ph | 4-Me—Ph | $CH_2CH_2CH_2N(CH_3)_2$ | 2-F—Ph |
| 4-MeO—Ph | $CH_2Ph$ | $CH_2CH_2OCH_2CH=CH_2$ | $CH_2CH_2Ph$ |
| $CH_2CH_2CH_2NHCH_3$ | $CH_2CH_2NO_2$ | —N=CHPh | $CH_2CH_2(4-F—Ph)$ |
| —N=CHCH_2CH_2CH_3 | —N=C(CH_3)_2 | NHCH_2CH_2CH_3 | N(CH_3)_2 |
| 2,4-diCl-Ph | 2,4,6-triF-Ph | 4-CF_3—Ph | 2-CN—Ph |
| $CH_2$(4-F—Ph) | —NHPh | —N(CH_3)Ph | $CH_2CH_2CH_2Ph$ |

W = S, $R^3$ = 6-I, $R^4$ = H,

| $R^2$ | $R^2$ | $R^2$ | $R^2$ |
|---|---|---|---|
| $CH_2CH_2CH_2F$ | t-Bu | i-Pr | n-Bu |
| i-Bu | s-Bu | n-pentyl | n-hexyl |
| n-decyl | c-hexyl | 2-propenyl | 2-butenyl |
| 3-butenyl | 5-decenyl | 2-propynyl | 2-butynyl |
| 3-butynyl | $CF_3$ | $CH_2CF_3$ | $CH_2CH=CHCl$ |
| $CH_2C\equiv CBr$ | $CH_2OCH_3$ | $CH_2OCH_2CH_3$ | $CH_2CH_2OCH_3$ |
| $CH_2SCH_3$ | $CH_2CH_2SCH_3$ | $CH_2CH_2S(O)_2CH_3$ | (c-pentyl)$CH_2$ |
| 2-Cl—Et | $CH_2CH_2OCH_2C\equiv CH$ | $CH_2CH_2SCH_2CH=CH_2$ | (c-propyl)$CH_2$ |
| (c-hexyl)$CH_2$ | $CH_2CH_2OCF_3$ | $CH_2SCH_2C\equiv CH$ | $CH_2CH_2CH_2CN$ |
| $CH_2CH_2Si(CH_3)_3$ | $CH_2CH_2CO_2Et$ | $CH_2OCH_2CH=CH_2$ | $CH_2OCH_2CH_2Cl$ |
| Ph | 4-Me—Ph | $CH_2CH_2CH_2N(CH_3)_2$ | 2-F—Ph |
| 4-MeO—Ph | $CH_2Ph$ | $CH_2CH_2OCH_2CH=CH_2$ | $CH_2CH_2Ph$ |
| $CH_2CH_2CH_2NHCH_3$ | $CH_2CH_2NO_2$ | —N=CHPh | $CH_2CH_2(4-F—Ph)$ |
| —N=CHCH_2CH_2CH_3 | —N=C(CH_3)_2 | NHCH_2CH_2CH_3 | N(CH_3)_2 |
| 2,4-diCl-Ph | 2,4,6-triF-Ph | 4-CF_3—Ph | 2-CN—Ph |
| $CH_2$(4-F—Ph) | —NHPh | —N(CH_3)Ph | $CH_2CH_2CH_2Ph$ |

W = O, $R^3$ = 6-I, $R^4$ = 8-I,

| $R^2$ | $R^2$ | $R^2$ | $R^2$ |
|---|---|---|---|
| $CH_2CH_2CH_2F$ | t-Bu | i-Pr | n-Bu |
| i-Bu | s-Bu | n-pentyl | n-hexyl |
| n-decyl | c-hexyl | 2-propenyl | 2-butenyl |
| 3-butenyl | 5-decenyl | 2-propynyl | 2-butynyl |
| 3-butynyl | $CF_3$ | $CH_2CF_3$ | $CH_2CH=CHCl$ |
| $CH_2C\equiv CBr$ | $CH_2OCH_3$ | $CH_2OCH_2CH_3$ | $CH_2CH_2OCH_3$ |
| $CH_2SCH_3$ | $CH_2CH_2SCH_3$ | $CH_2CH_2S(O)_2CH_3$ | (c-pentyl)$CH_2$ |
| 2-Cl—Et | $CH_2CH_2OCH_2C\equiv CH$ | $CH_2CH_2SCH_2CH=CH_2$ | (c-propyl)$CH_2$ |
| (c-hexyl)$CH_2$ | $CH_2CH_2OCF_3$ | $CH_2SCH_2C\equiv CH$ | $CH_2CH_2CH_2CN$ |
| $CH_2CH_2Si(CH_3)_3$ | $CH_2CH_2CO_2Et$ | $CH_2OCH_2CH=CH_2$ | $CH_2OCH_2CH_2Cl$ |
| Ph | 4-Me—Ph | $CH_2CH_2CH_2N(CH_3)_2$ | 2-F—Ph |
| 4-MeO—Ph | $CH_2Ph$ | $CH_2CH_2OCH_2CH=CH_2$ | $CH_2CH_2Ph$ |
| $CH_2CH_2CH_2NHCH_3$ | $CH_2CH_2NO_2$ | —N=CHPh | $CH_2CH_2(4-F—Ph)$ |
| —N=CHCH_2CH_2CH_3 | —N=C(CH_3)_2 | NHCH_2CH_2CH_3 | N(CH_3)_2 |
| 2,4-diCl-Ph | 2,4,6-triF-Ph | 4-CF_3—Ph | 2-CN—Ph |
| $CH_2$(4-F—Ph) | —NHPh | —N(CH_3)Ph | $CH_2CH_2CH_2Ph$ |

W = S, $R^3$ = 6-I, $R^4$ = 8-I,

| $R^2$ | $R^2$ | $R^2$ | $R^2$ |
|---|---|---|---|
| $CH_2CH_2CH_2F$ | t-Bu | n-Pr | n-Bu |
| i-Bu | s-Bu | n-pentyl | n-hexyl |
| n-decyl | c-hexyl | 2-propenyl | 2-butenyl |
| 3-butenyl | 5-decenyl | 2-propynyl | 2-butynyl |
| 3-butynyl | $CF_3$ | $CH_2CF_3$ | $CH_2CH=CHCl$ |
| $CH_2C\equiv CBr$ | $CH_2OCH_3$ | $CH_2OCH_2CH_3$ | $CH_2CH_2OCH_3$ |
| $CH_2SCH_3$ | $CH_2CH_2SCH_3$ | $CH_2CH_2CH_2S(O)_2CH_3$ | (c-pentyl)$CH_2$ |
| 2-Cl—Et | $CH_2CH_2OCH_2C\equiv CH$ | $CH_2CH_2SCH_2CH=CH_2$ | (c-propyl)$CH_2$ |
| (c-hexyl)$CH_2$ | $CH_2CH_2OCF_3$ | $CH_2SCH_2C\equiv CH$ | $CH_2CH_2CH_2CN$ |
| $CH_2CH_2Si(CH_3)_3$ | $CH_2CH_2CO_2Et$ | $CH_2OCH_2CH=CH_2$ | $CH_2OCH_2CH_2Cl$ |
| Ph | 4-Me—Ph | $CH_2CH_2CH_2N(CH_3)_2$ | 2-F—Ph |

TABLE 11-continued

Compounds of Formula I wherein: Q = O, R$^1$ = CH$_2$(tetrahydro-2-furanyl),

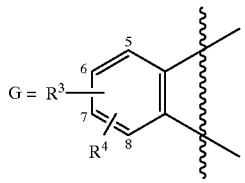

| | | | |
|---|---|---|---|
| 4-MeO—Ph | CH$_2$Ph | CH$_2$CH$_2$OCH$_2$CH=CH$_2$ | CH$_2$CH$_2$Ph |
| CH$_2$CH$_2$CH$_2$NHCH$_3$ | CH$_2$CH$_2$NO$_2$ | —N=CHPh | CH$_2$CH$_2$(4-F—Ph) |
| —N=CHCH$_2$CH$_2$CH$_3$ | —N=C(CH$_3$)$_2$ | NHCH$_2$CH$_2$CH$_3$ | N(CH$_3$)$_2$ |
| 2,4-diCl-Ph | 2,4,6-triF-Ph | 4-CF$_3$—Ph | 2-CN—Ph |
| CH$_2$(4-F—Ph) | —NHPh | —N(CH$_3$)Ph | CH$_2$CH$_2$CH$_2$Ph |

TABLE 12

Compounds of Formula I wherein W = Q = O and R$^1$ = CH$_2$ (tetrahydro-2-furanyl), R$^2$ = n-Pr,

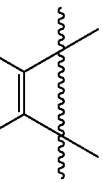

| R$^3$ | R$^4$ | R$^3$ | R$^4$ | R$^3$ | R$^4$ |
|---|---|---|---|---|---|
| 6-Cl | H | 6-Me | H | 6-Me$_3$Si | 8-Br |
| 6-Br | 8-Me | 6-Et | 8-Br | 6-Me$_2$N | H |
| 6-I | 8-Br | 6-MeO | H | 6-EtNH | H |
| 6-Cl | 8-Cl | 6-MeS | 8-MeO | 6-Br | 8-Me |
| 6-Br | 8-Cl | 6-SCH$_2$CH=CH$_2$ | H | 6-Br | 8-Et |
| 6-I | 8-I | 6-S(O)$_2$Me | H | 6-i-Pr | H |
| 6-C≡CH | H | 6-Br | 8-CF$_3$ | 6-Br | 8-OCF$_3$ |
| 6-C≡CH | 8-Br | 6-CH$_2$C≡CH | H | 6-CF$_3$O | H |
| H | H | 6-Br | 7-Br | 6-CH=CH$_2$ | H |
| 6-CF$_3$ | H | 6-CH$_2$CH=CH$_2$ | H | 6-Br | 7-Me |
| 6-CH$_2$Br | H | 6-Br | 5-Me | 6-Br | 5-Br |
| 6-CH=CHBr | H | 6-(CH$_3$)$_2$CH | H | 8-Br | H |
| 6-CH$_3$CH$_2$ | H | 6-I | 8-Me | 6-Me | 8-Br |

Formulation/Utility

Compounds of this invention will generally be used as a formulation or composition with an agriculturally suitable carrier comprising at least one of a liquid diluent, a solid diluent or a surfactant. The formulation or composition ingredients are selected to be consistent with the physical properties of the active ingredient, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredient can be (micro)encapsulated and further formed into a suspension or solid formulation; alternatively the entire formulation of active ingredient can be encapsulated (or "overcoated"). Encapsulation can control or delay release of the active ingredient. Sprayable formulations can be extended in suitable media and used at spray volumes from about one to several hundred liters per hectare. High-strength compositions are primarily used as intermediates for further formulation.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders. | 5–90 | 0–94 | 1–15 |
| Suspensions, Emulsions, Solutions (including Emulsifiable Concentrates) | 5–50 | 40–95 | 0–15 |
| Dusts | 1–25 | 70–99 | 0–5 |
| Granules and Pellets | 0.01–99 | 5–99.99 | 0–15 |
| High Strength Compositions | 90–99 | 0–10 | 0–2 |

Typical solid diluents are described in Watkins, et al., *Handbook of Insecticide Dust Diluents and Carriers*, 2nd Ed., Dorland Books, Caldwell, N.J. Typical liquid diluents are described in Marsden, *Solvents Guide*, 2nd Ed., Interscience, New York, 1950. *McCutcheon's Detergents and Emulsifiers Annual*, Allured Publ. Corp., Ridgewood, N.J., as well as Sisely and Wood, *Encyclopedia of Surface Active Agents*, Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, and polyoxyethylene/polyoxypropylene block copolymers. Solid diluents include, for example, clays such as bentonite, montmorillonite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformarnide, dimethyl sulfoxide, N-alkylpyrrolidone, ethylene glycol, polypropylene glycol, paraffins, alkylbenzenes, alkylnaphthalenes, oils of olive, castor, linseed, tung, sesame, corn, peanut, cotton-seed, soybean, rape-seed and coconut, fatty acid esters, ketones such as cyclohexanone, 2-heptanone, isophorone and 4-hydroxy-4-methyl-2-pentanone, and alcohols such as methanol, cyclohexanol, decanol and tetrahydrofurfuryl alcohol.

Solutions, including emulsifiable concentrates, can be prepared by simply mixing the ingredients. Dusts and powders can be prepared by blending and, usually, grinding as in a hammer mill or fluid-energy mill. Suspensions are usually prepared by wet-milling; see, for example, U.S. Pat. No. 3,060,084. Granules and pellets can be prepared by spraying the active material upon preformed granular carriers or by agglomeration techniques. See Browning, "Agglomeration", *Chemical Engineering*, Dec. 4, 1967, pp 147–48, *Perry's Chemical Engineer's Handbook*, 4th Ed., McGraw-Hill, New York, 1963, pages 8–57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see U.S. Pat. No. 3,235,361, Col. 6, line 16 through Col. 7, line 19 and Examples 10–41; U.S. Pat. No. 3,309,192, Col. 5, line 43 through Col. 7, line 62 and Examples 8, 12, 15, 39, 41, 52, 53, 58, 132, 138–140, 162–164, 166, 167 and 169–182; U.S. Pat. 2,891,855, Col. 3, line 66 through Col. 5, line 17 and Examples 1–4; Klingman, *Weed Control as a Science*, John Wiley and Sons, Inc., New York, 1961, pp 81–96; and Hance et al., *Weed Control Handbook*, 8th Ed., Blackwell Scientific Publications, Oxford, 1989.

In the following Examples, all percentages are by weight and all formulations are prepared in conventional ways. Compound numbers refer to compounds in Index Tables A–B.

Example A

| Wettable Powder | |
| --- | --- |
| Compound 37 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

Example B

| Granule | |
| --- | --- |
| Compound 41 | 10.0% |
| attapulgite granules (low volatile matter, 0.71/0.30 mm; U.S.S. No. 25–50 sieves) | 90.0%. |

Example C

| Extruded Pellet | |
| --- | --- |
| Compound 37 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Example D

| Emulsifiable Concentrate | |
| --- | --- |
| Compound 41 | 20.0% |
| blend of oil soluble sulfonates and polyoxyethylene ethers | 10.0% |
| isophorone | 70.0%. |

The compounds of this invention are useful as plant disease control agents. The present invention therefore further comprises a method for controlling plant diseases caused by fungal plant pathogens comprising applying to the plant or portion thereof to be protected, or to the plant seed or seedling to be protected, an effective amount of a compound of the invention or a fungicidal composition containing said compound. The compounds and compositions of this invention provide control of diseases caused by a broad spectrum of fungal plant pathogens in the Basidiomycete, Ascomycete, Oomycete and Deuteromycete classes. They are effective in controlling a broad spectrum of plant diseases, particularly foliar pathogens of ornamental, vegetable, field, cereal, and fruit crops. These pathogens include *Plasmopara viticola, Phytophthora infestans, Peronospora tabacina, Pseudoperonospora cubensis, Pythium aphanidermatum, Alternaria brassicae, Septoria nodorum, Septoria tritici, Cercosporidium personatum, Cercospora arachidicola, Pseudocercosporella herpotrichoides, Cercospora beticola, Botrytis cinerea, Moniliniafructicola, Pyricularia oryzae, Podosphaera leucotricha, Venturia inaequalis, Erysiphe graminis, Uncinula necatur, Puccinia recondita, Puccinia graminis, Hemileia vastatrix, Puccinia striiformis, Puccinia arachidis, Rhizoctonia solani, Sphaerothecafuliginea, Fusarium oxysporum, Verticillium dahliae, Pythium aphanidennatum, Phytophthora megasperma, Sclerotinia sclerotiorum, Sclerotium rolfsii, Erysiphe polygoni, Pyrenophora teres, Gaeumannomyces graminis, Rynchosporium secalis, Fusarium roseum, Bremia lactucae* and other generea and species closely related to these pathogens.

Compounds of this invention can also be mixed with one or more other insecticides, fungicides, nematocides, bactericides, acaricides, growth regulators, chemosterilants, semiochemicals, repellents, attractants, pheromones, feeding stimulants or other biologically active compounds to form a multi-component pesticide giving an even broader spectrum of agricultural protection. Examples of such agricultural protectants with which compounds of this invention can be formulated are: insecticides such as abamectin, acephate, azinphos-methyl, bifenthrin, buprofezin, carbofuran, chlorpyrifos, chlorpyrifos-methyl, cyfluthrin, beta-cyfluthrin, deltamethrin, diafenthiuron, diazinon, diflubenzuron, dimethoate, esfenvalerate, fenpropathrin, fenvalerate, fipronil, flucythrinate, tau-fluvalinate, fonophos, imidacloprid, isofenphos, malathion, metaldehyde, methamidophos, methidathion, methomyl, methoprene, methoxychlor, monocrotophos, oxamyl, parathion, parathion-methyl, permethrin, phorate, phosalone, phosmet, phosphamidon, pirimicarb, profenofos, rotenone, sulprofos, tebufenozide, tefluthrin, terbufos, tetrachlorvinphos, thiodicarb, tralomethrin, trichlorfon and triflumuron; fungicides such as azoxystrobin (ICIA5504), benomyl, blasticidin-S, Bordeaux mixture (tribasic copper sulfate), bromuconazole, captafol, captan, carbendazim, chloroneb, chlorothalonil, copper oxychloride, copper salts, cymoxanil, cyproconazole, cyprodinil (CGA 219417), diclomezine, dicloran, difenoconazole, dimethomorph, diniconazole, diniconazole-M, dodine, edifenphos, epoxiconazole (BAS 480F), fenarimol, fenbuconazole, fenpiclonil, fenpropidin, fenpropimorph, fluazinam, fluquinconazole, flusilazole, flutolanil, flutriafol, folpet, fosetyl-aluminum, furalaxyl, hexaconazole, ipconazole, iprobenfos, iprodione, isoprothiolane, kasugamycin, kresoxim-methyl (BAS 490F), mancozeb, maneb, mepronil, metalaxyl, metconazole, S-methyl 7-benzothiazolecarbothioate (CGA 245704), 5-methyl-5-(4-phenoxyphenyl)-3-phenylamino-2,4-oxazolidinedione (DPX-JE874), myclobutanil, neo-asozin (ferric methanearsonate), oxadixyl, penconazole, pencycuron, probenazole, prochloraz, propiconazole, pyrifenox, pyroquilon, sulfur, tebuconazole, tetraconazole, thiabendazole, thiophanate-methyl, thiram, triadimefon, triadimenol, tricyclazole, triticonazole, uniconazole, validamycin and vinclozolin; nematocides such as aldoxycarb and fenamiphos; bactericides such as streptomycin; acaricides such as amitraz, chinomethionat, chlorobenzilate, cyhexatin, dicofol, dienochlor, fenazaquin, fenbutatin oxide, fenpropathrin, fenpyroximate, hexythiazox, propargite, pyridaben and tebufenpyrad; and biological agents such as *Bacillus thuringiensis, Bacillus thuringiensis* delta endotoxin, baculovirus, and entomopathogenic bacteria, virus and fungi.

In certain instances, combinations with other fungicides having a similar spectrum of control but a different mode of action will be particularly advantageous for resistance management.

Preferred for better control of plant diseases caused by fungal plant pathogens (e.g., lower use rate or broader spectrum of plant pathogens controlled) or resistance management are mixtures of a compound of this invention with a fungicide selected from the group azoxystrobin (ICIA5504), benomyl, captan, carbendazim, cymoxanil, cyproconazole, cyprodinil (CGA 219417), difenoconazole, epoxiconazole (BAS 480F), fenpropidin, fenpropimorph, fluazinam, flusilazole, hexaconazole, kresoxim-methyl (BAS 490F), mancozeb, maneb, metalaxyl, S-methyl 7-benzothiazolecarbothioate (CGA 245704), 5-methyl-5-(4-phenoxyphenyl)-3-phenylamino-2,4-oxazolidinedione (DPX-JE874), myclobutanil, penconazole, prochloraz, tebuconazole and tetraconazole. Specifically preferred mixtures (compound numbers refer to compounds in Index Tables A–B) are selected from the group: compound 37 and azoxystrobin (ICIA5504); compound 37 and benomyl; compound 37 and captan; compound 37 and carbendazim; compound 37 and cymoxanil; compound 37 and cyproconazole; compound 37 and cyprodinil (CGA 219417); compound 37 and difenoconazole; compound 37 and epoxiconazole (BAS 480F); compound 37 and fenpropidin; compound 37 and fenpropimorph; compound 37 and fluazinam; compound 37 and flusilazole; compound 37 and hexaconazole; compound 37 and kresoxim-methyl (BAS 490F); compound 37 and mancozeb; compound 37 and maneb; compound 37 and metalaxyl; compound 37 and S-methyl 7-benzothiazolecarbothioate (CGA 245704); compound 37 and 5-methyl-5-(4-phenoxyphenyl)-3-phenylamino-2,4-oxazolidinedione (DPX-JE874); compound 37 and myclobutanil; compound 37 and penconazole; compound 37 and prochloraz; compound 37 and tebuconazole; compound 37 and tetraconazole; compound 41 and azoxystrobin (ICIA5504); compound 41 and benomyl; compound 41 and captan; compound 41 and carbendazim; compound 41 and cymoxanil; compound 41 and cyproconazole; compound 41 and cyprodinil (CGA 219417); compound 41 and difenoconazole; compound 41 and epoxiconazole (BAS 480F); compound 41 and fenpropidin; compound 41 and fenpropimorph; compound 41 and fluazinam; compound 41 and flusilazole; compound 41 and hexaconazole; compound 41 and kresoxim-methyl (BAS 490F); compound 41 and mancozeb; compound 41 and maneb; compound 41 and metalaxyl; compound 41 and S-methyl 7-benzothiazolecarbothioate (CGA 245704); compound 41 and 5-methyl-5-(4-phenoxyphenyl)-3-phenylamino-2,4-oxazolidinedione (DPX-JE874); compound 41 and myclobutanil; compound 41 and penconazole; compound 41 and prochloraz; compound 41 and tebuconazole; and compound 41 and tetraconazole.

Plant disease control is ordinarily accomplished by applying an effective amount of a compound of this invention either pre- or post-infection, to the portion of the plant to be protected such as the roots, stems, foliage, fruit, seeds, tubers or bulbs, or to the media (soil or sand) in which the plants to be protected are growing. The compounds can also be applied to the seed to protect the seed and seedling.

Rates of application for these compounds can be influenced by many factors of the environment and should be determined under actual use conditions. Foliage can normally be protected when treated at a rate of from less than 1 g/ha to 5,000 g/ha of active ingredient. Seed and seedlings can normally be protected when seed is treated at a rate of from 0.1 to 10 g per kilogram of seed.

The following TESTS demonstrate the control efficacy of compounds of this invention on specific pathogens. The pathogen control protection afforded by the compounds is not limited, however, to these species. See Index Tables A–B for compound descriptions. The following abbreviations are used in the Index Tables which follow: i=iso, c=cyclo, Me=methyl, Et=ethyl, Pr=propyl, i-Pr=isopropyl, Ph=phenyl, and piper=1-piperidinyl. The abbreviation "Ex." stands for "Example" and is followed by a number indicating in which example the compound is prepared.

INDEX TABLE A
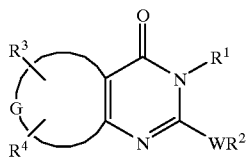
Compounds of Formula Ii
| Cmpd No. | (ring) | R¹ | WR² | m.p.(°C.) |
|---|---|---|---|---|
| 1 | 5-Cl-phenyl | $CH_2CH_2CH_3$ | $OCH_2$-(3-pyridyl) | 100–103 |
| 2 Ex. 10 | 5-Br-phenyl | $CH_2CH_2CH_3$ | $OCH_2$-(3-pyridyl) | 120–124 |
| 3 Ex. 4 | naphthyl | $CH_2CH_2CH_3$ | $SCH_3$ | 143–145 |
| 4 Ex. 5 | naphthyl | $CH_2CH_2CH_3$ | $OCH_2CH_2CH_3$ | 76–79.5 |
| 5 Ex. 3 | 5-Br-pyridyl | $CH_2CH_2CH_3$ | $OCH_2CH_2CH_3$ | 100–103 |
| 6 | 5-Br-pyridyl | $CH_2CH_2CH_3$ | $SCH_2CH_2CH_3$ | 114–117 |

INDEX TABLE A-continued
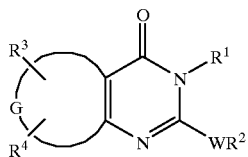
Compounds of Formula Ii
| Cmpd No. | (ring) | R¹ | WR² | m.p.(°C.) |
|---|---|---|---|---|
| 7 Ex. 2 | 5-Br-pyridin-2,3-diyl | $CH_2CH_2CH_3$ | $SCH_3$ | 124–127 |
| 8 | 4-Br-phenyl-1,2-diyl | $CH_2CH_2CH_3$ | 3-(OCH₂-)-1-methylpyridinium I⁻ | 152–155 |
| 9 | 4-Br-phenyl-1,2-diyl | $CH_2CH_2CH_3$ | 3-(OCH₂-)-pyridinium Cl⁻ | 235–238 |
| 10 Ex. 8 | 4-Br-phenyl-1,2-diyl | $CH_2$-oxiranyl | $OCH_2CH_2CH_3$ | 84–87 |
| 11 | 4-I-phenyl-1,2-diyl | $CH_2$-(2-furyl) | $OCH_2CH_2CH_3$ | 112–114 |

INDEX TABLE A-continued
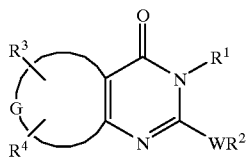
Compounds of Formula Ii
| Cmpd No. | (R³/G/R⁴ group) | R¹ | WR² | m.p.(°C.) |
|---|---|---|---|---|
| 12 | Br-phenyl | CH₂-furan-2-yl | OCH₂CH₂CH₃ | 118–121 |
| 13 Ex. 7 | Br-phenyl | CH₂-tetrahydrofuran-2-yl | OCH₂CH₂CH₃ | 83–85 |
| 14 Ex. 8 | Br-phenyl | CH₂-(3-CO₂Et-isoxazolin-5-yl) | OCH₂CH₂CH₃ | 139–141 |
| 15 | Br-phenyl | CH₂-(3-Br-isoxazolin-5-yl) | OCH₂CH₂CH₃ | 75–76 |
| 16 | i-PrO-thiophene | CH₂CH₂CH₃ | SCH₃ | oil* |
| 17 Ex. 1 | Br-thiophene | CH₂CH₂CH₃ | SCH₃ | 146–147 |

INDEX TABLE A-continued
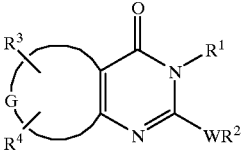
Compounds of Formula Ii
| Cmpd No. | 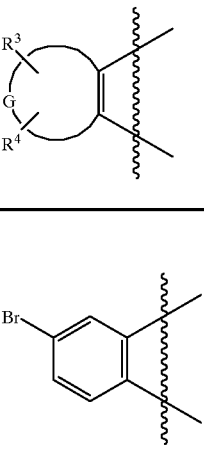 | R¹ | WR² | m.p.(°C.) |
|---|---|---|---|---|
| 18 | 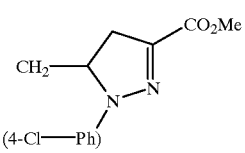 Br | 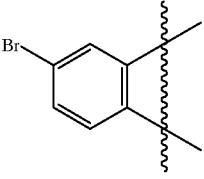 CH₂—[pyrazole with CO₂Me, N-(4-Cl—Ph)] | $OCH_2CH_2CH_3$ | 167–169 |
| 19 | 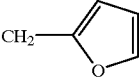 Br | CH₂—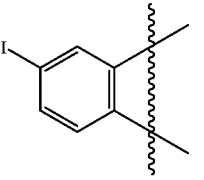 (furan) | $SCH_3$ | 136–140 |
| 20 | 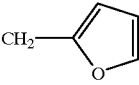 I | CH₂—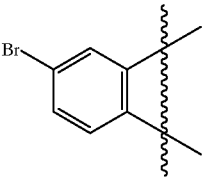 (furan) | $SCH_3$ | 143–147 |
| 21 Ex. 6 | 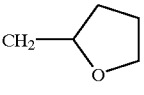 Br | CH₂—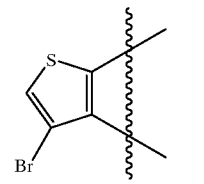 (tetrahydrofuran) | $SCH_3$ | 68–72 |
| 22 | (thiophene with Br) | $CH_2CH_2CH_3$ | $OCH_2CH_2CH_3$ | 67–70 |

INDEX TABLE A-continued
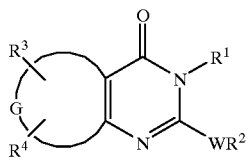
Compounds of Formula Ii
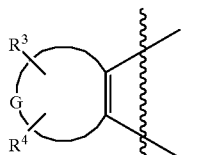
| Cmpd No. | | R¹ | WR² | m.p.(°C.) |
|---|---|---|---|---|
| 23 | Br—[thiophene with Br]— | CH₂CH₂CH₃ | OCH₂CH₂CH₃ | 94–96 |
| 24 | [thiophene with Br]— | CH₂CH₂CH₃ | NHCH₂CH₂CH₃ | 162–165 |
| 25 | Br—[thiophene with Br]— | CH₂CH₂CH₃ | NHCH₂CH₂CH₃ | 162–164 |
| 26 | Br—[phenyl]— | CH₂—[tetrahydrofuran] | SCH₂CH₂CH₃ | 98–100 |
| 27 | I—[phenyl]— | CH₂CH₂CH₃ | SCH₂CH₂—[1,3-dioxolane] | 114–116 |
| 28 | I—[phenyl]— | CH₂CH₂CH₃ | SCH₂—[thiophene-Cl] | 115–117 |

INDEX TABLE A-continued

Compounds of Formula Ii

| Cmpd No. | (ring with R³, G, R⁴) | R¹ | WR² | m.p.(°C.) |
|---|---|---|---|---|
| 29 | 4-I-phenyl (ortho-fused) | CH₂-(3-pyridyl) | SCH₂CH₂CH₃ | 127–129 |
| 30 | 4-I-phenyl (ortho-fused) | CH₂-(tetrahydrofuran-2-yl) | SCH₂CH₂CH₃ | 91–96 |
| 31 | 4-I-phenyl (ortho-fused) | CH₂CH₂CH₃ | SCH₂-(3-Br-4,5-dihydroisoxazol-5-yl) | oil* |
| 32 | 4-I-phenyl (ortho-fused) | CH₂CH₂CH₃ | SCH₂-(3-Br-4,5-dihydroisoxazol-5-yl) | 117–120 |
| 33 | 4-I-phenyl (ortho-fused) | CH₂-(3-CONMe₂-4,5-dihydroisoxazol-5-yl) | SCH₂CH₂CH₃ | 160–162 |

INDEX TABLE A-continued

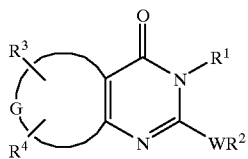

Compounds of Formula Ii

| Cmpd No. | (R³/G/R⁴ ring group) | R¹ | WR² | m.p.(°C.) |
|---|---|---|---|---|
| 34 | 4-iodophenyl (1,2-attached) | CH₂-(5-position of 4,5-dihydroisoxazol-3-yl with 3-CO(piper)) | SCH₂CH₂CH₃ | 154–156 |
| 35 | 4-iodophenyl (1,2-attached) | CH₂CH₂CH₃ | SCH₂-(5-position of 3-Br-4,5-dihydroisoxazol-5-yl) | 150–152 |
| 36 | 3,5-diiodophenyl (1,2-attached) | CH₂-(5-position of 3-Br-4,5-dihydroisoxazol-5-yl) | SCH₂CH₂CH₃ | 158–160 |
| 37 Ex. 12 | 3,5-diiodophenyl (1,2-attached) | CH₂-(2-tetrahydrofuranyl) | SCH₂CH₂CH₃ | 108–111 |
| 38 | 5-bromopyridin-2,3-diyl | CH₂(c-propyl) | SCH₂CH₂CH₃ | 108–110 |

INDEX TABLE A-continued

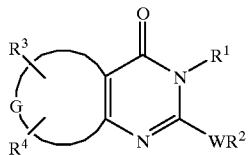

Compounds of Formula Ii

| Cmpd No. | 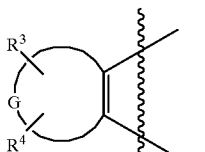 | R$^1$ | WR$^2$ | m.p.(°C.) |
|---|---|---|---|---|
| 39 | Br-[5-bromopyridin-2,3-diyl] | CH$_2$CH(CH$_3$)$_2$ | SCH$_2$CH$_2$CH$_3$ | 105–107 |
| 40 | I-[5-iodopyridin-2,3-diyl] | CH$_2$CH(CH$_3$)$_2$ | SCH$_2$CH$_2$CH$_3$ | 109–111 |
| 41 Ex. 11 | I-[5-iodopyridin-2,3-diyl] | CH$_2$(c-propyl) | SCH$_2$CH$_2$CH$_3$ | 159–161 |
| 42 | I-[5-iodopyridin-2,3-diyl] | CH$_2$CH$_2$CH$_2$OCH$_3$ | SCH$_2$CH$_2$CH$_3$ | 103–106 |
| 43 | I-[5-iodopyridin-2,3-diyl] | CH$_2$-(tetrahydrofuran-2-yl) | SCH$_2$CH$_2$CH$_3$ | 149–152 |
| 44 | Br-[4-bromophenyl-1,2-diyl] | CH$_2$-(furan-2-yl) | SCH$_2$CH$_2$CH$_3$ | 95–98 |

INDEX TABLE A-continued
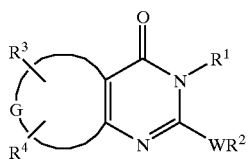
Compounds of Formula Ii
| Cmpd No. | | R¹ | WR² | | m.p.(°C.) |
|---|---|---|---|---|---|
| 45 | ![I-phenyl] | CH₂-furan | SCH₂CH₂CH₃ | | 107–109 |
| 46 | ![diiodo-phenyl] | CH₂-furan | SCH₂CH₂CH₃ | | 160–162 |
| 47 | ![difluoro-phenyl] | CH₂-furan | SCH₂CH₂CH₃ | | 85–86 |
| 48 | ![difluoro-phenyl] | CH₂-furan | SCH₂CH₂-dioxolane | | 70–73 |
| 49 | ![diiodo-phenyl] | CH₂-furan | SCH₂CH₂-dioxolane | | 124–127 |

INDEX TABLE A-continued

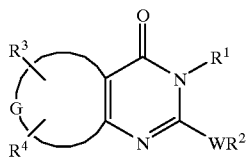

Compounds of Formula Ii

| Cmpd No. | | R[1] | WR[2] | m.p.(°C.) |
|---|---|---|---|---|
| 50 | 3,5-diiodophenyl (fused) | CH₂-(tetrahydrofuran-2-yl) | SCH₃ | 170–172 |
| 51 | 4-iodophenyl (fused) | CH₂-(tetrahydrofuran-2-yl) | SCH₃ | 105–107 |
| 52 | 3,5-diiodophenyl (fused) | CH₂-(furan-2-yl) | SCH₃ | 210–212 |
| 53[a] | 4-iodophenyl (fused) | CH₂-(tetrahydrofuran-2-yl) | OCH₂CH₂CH₃ | 97–98 |
| 54[b] | 4-iodophenyl (fused) | CH₂-(tetrahydrofuran-2-yl) | OCH₂CH₂CH₃ | 97–98 |

*See Index Table B for ¹H NMR data.
[a]Compound is the S-isomer.
[b]Compound is the R-isomer.

INDEX TABLE B

| Cmpd No. | $^1$H NMR Data (CDCl$_3$ solution unless indicated otherwise)[a] |
|---|---|
| 16 | δ7.43 (s,1H), 5.39 (m,1H), 4.20 (t,2H), 2.34 (s,3H), 1.72 (m,2H), 1.47 (s,3H), 1.45 (s,3H), 0.99 (t,3H). |
| 31 | δ1.02 (t,3H), 1.70–1.84 (m,2H), 3.20 (dd,1H), 3.38 (dd,1H), 3.53 (dd,1H), 3.70 (dd,1H), 4.07 (t,2H), 5.02–5.18 (m,1H), 7.24 (d,1H), 7.96 (dd,1H), 8.54 (d,1H). |

[a] $^1$H NMR data are in ppm downfield from tetramethylsilane. Couplings are designated by (s)—singlet, (d)—doublet, (t)—triplet, (m)—multiplet, (dd)—doublet of doublets.

BIOLOGICAL EXAMPLES OF THE INVENTION

Test compounds were first dissolved in acetone in an amount equal to 3% of the final volume and then suspended at a concentration of 200 ppm in purified water containing 250 ppm of the surfactant Trem® 014 (polyhydric alcohol esters). The resulting test suspensions were then used in the following tests. Spraying these 200 ppm test suspensions to the point of run-off on the test plants is the equivalent of a rate of 500 g/ha.

TEST A

The test suspension was sprayed to the point of run-off on wheat seedlings. The following day the seedlings were inoculated with a spore dust of *Erysiphe graminis f. sp. tritici*, (the causal agent of wheat powdery mildew) and incubated in a growth chamber at 20° C. for 7 days, after which disease ratings were made.

TEST B

The test suspension was sprayed to the point of run-off on wheat seedlings. The following day the seedlings were inoculated with a spore suspension of *Puccinia recondita* (the causal agent of wheat leaf rust) and incubated in a saturated atmosphere at 20° C. for 24 h, and then moved to a growth chamber at 20° C. for 6 days, after which disease ratings were made.

TEST C

The test suspension was sprayed to the point of run-off on tomato seedlings. The following day the seedlings were inoculated with a spore suspension of *Phytophthora infestans* (the causal agent of potato and tomato late blight) and incubated in a saturated atmosphere at 20° C. for 24 h, and then moved to a growth chamber at 20° C. for 5 days, after which disease ratings were made.

TEST D

The test suspension was sprayed to the point of run-off on grape seedlings. The following day the seedlings were inoculated with a spore suspension of *Plasmopara viticola* (the causal agent of grape downy mildew) and incubated in a saturated atmosphere at 20° C. for 24 h, moved to a growth chamber at 20° C. for 6 days, and then incubated in a saturated atmosphere at 20° C. for 24 h, after which disease ratings were made.

TEST E

The test suspension was sprayed to the point of run-off on cucumber seedlings. The following day the seedlings were inoculated with a spore suspension of *Botrytis cinerea* (the causal agent of gray mold on many crops) and incubated in a saturated atmosphere at 20° C. for 48 h, and moved to a growth chamber at 20° C. for 5 days, after which disease ratings were made.

TEST F

The test suspension was sprayed to the point of run-off on cucumber seedlings. The following day the seedlings were inoculated with a spore suspension of *Erysiphe cichoracearum* (the causal agent of cucumber powdery mildew) and moved to a greenhouse for 7 days. Disease ratings were made 7 days following application of the test compounds.

Results for Tests A–F are given in Table A. In the table, a rating of 100 indicates 100% disease control and a rating of 0 indicates no disease control (relative to the controls). A dash (-) indicates no test results.

TABLE A

| Cmpd No. | Test A | Test B | Test C | Test D | Test E | Test F |
|---|---|---|---|---|---|---|
| 1 | 99* | 61 | 0 | 41 | 0 | 100 |
| 2 | 100* | 12 | 0 | 17 | 0 | — |
| 3 | 53* | 0 | 0 | 14 | 37 | — |
| 4 | 76* | 0 | 26 | 39 | 0 | — |
| 5 | 100* | 0 | 26 | 22 | 14 | 100* |
| 6 | 100* | 0 | 26 | 0 | 71 | 100* |
| 7 | 92* | 0 | 26 | 44 | 14 | 52* |
| 8 | 81* | 91 | 24 | 10 | 0 | 100 |
| 9 | 85* | 0 | 0 | 10 | 0 | 100 |
| 10 | 99* | 0 | 0 | 41 | 0 | — |
| 11 | 100* | 2 | 0 | 83 | 0 | 100 |
| 12 | 98* | 2 | 0 | 8 | 0 | 100 |
| 13 | 100* | 56 | 0 | 34 | 0 | 100 |
| 14 | 95* | 56 | 0 | 0 | 0 | 100 |
| 15 | 97* | 2 | 0 | 34 | 0 | 100 |
| 16 | 0* | 0 | 0 | 55 | 0 | — |
| 17 | 28* | 9 | 47 | 99 | 0 | 46* |
| 18 | 90 | 19 | 0 | 36 | 0 | — |
| 19 | 75* | 0 | 0 | 23 | 0 | — |
| 20 | 68* | 0 | 0 | 62 | 0 | — |
| 21 | 99* | 0 | 0 | 92 | 0 | — |
| 22 | 88* | 66 | 0 | 18 | 0 | — |
| 23 | 100* | 66 | 0 | 0 | 4 | — |
| 24 | 9* | 25 | 47 | 18 | 68 | — |
| 25 | 74* | 0 | 47 | 0 | 9 | 64* |
| 26 | 100* | 41 | 0 | 72 | 0 | 100* |
| 27 | 100* | 41 | 0 | 12 | 0 | 11* |
| 28 | 98* | 0 | 0 | 0 | 0 | 70* |
| 29 | 47* | 41 | 0 | 72 | 0 | 0* |
| 30 | 100* | 74 | 0 | 72 | 0 | 100* |
| 31 | 100* | 0 | 0 | 91 | 8 | 100* |
| 32 | 89* | 0 | 25 | 0 | 47 | 90* |
| 33 | 0* | 0 | 0 | — | 0 | 70* |
| 34 | 40* | 0 | 25 | — | 47 | 9* |
| 35 | 0* | 0 | 22 | — | 0 | — |
| 36 | 78* | 0 | 22 | — | 0 | — |
| 37 | 100* | 0 | 22 | — | 0 | — |
| 38 | 100* | 0 | 0 | — | 0 | — |
| 39 | 99* | 0 | 0 | — | 0 | — |
| 40 | 100* | 26 | 0 | — | 0 | — |
| 41 | 100* | 0 | 0 | — | 0 | — |
| 42 | 100* | 85 | 0 | — | 0 | — |
| 43 | 100* | 0 | 0 | — | 0 | — |
| 44 | 92* | 0 | 11 | — | 0 | — |
| 45 | 77* | 24 | 0 | — | 0 | — |
| 46 | 74* | 0 | 0 | — | 0 | — |
| 47 | 0* | 24 | 0 | — | 0 | — |
| 48 | 45* | 23 | 10 | — | 68 | — |
| 49 | 67* | 23 | 10 | — | 94 | — |
| 50 | 97* | 23 | 10 | — | 44 | — |
| 51 | 100* | 65 | 10 | — | 68 | — |
| 52 | 97* | 23 | 0 | — | 0 | — |

TABLE A-continued

| Cmpd No. | Test A | Test B | Test C | Test D | Test E | Test F |
|---|---|---|---|---|---|---|
| 53 | 100* | — | — | — | — | — |
| 54 | 100* | — | — | — | — | — |

*Test was run at 10 ppm.

What is claimed is:

1. A compound selected from Formula I, N-oxides and agriculturally suitable salts thereof,

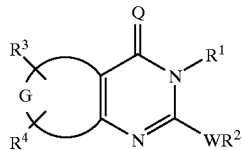

I wherein

W is O, S(O)$_n$ or NR$^5$;

n is 0, 1 or 2;

Q is O or S;

G is a fused thiophene or furan ring;

R$^1$ is C$_1$–C$_{10}$ alkyl; C$_3$–C$_6$ cycloalkyl; C$_3$–C$_{10}$ alkenyl; C$_3$–C$_{10}$ alkynyl; C$_1$–C$_{10}$ haloalkyl; C$_3$–C$_{10}$ haloalkenyl; C$_3$–C$_{10}$ haloalkynyl; C$_2$–C$_{10}$ alkoxyalkyl; C$_2$–C$_{10}$ alkylthioalkyl; C$_2$–C$_{10}$ alkylsulfonylalkyl; C$_4$–C$_{10}$ cycloalkylalkyl; C$_4$–C$_{10}$ alkenyloxyalkyl; C$_4$–C$_{10}$ alkynyloxyalkyl; C$_4$–C$_{10}$ alkenylthioalkyl; C$_4$–C$_{10}$ alkynylthioalkyl; C$_2$–C$_{10}$ haloalkoxyalkyl; C$_4$–C$_{10}$ alkoxyalkenyl; C$_4$–C$_{10}$ alkylthioalkenyl; C$_4$–C$_{10}$ trialkylsilylalkyl; C$_1$–C$_{10}$ alkoxy; NR$^6$R$^7$; R$^{11}$; phenyl, pyridinyl, furanyl, thienyl, naphthalenyl, benzofuranyl, benzo[b]thiophenyl or quinolinyl each optionally substituted with R$^8$, R$^9$ and R$^{10}$; or C$_1$–C$_{10}$ alkyl substituted with NR$^6$R$^7$, nitro, cyano, CO$_2$R$^6$ or phenyl optionally substituted with R$^8$, R$^9$ and R$^{10}$;

R$^2$ is C$_1$–C$_{10}$ alkyl; C$_3$–C$_7$ cycloalkyl; C$_3$–C$_{10}$ alkenyl; C$_3$–C$_{10}$ alkynyl; C$_1$–C$_{10}$ haloalkyl; C$_3$–C$_{10}$ haloalkenyl; C$_3$–C$_{10}$ haloalkynyl; C$_2$–C$_{10}$ alkoxyalkyl; C$_2$–C$_{10}$ alkylthioalkyl; C$_2$–C$_{10}$ alkylsulfonylalkyl; C$_4$–C$_{10}$ cycloalkylalkyl; C$_4$–C$_{10}$ alkenyloxyalkyl; C$_4$–C$_{10}$ alkynyloxyalkyl; C$_4$–C$_{10}$ alkenylthioalkyl; C$_4$–C$_{10}$ alkynylthioalkyl; C$_2$–C$_{10}$ haloalkoxyalkyl; C$_4$–C$_{10}$ alkoxyalkenyl; C$_4$–C$_{10}$ alkylthioalkenyl; C$_4$–C$_{10}$ trialkylsilylalkyl; R$^{11}$; phenyl optionally substituted with R$^8$, R$^9$ and R$^{10}$; or C$_1$–C$_{10}$ alkyl substituted with NR$^6$R$^7$, cyano, nitro, CO$_2$R$^6$, or phenyl optionally substituted with R$^8$, R$^9$ and R$^{10}$; or when W is NR$^5$, then R$^2$ can additionally be selected from —OR$^7$; —N=CR$^6$R$^6$; —NR$^6$R$^7$; and pyridinyl, furanyl, thienyl and naphthalenyl each optionally substituted with R$^8$, R$^9$ and R$^{10}$; or when W is O, then R$^2$ can additionally be selected from —N=CR$^6$R$^6$ and —NR$^6$R$^7$;

R$^3$ is hydrogen; halogen; C$_1$–C$_8$ alkyl; C$_3$–C$_8$ cycloalkyl; C$_2$–C$_8$ alkenyl; C$_2$–C$_8$ alkynyl; C$_1$–C$_8$ haloalkyl; C$_3$–C$_8$ haloalkenyl; C$_3$–C$_8$ haloalkynyl; C$_1$–C$_8$ alkoxy; C$_1$–C$_8$ haloalkoxy; C$_3$–C$_8$ alkenyloxy; C$_3$–C$_8$ alkynyloxy; C$_1$–C$_8$ alkylthio; C$_1$–C$_8$ alkylsulfonyl; C$_2$–C$_8$ alkoxyalkyl; C$_3$–C$_8$ trialkylsilyl; nitro; NR$^6$R$^7$; C$_5$–C$_8$ trialkylsilylalkynyl; or phenyl optionally substituted with at least one R$^{13}$;

R$^4$ is hydrogen, halogen, C$_1$–C$_4$ alkyl, C$_1$–C$_4$ haloalkyl, C$_1$–C$_4$ alkoxy or C$_1$–C$_4$ haloalkoxy;

R$^5$ is hydrogen, C$_1$–C$_4$ alkyl or —C(=O)R$^{12}$;

each R$^6$ is independently hydrogen; C$_1$–C$_4$ alkyl; or phenyl optionally substituted with at least one R$^{13}$;

each R$^7$ is independently hydrogen; C$_1$–C$_8$ alkyl; or phenyl optionally substituted with at least one R$^{13}$; or each pair of R$^6$ and R$^7$, when attached to the same nitrogen atom, can independently be taken together as —CH$_2$CH$_2$CH$_2$CH$_2$—, —CH$_2$(CH$_2$)$_3$CH$_2$—, —CH$_2$CH$_2$OCH$_2$CH$_2$—, —CH$_2$CH(Me)CH$_2$CH(Me)CH$_2$— or —CH$_2$CH(Me)OCH(Me)CH$_2$—;

each R$^8$ is independently C$_1$–C$_6$ alkyl; C$_1$–C$_6$ alkoxy; C$_1$–C$_6$ haloalkyl; halogen; C$_2$–C$_8$ alkynyl; C$_1$–C$_6$ alkylthio; phenyl or phenoxy each optionally substituted with at least one R$^{13}$; cyano; nitro; C$_1$–C$_6$ haloalkoxy; C$_1$–C$_6$ haloalkylthio; C$_2$–C$_6$ alkenyl; C$_2$–C$_6$ haloalkenyl; acetyl; CO$_2$Me; or N(C$_1$–C$_2$ alkyl)$_2$;

each R$^9$ is independently methyl, ethyl, methoxy, methylthio, halogen, CO$_2$(C$_1$–C$_3$ alkyl), C(O)NR$^6$R$^7$ or trifluoromethyl;

each R$^{10}$ is independently halogen;

each R$^{11}$ is independently C$_1$–C$_{10}$ alkyl substituted with an 8-, 9- or 10-membered fused carbobicyclic or fused heterobicyclic ring; or R$^{11}$ is C$_1$–C$_{10}$ alkyl substituted with a 3-, 4-, 5- or 6-membered heteromonocyclic ring; wherein said heterobicyclic or heteromonocyclic rings contain 1 to 4 heteroatoms independently selected from the group nitrogen, oxygen and sulfur, provided that each heterobicyclic or heteromonocyclic ring contains no more than 4 nitrogens, no more than 2 oxygens and no more than 2 sulfurs, wherein said heterobicyclic or heteromonocyclic ring is bonded to the alkyl group through a carbon atom of the ring, and wherein said carbobicyclic, heterobicyclic or heteromonocyclic ring is optionally substituted with R$^8$, R$^9$ and R$^{10}$;

R$^{12}$ is hydrogen, C$_1$–C$_4$ alkyl, C$_1$–C$_4$ alkoxy or NR$^6$R$^7$; and each R$^{13}$ is independently halogen, C$_1$–C$_4$ alkyl, C$_1$–C$_4$ alkoxy, C$_1$–C$_4$ haloalkyl, nitro or cyano;

provided that when G is a fused thiophene ring, then R$^3$ is other than hydrogen, C$_1$–C$_8$ alkyl, nitro or phenyl optionally substituted with at least one R$^{13}$.

2. A compound of claim 1 wherein Q is O, R$^1$ and R$^2$ are n-propyl and W is O.

3. A compound of claim 2 wherein (1) G is

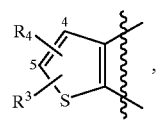

R$^1$ and R$^2$ are n-propyl, and

R$^3$ and R$^4$ are selected from the group consisting of (i) R$^3$ is 4-Br, 4-Cl, 4-I, 5-Br, 5-C≡-CSiMe$_3$, 4-C≡CH, 5-I, 4-CF$_3$, 4-c-propyl, 5-C≡CH, 4CH=CH$_2$, or 5-CH=CH$_2$ and R$^4$ is H; (ii) R$^3$ is 4-I and R$^4$ is 5-I or 5-Et; (iii) R$^3$ is 4-Br and R$^4$ is 5-Br; (iv) R$^3$ is 5-C≡CH and R$^4$ is 4-Br; and (v) R$^3$ is 5-Br and R$^4$ is 4-Me;

(2) G is

[structure: thiophene ring with R4 at 5-position, R3 at 4-position, S]

R$^1$ and R$^2$ are n-propyl, and
R$^3$ and R$^4$ are selected from the group consisting of (i) R$^3$ is 4-Br, 4-Cl, 4-I, 5-Br, 5-C≡CSiMe$_3$, 4-C≡CH, 5-I, 4-CF$_3$, 4-c-propyl, 5-C≡CH, 4-CH$_2$Br, 4-CH=CH$_2$, or 5-CH=CH$_2$ and R$^4$ is H; (ii) R$^3$ is 4-I and R$^4$ is 5-I; (iii) R$^3$ is 4-Br and R$^4$ is 5-Br; (iv) R$^3$ is 5-C≡CH and R$^4$ is 4-Br; (v) R$^3$ is 5-Br and R$^4$ is 4-Me; and (vi) R$^3$ is 5-I and R$^4$ is 4-Et;

(3) G is

[structure: furan ring with R4 at 5-position, R3 at 4-position, O]

R$^1$ and R$^2$ are n-propyl, and
R$^3$ and R$^4$ are selected from the group consisting of (i) R$^3$ is 4-Br, 4-Cl, 4-I, 5-Br, 5-C≡CSiMe$_3$, 4-C≡CH, 5-I, H, 4-CF$_3$, 5-C≡CH, 4-CH=CH$_2$, or 5-CH=CH$_2$ and R$^4$ is H; (ii) R$^3$ is 4-I and R$^4$ is 5-I or 5-Et; (iii) R$^3$ is 4-Br and R$^4$ is 5-Br; (iv) R$^3$ is 5-C≡CH and R$^4$ is 4-Br; and (v) R$^3$ is 5-Br and R$^4$ is 4-Me; or (4) G is

[structure: furan ring with R4 at 5-position, R3 at 4-position, O]

R$^1$ and R$^2$ are n-propyl, and
R$^3$ and R$^4$ are selected from the group consisting of (i) R$^3$ is 4-Br, 4-Cl, 4-I, 5-Br, 5-C≡CSiMe$_3$, 4-C≡CH, 5-I, 4-CF$_3$, 4-c-propyl, 5-C≡CH, 4-CH$_2$Br, 4-CH=CH$_2$, or 5-CH=CH$_2$ and R$^4$ is H; (ii) R$^3$ is 4-I and R$^4$ is 5-I; (iii) R$^3$ is 4-Br and R$^4$ is 5-Br; (iv) R$^3$ is 5-C≡CH and R$^4$ is 4-Br; (v) R$^3$ is 5-Br and R$^4$ is 4-Me; (vi) R$^3$ is 5-I and R$^4$ is 4-Et.

4. A compound of claim 1 wherein
(1) G is

[structure: thiophene ring with Br substituent]

Q is O;
R$^2$ is n-propyl;
W is O, NH, or S; and
R$^1$ is Me, n-Bu, n-pentyl, n-hexyl, Et, i-Pr, i-Bu, s-Bu, c-propyl, c-butyl, c-pentyl, 2-propenyl, 3-butenyl, 2-propynyl, 3-butynyl, CF$_3$, 2-Cl-Et, 3-Br-n-Pr, —CH$_2$CH=CHCl, —CH$_2$C≡CCl, —CH$_2$OCH$_3$, —CH$_2$OCH$_2$CH$_3$, —CH$_2$SCH$_3$, —CH$_2$SCH$_2$CH$_3$, —CH$_2$CH$_2$SCH$_3$, —CH$_2$CH$_2$OCH$_2$C≡CH, —CH$_2$CH$_2$CH$_2$S(O)$_2$CH$_3$, (c-pentyl)CH$_2$—, —CH$_2$CH$_2$OCH$_2$CH=CH$_2$, —CH$_2$CH$_2$SCH$_2$C≡CH, —CH$_2$OCF$_3$, —CH$_2$OCH$_2$CH$_2$Cl, —CH$_2$CH$_2$SCH$_2$CH=CH$_2$, —CH$_2$CH$_2$NO$_2$, —CH$_2$CH=CHCH$_2$OCH$_3$, —CH$_2$CH$_2$N(CH$_3$)$_2$, —CH$_2$CH=CHCH$_2$SCH$_3$, —NHCH$_2$CH$_2$CH$_3$, —CH$_2$CH$_2$Si(CH$_3$)$_3$, —CH$_2$CH$_2$CO$_2$CH$_3$, —CH$_2$CH$_2$CH$_2$NHCH$_3$, 2-furanyl, —CH$_2$CH$_2$CH$_2$CN, Ph, —OCH$_2$CH$_2$CH$_3$, 3-benzo[b]thiophenyl, —N(CH$_3$)CH$_2$CH$_3$, (2-THF)CH$_2$-, 2-pyridinyl, 3-MeO-Ph, 2-thienyl, 4-F-Ph, 5-benzofuranyl, 4-PhO-Ph, 3-quinolinyl, 3-CF$_3$O-Ph, 2-F-4-Me-Ph, c-hexyl, 2-F-4-Cl-Ph, 4-Cl-Ph, 4-MeS-Ph, (c-propyl)CH$_2$—, 4-Ph-Ph, or 3-NO$_2$-Ph; or (2) G is

[structure: thiophene ring with Br substituent];

Q is O;
R$^2$ is n-propyl;
W is O, NH, or S; and
R$^1$ is Et, n-Pr, i-Pr, n-Bu, i-Bu, s-Bu, n-pentyl, n-hexyl, n-decyl, c-hexyl, 2-propenyl, 2-butenyl, 3-butenyl, 5-decenyl, 2-propynyl, 2-butynyl, 3-butynyl, —CF$_3$, —CH$_2$CF$_3$, —CH$_2$CH=CHCl, —CH$_2$C≡CBr, —CH$_2$OCH$_3$, —CH$_2$OCH$_2$CH$_3$, —CH$_2$CH$_2$OCH$_3$, —CH$_2$SCH$_3$, —CH$_2$CH$_2$SCH$_3$, —CH$_2$CH$_2$CH$_2$S(O)$_2$CH$_3$, (c-pentyl)CH$_2$—, 2-Cl-Et, —CH$_2$CH$_2$OCH$_2$C≡CH, —CH$_2$CH$_2$SCH$_2$CH=CH$_2$, —CH$_2$CH$_2$CH$_2$CN, —CH$_2$CH$_2$Si(CH$_3$)$_3$, —CH$_2$CH$_2$OCF$_3$, —CH$_2$CH$_2$SCH$_2$C≡CH, —CH$_2$OCH$_2$CH$_2$Cl, Ph, —CH$_2$CH$_2$CO$_2$Et, —CH$_2$CH$_2$CH$_2$N(CH$_3$)$_2$, —CH$_2$CH$_2$(4-F-Ph), 4-MeO-Ph, —CH$_2$Ph, —CH$_2$CH$_2$OCH$_2$CH=CH$_2$, —N(CH$_3$)$_2$, —CH$_2$CH$_2$CH$_2$NHCH$_3$, —CH$_2$CH$_2$NO$_2$, —NHCH$_2$CH$_2$CH$_3$, 2-CN-Ph, 2,4-diCl-Ph, 2,4,6-triF-Ph, 4-CF$_3$-Ph, —CH$_2$CH$_2$CH$_2$Ph, (2-THF)CH$_2$—, (c-propyl)CH$_2$—, —CH$_2$CN or 4-Cl-Ph.

5. A compound selected from Formula I, N-oxides and agriculturally suitable salts thereof,

[structure of Formula I: pyrimidinone with R$^3$, R$^4$, G, Q, R$^1$, N, WR$^2$]

I wherein
W is O, S(O)$_n$ or NR$^5$;
n is 0, 1 or 2;
G is a fused thiophene ring;
R$^1$ is C$_1$–C$_8$ alkyl; C$_3$–C$_5$ cycloalkyl; C$_3$–C$_8$ alkenyl; C$_3$–C$_8$ alkynyl; C$_1$–C$_8$ haloalkyl; C$_3$–C$_8$ haloalkenyl; C$_2$–C$_8$ alkoxyalkyl; C$_2$–C$_8$ alkylthioalkyl; C$_4$–C$_8$ cycloalkylalkyl; C$_4$–C$_8$ alkenyloxyalkyl; C$_1$–C$_8$ alkoxy; phenyl, pyridinyl, furanyl or thienyl each optionally substituted with $R^8$ and $R^9$; or $C_1$–$C_8$ alkyl substituted with cyano;

$R^2$ is $C_1$–$C_8$ alkyl; $C_3$–$C_8$ alkenyl; $C_3$–$C_8$ alkynyl; $C_1$–$C_8$ haloalkyl; $C_3$–$C_8$ haloalkenyl; $C_2$–$C_8$ alkoxyalkyl; $C_2$–$C_8$ alkylthioalkyl; $C_4$–$C_8$ cycloalkylalkyl; $C_4$–$C_8$ alkenyloxyalkyl; phenyl optionally substituted with $R^8$; or $C_1$–$C_8$ alkyl substituted with cyano; or when W is $NR^5$, then $R^2$ can additionally be selected from —N=$CR^6R^6$ and —$NR^6R^7$;

$R^3$ is halogen, $C_3$–$C_8$ cycloalkyl, $C_2$–$C_8$ alkynyl, $C_1$–$C_8$ haloalkyl, $C_1$–$C_8$ alkoxy, $C_1$–$C_8$ haloalkoxy, $C_1$–$C_8$ alkylthio, $C_1$–$C_8$ alkylsulfonyl, $C_2$–$C_8$ alkoxyalkyl or $C_5$–$C_8$ trialkylsilylalkynyl;

$R^4$ is hydrogen, halogen, $C_1$–$C_4$ alkyl, $C_1$–$C_4$ haloalkyl, $C_1$–$C_4$ alkoxy or $C_1$–$C_4$ haloalkoxy;

$R^5$ is hydrogen, $C_1$–$C_4$ alkyl or —C(=O)$R^{12}$;

each $R^6$ is independently hydrogen; $C_1$–$C_4$ alkyl; or phenyl optionally substituted with at least one $R^{13}$;

each $R^7$ is independently hydrogen; $C_1$–$C_8$ alkyl; or phenyl optionally substituted with at least one $R^{13}$; or each pair of $R^6$ and $R^7$, when attached to the same nitrogen atom, can independently be taken together as —CH$_2$CH$_2$CH$_2$CH$_2$—, —CH$_2$(CH$_2$)$_3$CH$_2$—, —CH$_2$CH$_2$OCH$_2$CH$_2$—, —CH$_2$CH(Me)CH$_2$CH(Me)CH$_2$— or —CH$_2$CH(Me)OCH(Me)CH$_2$—;

each $R^8$ is independently methyl, ethyl, methoxy, ethoxy, $C_1$–$C_2$ haloalkyl, halogen, ethynyl, 2-propynyl, methylthio, ethylthio, cyano, nitro, $C_1$–$C_2$ haloalkoxy, ethenyl, 2-propenyl, acetyl, CO$_2$Me or N($C_1$–$C_2$ alkyl)$_2$;

$R^9$ is methyl, ethyl, methoxy, methylthio, halogen or trifluoromethyl;

$R^{12}$ is hydrogen, $C_1$–$C_4$ alkyl, $C_1$–$C_4$ alkoxy or $NR^6R^7$; and each $R^{13}$ is independently halogen, $C_1$–$C_4$ alkyl, $C_1$–$C_4$ alkoxy, $C_1$–$C_4$ haloalkyl, nitro or cyano.

6. A compound of claim 5 wherein $R^1$ is $C_3$–$C_8$ alkyl; $C_3$–$C_8$ alkenyl; $C_3$–$C_8$ alkynyl; $C_3$–$C_8$ haloalkyl; $C_3$–$C_8$ haloalkenyl; $C_3$–$C_8$ alkoxyalkyl; or phenyl optionally substituted with $R^8$ and $R^9$;

$R^2$ is $C_3$–$C_8$ alkyl; $C_3$–$C_8$ alkenyl; $C_3$–$C_8$ alkynyl; $C_3$–$C_8$ haloalkyl; $C_3$–$C_8$ haloalkenyl; $C_3$–$C_8$ alkoxyalkyl; or phenyl optionally substituted with $R^8$; or when W is $NR^5$, then $R^2$ can additionally be selected from —N=$CR^6R^6$ and —$NR^6R^7$;

$R^3$ is halogen, ethynyl, $C_1$–$C_4$ haloalkyl, $C_1$–$C_4$ alkoxy, $C_1$–$C_4$ haloalkoxy or trimethylsilylethynyl; and each $R^8$ is independently methyl, ethyl, methoxy, trifluoromethyl, halogen, methylthio or N($C_1$–$C_2$ alkyl)$_2$.

7. A compound of claim 6 wherein $R^1$ is $C_3$–$C_8$ alkyl, $C_3$–$C_8$ alkenyl, $C_3$–$C_8$ alkynyl, $C_3$–$C_8$ haloalkyl or $C_3$–$C_8$ haloalkenyl;

$R^2$ is $C_3$–$C_8$ alkyl; $C_3$–$C_8$ alkenyl; $C_3$–$C_8$ alkynyl; $C_3$–$C_8$ haloalkyl; $C_3$–$C_8$ haloalkenyl; or phenyl optionally substituted with $R^8$;

$R^3$ is halogen; and $R^4$ is hydrogen or halogen.

8. The compound of claim 5 which is selected from the group 7-bromo-2-propoxy-3-propylthieno[3,2-d]pyrimidin-4(3H)-one and 6,7-dibromo-2-propoxy-3-propylthieno[3,2-d]pyrimidin-4(3H)-one.

9. A compound of claim 5 which is selected from the group

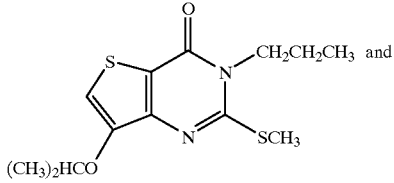

and

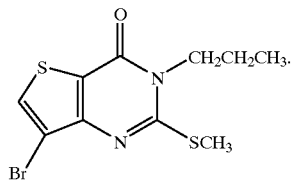

10. A compound of claim 5 which is selected from the group consisting of 6-bromo-2-propoxy-3-propylthieno[2,3-d]pyrimidin-4(3H)-one, and 7-bromo-2-propoxy-3-propylthieno[3,2-d]pyrimidin-4(3H)-one.

11. A method of preparing a compound of claim 1, comprising:

(A) preparing a compound of Formula Ic

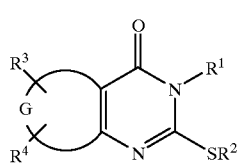

by (1) forming a compound of Formula 2

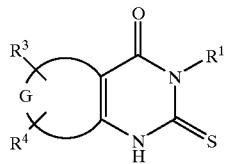

either by (a) converting a compound of Formula 3

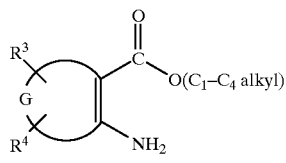

with thiophosgene and treating the resulting isothiocyanate with an amine of Formula NH$_2R^1$;

or by (b) treating a compound of Formula 1

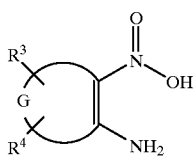

1 with an isothiocyanate of the Formula $R^1$-NCS;
or by (c) treating a compound of Formula 3a

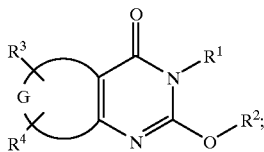

3a with an isothiocyanate of the Formula $CH_3CH_2CH_2$-NCS;
and (2) treating said compound of Formula 2 with a compound of Formula $R^2$-X, wherein X is Br, I, $CH_3SO_3$— or (4-$CH_3$-Ph)$SO_3$—, in the presence of a base, provided that for (A)(1)(c) the compound of Formula 2 is treated with $CH_3I$ in the presence of NaOH; and (B) if desired, for a compound of Formula Ic wherein $R^2$ is methyl, either (1) treating said compound with a compound of Formula $R^2$-OH in the presence of a base to prepare a compound of Formula Ib

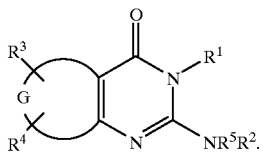

Ib or (2) treating said compound with a compound of Formula $HNR^5R^2$ to prepare a compound of Formula Ie

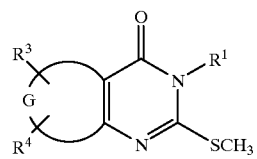

Ie

12. The method of claim 11 wherein the compound of Formula 3a is treated with $CH_3I$ in the presence of NaOH.
13. The method of claim 11 comprising
(A) preparing a compound of Formula Ia

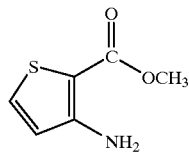

Ia by (1) forming a compound of Formula 2

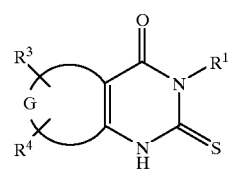

2 by treating a compound of Formula 1

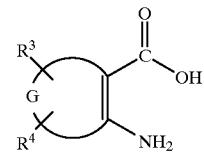

1 with an isothiocyanate of the Formula $R^1$-NCS in ethanol with heat;
and (2) treating said compound of Formula 2 with $CH_3I$ in the presence of NaOH in n-propanol; and
(B) treating said compound of Formula Ia prepared in (A) with a compound of Formula $R^2$-OH in the presence of NaH with heat to prepare a compound of Formula Ib

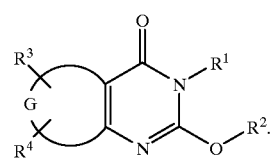

Ib

14. A method of preparing a compound of claim 5, wherein $R^3$ is halogen and $R^4$ is hydrogen or halogen, comprising:
   treating a fused thienopyrimidinone compound of the formula

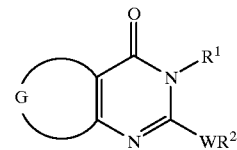

with a halogenating agent to provide a compound of Formula I wherein $R^3$ is halogen and $R^4$ is hydrogen or halogen.
15. The method of claim 14 wherein 7-bromo-2-(methylthio)-3-propylthieno[3,2-d]pyrimidin-4(3H)-one is prepared by treating 2-(methylthio)-3-propylthieno[3,2-d]pyrimidin-4(3H)-one with bromine in acetic acid.
16. A fungicidal composition comprising a fungicidally effective amount of a compound of claim 1 and at least one component selected from the group consisting of surfactants, solid diluents or liquid diluents.
17. A method for controlling plant diseases caused by fungal plant pathogens comprising applying to the plant or portion thereof, or to the plant seed or seedling, a fungicidally effective amount of a compound of claim 1.

* * * * *